(12) United States Patent
Jaques et al.

(10) Patent No.: US 11,320,422 B2
(45) Date of Patent: May 3, 2022

(54) INHIBITION OF PROTEIN DEGRADATION FOR IMPROVED PRODUCTION

(71) Applicant: LONZA LTD, Visp (CH)

(72) Inventors: Colin Mark Jaques, London (GB); Christopher Mark Smales, Canterbury (GB); Tanya Jeane Knight, Herne Bay (GB)

(73) Assignee: Lonza Ltd., Visp (CH)

( * ) Notice: Subject to any disclaimer, the term of this patent is extended or adjusted under 35 U.S.C. 154(b) by 0 days.

(21) Appl. No.: 16/068,422

(22) PCT Filed: Jan. 6, 2017

(86) PCT No.: PCT/EP2017/050259
§ 371 (c)(1),
(2) Date: Jul. 6, 2018

(87) PCT Pub. No.: WO2017/118726
PCT Pub. Date: Jul. 13, 2017

(65) Prior Publication Data
US 2019/0120824 A1 Apr. 25, 2019

Related U.S. Application Data

(60) Provisional application No. 62/276,339, filed on Jan. 8, 2016, provisional application No. 62/275,691, filed on Jan. 6, 2016.

(51) Int. Cl.
| | | |
|---|---|---|
| *G01N 33/50* | (2006.01) | |
| *C12N 5/00* | (2006.01) | |
| *C12N 15/65* | (2006.01) | |

(52) U.S. Cl.
CPC ....... *G01N 33/5023* (2013.01); *C12N 5/0068* (2013.01); *C12N 15/65* (2013.01); *G01N 33/5005* (2013.01); *C12N 2501/734* (2013.01); *C12N 2510/00* (2013.01)

(58) Field of Classification Search
CPC .......... G01N 33/5023; G01N 33/5005; C12N 15/65; C12N 5/0068; C12N 5/0682; C12N 2510/00; C12N 2510/734; C12N 2510/02; C12N 2501/734; C07K 16/00; C12Q 1/27; C12Q 1/25; C12Q 1/37; C12P 21/00
See application file for complete search history.

(56) References Cited

U.S. PATENT DOCUMENTS

2010/0129343 A1* 5/2010 Freissmuth ............ A61K 38/06
424/94.63

OTHER PUBLICATIONS

Rasala et al., Enhanced Genetic Tools for Engineering Multigene Traits into Green Algae, PLOS One, vol. 9 issue 4, 8 pages (Year: 2014).*
Wang et al., The Journal of Biological Chemsitry, 2011, vol. 286 pp. 43545-43464.*
Li et al., Cell culture processes for monoclonal antibody production, 2010, mAbs, 2, 5, 466-479 (Year: 2010).*
Yuan et al., Proteasome inhibitor MG132 induces apoptosis and inhibits invasion of human malignant pleural mesothelioma cells, 2008, Translational Oncology, 1, 129-140 (Year: 2008).*
Wang et al., Inhibition of p97-dependent Protein Degradation by Eeyarestatin I, 2008, JBC, 283, 7445-7454 (Year: 2008).*
Li et al., Interprotomer motion-transmission mechanism for the hexameric AAA ATPase p97, 2012, PNAS, vol. 109, 3737-3741 (Year: 2012).*
Wen et al., MG-132 Improve the Production of TNFR-Fc Fusion Protein in CHO Cells, 2015, China Biotechnology, vol. 35, pp. 1-6 (abstract only) (Year: 2015).*
Wen et al., MG-132 Improve the Production of TNFR-Fc Fusion Protein in CHO Cells, 2015, China Biotechnology, vol. 35, pp. 1-6 (untranslated) (Year: 2015).*
Chondrogianni et al. "Central Role of the Proteasome in Senescence and Survival of Human Fibroblasts" The Journal of Biological Chemistry (2003) vol. 278, No. 30, pp. 28026-28037.
Fischer et al. "A functional high-content miRNA screen identifies miR-30 family to boost recombinant protein production in CHO cells" Biotechnology Journal (2014) vol. 9, pp. 1279-1292.
Fischer et al. "Enhanced protein production by microRNA-30 family in CHO cells is mediated by the modulation of the ubiquitin pathway" Journal of Biotechnology (2015) vol. 212, pp. 32-43.
Gelman et al. "A Principal Role for the Proteasome in Endoplasmic Reticulum-associated Degradation of Misfolded Intracellular Cystic Fibrosis Transmembrane Conductance Regulator" The Journal of Biological Chemistry (2002) vol. 277, No. 14, p. 11709-11714.
International Search Report and Invitation to Pay Additional Fees for International Application No. PCT/EP2017/050259 dated Mar. 3, 2017.
International Search Report and Written Opinion for International Application No. PCT/EP2017/050259 dated May 24, 2017.

* cited by examiner

*Primary Examiner* — Nancy J Leith
(74) *Attorney, Agent, or Firm* — Lucas & Mercanti, LLP

(57) ABSTRACT

Disclosed herein are methods and compositions useful for evaluating, selecting, identifying, or making a cell or cell line that has improved production capacity for generating higher yields of products and/or improved capacity to produce higher quality products. Products, as described herein, can include a polypeptide that is endogenously expressed by the cell, a recombinant polypeptide that is not endogenously expressed, or a non-naturally occurring recombinant polypeptide. The methods described herein include modulating, e.g., inhibiting, the protein degradation pathway by using a proteasome inhibitor, an ER-associated degradation (ERAD) inhibitor, or a ubiquitin pathway inhibitor.

36 Claims, 42 Drawing Sheets

INHIBITION OF PROTEIN DEGRADATION FOR IMPROVED PRODUCTION

This application is a U.S. national phase application and claims the benefit of priority under 35 U.S.C. § 371 of International Application No. PCT/EP2017/050259, filed Jan. 6, 2017, which claims priority to U.S. Application 62/275,961 filed Jan. 6, 2016; and U.S. Application 62/276,339 filed Jan. 8, 2016, the entire contents of each of these applications are incorporated herein by reference.

FIELD OF THE INVENTION

The present disclosure relates to cells and cell lines, e.g., eukaryotic cells and cell lines, for production of a product, e.g., a recombinant protein. The present disclosure also relates to modulation of the protein degradation pathway for improved production of the product, e.g., the recombinant protein.

BACKGROUND

The generation and selection of high-producing recombinant CHO cell lines has been highlighted as a bottleneck in the cell line development process. Thus, there is a need for methods for identifying and generating cell lines that have the capacity for high production of recombinant proteins.

SUMMARY

The present disclosure is based, in part, on the discovery that there is a correlation between the ability of a cell, e.g., an eukaryotic cell, e.g. a mammalian or a cell other than a mammalian cell, to produce a product, e.g., a recombinant polypeptide, and susceptibility to inhibitors of the protein degradation pathway, e.g., proteasome inhibitors, ubiquitin pathway inhibitors, and ERAD inhibitors. Without wishing to be bound by theory, it is believed that inhibitors of the protein degradation pathway can be used to select for high productivity cells, e.g., cells that are capable of producing high yields of a product, e.g., a recombinant polypeptide. Accordingly, disclosed herein are methods and processes for evaluating, selecting, classifying, or identifying cells for producing a product, e.g., a recombinant polypeptide. Also provided herein are methods and processes for making a cell or cell line for producing a product, e.g., a recombinant polypeptide, by identifying or selecting a cell that is capable of high productivity. These methods and processes described herein include contacting the cell with an inhibitor of protein degradation, e.g., inhibits or reduces the activity of the protein degradation pathway. Thus, provided herein are methods for not only identifying better quality of cells, e.g., with higher production capacity, for producing products, e.g., recombinant polypeptides, but also provides cells that produce better quality of products, e.g., recombinant polypeptide products, e.g., monoclonal antibodies and difficult to express proteins, e.g., bispecific molecules.

In one aspect, the present disclosure features a method of evaluating, classifying, identifying, making, or selecting, a cell or a progeny cell or population of progeny cells, e.g., for production of a product, e.g., a polypeptide, e.g., a recombinant polypeptide. In one embodiment, the method comprises:

a) optionally, providing a cell;
b) contacting the cell (or progeny of the cell) with an inhibitor of protein degradation, e.g., a proteasome inhibitor, a ubiquitin pathway inhibitor, or an endoplasmic reticulum associated degradation (ERAD) inhibitor;
c) evaluating the effect of the inhibitor of protein degradation, e.g., proteasome inhibitor, ubiquitin pathway inhibitor, or an ERAD inhibitor, on one or more parameters related to cell function, in the cell (or progeny of the cell);
d) optionally, comparing a value for the effect of the inhibitor of protein degradation, e.g., proteasome inhibitor, on the one or more parameters with a reference value; and
e) optionally, expressing a product, e.g., a recombinant polypeptide from the cell (or progeny of the cell); and thereby evaluating, classifying, identifying, making, or selecting, a cell or a progeny cell or population of progeny cells. In one embodiment, the method comprises providing a cell. In one embodiment, the method comprises comparing a value for the effect of the inhibitor of protein degradation, e.g., proteasome inhibitor, on the one or more parameters with a reference value. In one embodiment, the method comprises expressing a product, e.g., a recombinant polypeptide from the cell (or progeny of the cell).

The products produced by the cells and methods described herein can be a molecule, a nucleic acid, a polypeptide, or any fusion or hybrid thereof. In one embodiment, the product is a non-naturally occurring material or molecule. In another embodiment, the product is a naturally occurring material or molecule. The cells producing the products described herein are engineered or modified to control, e.g., increase the expression, or produce, e.g., encode, the products described herein. In one embodiment, the cells are engineered or modified to comprise an exogenous nucleic acid that controls, e.g., increases, the expression of an endogenously expressed product. In another embodiment, the cells are engineered or modified to comprise an exogenous nucleic acid that encodes a product, e.g., an endogenously expressed product, a product that is not endogenously produced by the cell, or a non-naturally occurring product.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises evaluating a cell or a progeny cell or population of progeny cells.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises classifying a cell or a progeny cell or population of progeny cells.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises identifying a cell or a progeny cell or population of progeny cells.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises making a cell or a progeny cell or population of progeny cells.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises selecting a cell or a progeny cell or population of progeny cells.

In one embodiment, the method of evaluating, classifying, identifying, making, or selecting, a cell or a progeny cell or population of progeny cells, e.g., for production of a product, e.g., a polypeptide, a recombinant polypeptide further comprises, e.g., as a part of step (b), culturing the cell (or progeny of the cell) in contact with the inhibitor of protein degradation.

The methods described herein comprise identifying or selecting a cell with improved, e.g., increased, production capacity, e.g., ability to produce a product, e.g., a polypeptide, e.g., a recombinant polypeptide. In one embodiment, the level, amount, or quantity of the product produced by the identified or selected cell is increased, e.g., by 1-fold, 2-fold, 3-fold, 4-fold, 5-fold, 6-fold, 7-fold, 8-fold, 9-fold, 10-fold, 20-fold, 50-fold, or 100-fold or more, as compared to the level, amount, or quantity produced by a cell that has not been contacted by the inhibitor of protein degradation.

The method described herein comprise identifying or selecting a cell with improved, e.g., increased, quality of a product, e.g., recombinant polypeptide. In one embodiment, the quality of the product produced by the identified or selected cell is increased, e.g., by 1-fold, 2-fold, 3-fold, 4-fold, 5-fold, 6-fold, 7-fold, 8-fold, 9-fold, 10-fold, 20-fold, 50-fold, or 100-fold or more, as compared to quality of the product produced by a cell that has not been contacted by the inhibitor of protein degradation. In one embodiment, the improved quality of the product comprises one or more of the following: an increased level, amount, or proportion of the desired product, e.g., with respect to unwanted isoforms, fragmented, or truncated forms; an increased level, amount, or proportion of properly folded product; an increased level, amount, or proportion of functional, e.g., enzymatically active, product; a decreased level, amount, or proportion of aggregated product; or a decreased level, amount, or proportion of fragmented or unwanted isoforms.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises comparing a value for the effect of the inhibitor of protein degradation, e.g., a proteasome inhibitor, with a reference value. In embodiments wherein the value has a predetermined relationship with the reference value, the method comprises classifying, or selecting, a cell or a progeny cell or population of progeny cells, e.g., for establishing a culture, e.g., a cell bank. In some embodiments, wherein the value meets or exceeds the reference value, the method comprises classifying, or selecting, a cell or a progeny cell or population of progeny cells, e.g., for establishing a culture, e.g., a cell bank or for production of a polypeptide, e.g., a recombinant polypeptide. In embodiments wherein the value has a predetermined relationship with the reference value, the method comprises classifying, or selecting, a cell or a progeny cell or population of progeny cells, e.g., for production of a polypeptide, e.g., a recombinant polypeptide. In embodiments wherein when the value meets or exceeds a reference value, the cell or a progeny cell or population of progeny cells is classified, identified, or selected as a production cell or a progeny cell or population of progeny cells. In some embodiments, wherein the value has a predetermined relationship with the reference value, the method comprises selecting the cell (or a progeny of the cell), e.g., for making a cell line or population of cells.

In one embodiment, the parameter related to cell function comprises, e.g., is selected from:
i) cell survival,
ii) culture viability,
iii) the ability to produce a product, e.g., a polypeptide, e.g., a recombinant polypeptide,
iv) proteasome activity; or
v) quality of the expressed product, e.g., a polypeptide, e.g., a recombinant polypeptide, e.g., a more homogeneous product.

In one embodiment, the method comprises evaluating more than one parameter. In one embodiment, the method comprises evaluating more than one parameter, and the parameters measured are compared with a reference value.

Also provided herein are methods for establishing a cell line from the cell or a progeny cell of a cell described herein. In one embodiment, the method further comprises culturing the cell to provide a population of cultured cells, e.g., a population of progeny cells. In one embodiment, the method further comprises selecting a cell from the population of cultured cells, e.g., a population of progeny cells. In one embodiment, the method comprises evaluating the selected cell (or progeny of the cell) for a parameter related to cell function, e.g., providing a value for the parameter, e.g., a parameter related to cell function as described herein. In such embodiments wherein the value has a predetermined relationship with the reference value, selecting the cell (or a progeny of the cell), e.g., for production of a polypeptide, e.g., a recombinant polypeptide. In embodiments wherein the value meets or exceeds a reference value, the cell (or a progeny of the cell), is selected as a production cell. In one embodiment, the method further comprises establishing a cell line from said cell.

In one embodiment, the method of evaluating, classifying, identifying, making, or selecting, a cell or a progeny cell or population of progeny cells, e.g., for production of a product, e.g., a polypeptide, e.g., a recombinant polypeptide, further comprises introducing an exogenous nucleic acid into the cell. In one embodiment, the exogenous nucleic acid encodes a product, e.g., a recombinant polypeptide, or an exogenous nucleic acid that controls, e.g., increases, the expression of a product, e.g., an endogenous polypeptide. In one embodiment, the exogenous nucleic acid is introduced after one or more of steps a), b), c) and d). In one embodiment, the exogenous nucleic acid is introduced prior to one or more of steps a), b), c) and d). In one embodiment, the exogenous nucleic acid encodes a polypeptide, e.g., a recombinant polypeptide, e.g. a therapeutic polypeptide or an antibody molecule selected from Table 1 or 2. In one embodiment, the method further comprises introducing one or more additional exogenous nucleic acids, e.g., a second exogenous nucleic acid, into the cell. In one embodiment, the second exogenous nucleic acid is introduced after one or more of steps a), b), c) and d). In one embodiment, the second exogenous nucleic acid is introduced prior to one or more of steps a), b), c) and d). In one embodiment, the second exogenous nucleic acid is introduced after introduction of the first exogenous nucleic acid. In one embodiment, the second exogenous nucleic acid is introduced prior to introduction of the first exogenous nucleic acid. In one embodiment, the second exogenous nucleic acid is introduced simultaneously with the first exogenous nucleic acid. In one embodiment, the second exogenous nucleic acid encodes a selection marker, e.g., glutamine synthetase. In one embodiment, the method further comprises introducing an exogenous nucleic acid comprises transfection, electroporation, or transduction.

In one embodiment, the method of evaluating, classifying, identifying, making, or selecting, a cell or a progeny cell or population of progeny cells, e.g., for production of a product, e.g., a polypeptide, e.g., a recombinant polypeptide, further comprises evaluating the cell for a second property, e.g., determining if the cell comprises an exogenous component, e.g., one or more exogenous nucleic acids, e.g., one or more exogenous nucleic acids integrated into a nucleic acid of the cell, e.g., integrated into the chromosomal genome of the cell. In one embodiment, the method comprises determining if the cell comprises one or more exogenous nucleic acids integrated into a nucleic acid of the cell, e.g., integrated into the chromosomal genome of the cell, comprises MSX selection, MTX selection (e.g., DHFR system), antibiotic selection, yeast growth selection, selection based on color change or surface expression of a marker, selection based on the Selexis® system, or selection based on the Catalant system. In one embodiment, antibiotic selection comprises selection for resistance to an antibiotic selected from hygromycin, neomycin (G418), zeocin, puromycin, or blasticidin.

In one embodiment, the method of evaluating, classifying, identifying, making, or selecting, a cell or a progeny cell or population of progeny cells, e.g., for production of a product, e.g., a polypeptide, e.g., a recombinant polypeptide, comprises evaluating the effect of the inhibitor of protein degradation, e.g., proteasome inhibitor, on a parameter related to cell function, e.g., survival, viability, or the ability to proliferate, or to produce a product, e.g., a polypeptide, e.g., a polypeptide expressed from an exogenous nucleic acid; and determining, e.g., by MSX selection, if the cell comprises an exogenous nucleic acid integrated into the chromosomal genome of the cell. In one embodiment, wherein responsive to the evaluation in the effect of the inhibitor of protein degradation step and the determining if the cell comprises an exogenous nucleic acid integrated into the chromosomal genome of the cell step, evaluating, classifying, identifying, or selecting, a cell, progeny cell or population of progeny cells.

In one embodiment, the method of evaluating, classifying, identifying, making, or selecting, a cell or a progeny cell or population of progeny cells, e.g., for production of a product, e.g., a polypeptide, e.g., a recombinant polypeptide, further comprises an additional selection step, e.g., selection by FACS, magnetic separation, e.g., magnetic beads, colony picking, microfluidic cell sorting, or microfluidic cell destruction. In embodiments, the selection step comprises determining whether the cell comprises one or more exogenous nucleic acids. In embodiments, the selection step comprises determining whether the cell comprises one or more exogenous nucleic acids integrated into a nucleic acid of the cell, e.g., integrated into the chromosomal genome of the cell.

In one embodiment, the method of evaluating, classifying, identifying, making, or selecting, a cell or a progeny cell or population of progeny cells, e.g., for production of a product, e.g., a polypeptide, e.g., a recombinant polypeptide, further comprises introducing to the cell an agent that assists in protein folding, e.g., chaperone molecules or small chemical molecules. In one embodiment, the agent that assists in protein folding comprises a nucleic acid encoding a chaperone protein or component of the protein folding pathway, e.g., XBP1, SRP14, BiP/GRP78, PDI, calnexin or cyclophilin B. In one embodiment, the agent that assists in protein folding comprises a small molecule selected from DMSO, glycerol, or PBA.

In another aspect, the present disclosure features a method of making a cell line, or population of cells, comprising identifying a cell by the methods described herein; and culturing the cell, or population of cells, to provide a cell line or population of cells. In another aspect, the present disclosure features a method of making a cell line, or population of cells, comprising identifying or selecting a cell by the methods described herein; and culturing the cell, or population of cells, to provide a cell line or population of cells.

In another aspect, the present disclosure features a method of making a product, e.g., a polypeptide, e.g., a recombinant polypeptide, comprising: providing a cell or cell population made by the methods described herein; culturing the cell or cell population in a culture medium; and, optionally, retrieving the product, e.g., polypeptide, e.g., the recombinant polypeptide, from the cell or medium in which the cell was cultured.

In another aspect, the present disclosure features a cell, progeny cell, or population of progeny cells, evaluated, classified, or selected by any of the methods described herein.

In another aspect, the present disclosure features a cell, progeny cell, or population of progeny cells, made by any of the methods described herein.

In another aspect, the present disclosure features a cell, progeny cell, or population of progeny cells, which can be made by any of the methods described herein.

In another aspect, the present disclosure features a product, e.g., a polypeptide, e.g., a recombinant polypeptide, produced by or producible by any of the methods described herein or any of the cells described herein.

In another aspect, the present disclosure features a preparation comprising a product described herein, e.g., a product, e.g., a polypeptide, e.g., a recombinant polypeptide, produced by, or producible by, any of the methods described herein or any of the cells described herein.

In another aspect, the present disclosure features a mixture comprising a cell described herein and a product described herein, e.g., a polypeptide, e.g., recombinant polypeptide.

In another aspect, the present disclosure features a preparation of medium conditioned by culture of a cell, progeny cell, or population of progeny cells, described herein, e.g., a cell, progeny cell, or population of progeny cells described herein.

In another aspect, the present disclosure features a method of making a cell, or progeny of a cell, that produces a recombinant protein (e.g., a recombinant therapeutic protein, e.g., a recombinant therapeutic antibody), comprising:
  a) optionally, providing a cell;
  b) culturing the cell or the progeny of the cell in the presence of an exogenous inhibitor of protein degradation, e.g., a proteasome inhibitor, a ubiquitin pathway inhibitor, or an endoplasmic reticulum associated degradation (ERAD) inhibitor (e.g., for at least 1, 2, 3, 4, 5, 6, 7, 8, 9, 10, 20, 30, 40, 50 or more passages or for at least 12, 24, 48, 72 hours, or 1, 2, 4, 8, 16, 32 or more weeks);
  c) culturing the cell or progeny of the cell in the absence of the exogenous inhibitor of protein degradation (e.g., for at least 1, 2, 3, 4, 5, 6, 7, 8, 9, 10, or more passages or for at least 12, 24, 48, 72 hours);
  d) optionally, evaluating the effect of the inhibitor of protein degradation on the level of recombinant protein produced by the cell or the progeny of the cell, e.g., to obtain a value of recombinant protein produced by the cell or the progeny of the cell; and
  e) optionally, comparing the value obtained in d) with a reference value, wherein the reference value is the level of recombinant protein produced by a cell of the same type as the cell provided in a) cultured in the absence of the exogenous inhibitor of protein degradation;
  thereby making the cell or progeny of cells.

Additional features or embodiments of any of the methods or compositions described herein include one or more of the following:

Inhibitors of Protein Degradation

In embodiments of any of the methods or compositions described herein, the inhibitor of protein degradation is a proteasome inhibitor. In one embodiment, the proteasome inhibitor inhibits or reduces the activity of one or more of the 20S core subunit, the 19S regulatory subunit, the 11S regulatory particle, or a chaperone protein that assist proteasome assembly, e.g., Hsm3/S5b, Nas2/p27, Rpn14/PAAF1, and Nas6/gankyrin. In one embodiment, the proteasome inhibitor is selected from MG132 (Z-LLL-al, Z-Leu-Leu-Leu-al, Z-Leu-Leu-Leu-CHO), epoxomicin, bortezomib, ixazomib, carfilzomib, disulfiram, CEP-18770, ONX 0912, salinosporamide, LLnV, CEP1612, lactacystin, PS-341, and eponomicin.

In embodiments of any of the methods or compositions described herein, the inhibitor of protein degradation is an ERAD inhibitor. In one embodiment, the ERAD inhibitor inhibits or reduces the activity of one or more of calnexin/calreticulin, UDP-glucose-glycoprotein glucosyltransferase, ER degradation enhancing α-mannosidase-like protein (EDEM), ER mannosidase I, Sec61, CDC48p (VCP/p97), Hrd1, Doa10, Ubc6, Ubc1, Cue1, or Ubc7. In one embodiment, the inhibitor of protein degradation is eeyarestatin I.

In embodiments of any of the methods or compositions described herein, the inhibitor of protein degradation is an ubiquitin pathway inhibitor. In one embodiment, the ubiquitin pathway inhibitor inhibits or reduces the activity of one or more of: E1 ubiquitin activating enzyme, E2 ubiquitin conjugating enzyme, or E3 ubiquitin ligase.

In embodiments of any of the methods described herein, the method further comprises contacting the candidate cell with a second inhibitor of protein degradation, e.g., a proteasome inhibitor, an ERAD inhibitor, or an ubiquitin pathway inhibitor. In one embodiment, the cell is contacted with the first and second inhibitor of protein degradation, e.g., concurrently or sequentially. In one embodiment, the first inhibitor of protein degradation and second inhibitor of protein degradation are selected from MG132, epoxomicin, or eeyarestatin 1. In one embodiment, the cell is contacted with the first and second inhibitor of protein degradation, e.g., concurrently or sequentially, and the first inhibitor is a proteasome inhibitor and the second inhibitor is a proteasome inhibitor. In one embodiment, the cell is contacted with the first and second inhibitor of protein degradation, e.g., concurrently or sequentially, and the first inhibitor is a proteasome inhibitor and the second inhibitor is an ERAD inhibitor or an ubiquitin pathway inhibitor. In one embodiment, the cell is contacted with the first and second inhibitor of protein degradation, e.g., concurrently or sequentially, and the first inhibitor is an ERAD inhibitor and the second inhibitor is an ERAD inhibitor. In embodiments, the first inhibitor is different from the second inhibitor. In one embodiment, the cell is contacted with the first and second inhibitor of protein degradation, e.g., concurrently or sequentially, and the first inhibitor is an ERAD inhibitor and the second inhibitor is an ubiquitin pathway inhibitor or a proteasome inhibitor. In one embodiment, the cell is contacted with the first and second inhibitor of protein degradation, e.g., concurrently or sequentially, and the first inhibitor is an ubiquitin pathway inhibitor and the second inhibitor is an ubiquitin pathway inhibitor. In one embodiment, the cell is contacted with the first and second inhibitor of protein degradation, e.g., concurrently or sequentially, and the first inhibitor is an ubiquitin pathway inhibitor and the second inhibitor is an ERAD or a proteasome inhibitor.

In embodiments of any of the methods described herein, the cell is contacted with a concentration of the inhibitor of protein degradation that is sufficient to reduce culture viability, by about 10%, 20%, 25%, 30%, 35%, 40%, 45%, 50%, 55%, 60%, 65%, 70%, or 75%, 80%, 85%, 90, 95% or more, e.g., as compared to culture viability, before the culture is contacted with the inhibitor or as compared to a culture that is not contacted with the inhibitor. In one embodiment, the concentration of the inhibitor of protein degradation is a concentration at which less than 50%, 45%, 40%, 35%, 30%, 25%, 20%, 15%, 10%, 5%, 1%, 0.9%, 0.8%, 0.7%, 0.6%, 0.5%, 0.4%, 0.3%, 0.2%, 0.1%, or 0.05% total cells survive in culture after contact with the inhibitor of protein degradation. In one embodiment, the concentration of the inhibitor of protein degradation is a concentration at which one or more cells continue to proliferate. In one embodiment, the concentration of the inhibitor of protein degradation is less than 0.5 µM MG-132. In one embodiment, the concentration of the inhibitor of protein degradation is about 0.0625 µM MG-132. In one embodiment, the concentration of the inhibitor of protein degradation is less than 0.05 µM epoxomicin. In one embodiment, the concentration of the inhibitor of protein degradation is about 0.025 µM epoxomicin. In one embodiment, the concentration of the inhibitor of protein degradation is a low concentration of eeyarestatin I, e.g., 0.1 µM. In one embodiment, the concentration of the inhibitor of protein degradation is less than 0.5 µM eeyarestatin I, e.g., about 0.1 µM eeyarestatin I.

In embodiments of any of the methods described herein, the cell is contacted by the inhibitor of protein degradation for 24, 48, 72, 96, or 168 hours. In embodiments of any of the methods described herein, the cell (or the progeny of the cell) is cultured in the presence of the inhibitor of protein degradation for 24, 48, 72, 96, or more hours. In embodiments of any of the methods described herein, the cell (or the progeny of the cell) is cultured in the presence of the inhibitor of protein degradation for at least 1, 2, 3, 4, 5, 6, 7, 8, 9, 10, or more passages or for at least 12, 24, 48, 72 hours. In embodiments of any of the methods described herein, the cell is contacted by the inhibitor of protein degradation for 24, 48, 72, 96, or 168 hours after a selection step, e.g., MSX selection. In embodiments of any of the methods described herein, the cell is contacted by the inhibitor of protein degradation for 24, 48, 72, 96, or 168 hours prior to a selection step, e.g., MSX selection. In embodiments of any of the methods described herein, the cell is contacted by the inhibitor of protein degradation simultaneously or concurrently with a selection step, e.g., MSX selection.

Cells

In some embodiments of any of the methods or compositions described herein, the method comprises providing a cell that expresses the polypeptide, e.g., the recombinant polypeptide, e.g., a cell that comprises an exogenous nucleic acid that encodes the product, e.g., the polypeptide, e.g., the recombinant polypeptide or controls the expression of the polypeptide, e.g., the recombinant polypeptide.

In embodiments of any of the methods or compositions described herein, the cell comprises an exogenous nucleic acid that encodes the product, e.g., the polypeptide, e.g., the recombinant polypeptide or controls, e.g., increases, the expression of the polypeptide, e.g., the recombinant polypeptide. In embodiments, the exogenous nucleic acid comprises a nucleic acid sequence encoding one or more, e.g., two, recombinant polypeptides. In one embodiment, the cell is of a type that that has been used commercially to produce a polypeptide product, that has been used to produce a polypeptide for pre-clinical work, or a cell that has been used to produce a product, e.g., a polypeptide, for a clinical trial. In one embodiment, the cell expresses a polypeptide, e.g., the recombinant polypeptide, is selected from Table 1 or 2.

In embodiments of any of the methods or compositions described herein, the cell is a eukaryotic cell. In one embodiment, the cell is a mammalian cell. In one embodiment, the cell is from mouse, rat, Chinese hamster, Syrian hamster, monkey, ape (e.g., including human), dog, horse, camel, ferret, or cat. In one embodiment, the cell is a CHO cell, e.g., CHOK1, CHOK1SV, Potelligent CHOK1SV, CHO GS knockout, CHOK1SV GS-KO, CHOS, CHO DG44, CHO DXB11, CHOZN, or a CHO-derived cell. In one embodiment, the cell is a selected from HeLa, HEK293, H9, HepG2, MCF7, Jurkat, NIH3T3, PC12, PER.C6, BHK, VERO, SP2/0, NS0, YB2/0, EB66, C127, L cell, COS, e.g., COS1 and COS7, QC1-3, CHOK1, CHOK1SV, Potelligent CHOK1SV, CHO GS knockout, CHOK1SV GS-KO, CHOS, CHO DG44, CHO DXB11, and CHOZN.

In embodiments of any of the methods or compositions described herein, the cell is a eukaryotic cell other than a mammalian cell. In one embodiment, the cell is from an insect, plant, duck, parrot, fish, yeast, or fungus.

Products

As described herein, the products produced by the cells and methods of the present disclosure can be a molecule, a nucleic acid, a polypeptide, or any fusion or hybrid thereof. In one embodiment, the product is a non-naturally occurring material or molecule. In another embodiment, the product is a naturally occurring material or molecule. The cells producing the products described herein are engineered or modified to control, e.g., increase the expression, or produce, e.g., encode, the products described herein. In one embodiment, the cells are engineered or modified to comprise an exogenous nucleic acid that controls, e.g., increases, the expression of an endogenously expressed product. In another embodiment, the cells are engineered or modified to comprise an exogenous nucleic acid that encodes a product, e.g., an endogenously expressed product, a product that is not endogenously produced by the cell, or a non-naturally occurring product.

In one embodiment, the product, e.g., the polypeptide, e.g., the recombinant polypeptide, is a therapeutic polypeptide, e.g., for administration to subject having a disease or disorder. In one embodiment, the product, e.g., the polypeptide, e.g., the recombinant polypeptide is a diagnostic polypeptide.

In any of the methods or compositions disclosed herein, the product comprises one or more of antibody molecule, a bispecific molecule, a blood clotting factor, an anticoagulant, a hormone, an interferon, an interleukin, or an enzyme.

In one embodiment, the product comprises an antibody molecule, e.g., a full-length antibody or an antibody fragment. In one embodiment, the product comprises an antibody molecule or fragment thereof coupled to, e.g., covalently or non-covalently, a second agent, e.g., a polypeptide, e.g., a toxin. In one embodiment, the antibody molecule is a monoclonal antibody. In one embodiment, the antibody molecule binds to a tumor or cancer-associated antigen. In one embodiment, the antibody molecule binds to tumor associated glycoprotein (TAG72). In one embodiment, the product comprises a bispecific molecule, e.g., provided in Table 2.

In one embodiment, the product, e.g., polypeptide, e.g., a recombinant polypeptide, is a human polypeptide which does not differ in amino acid sequence from a naturally occurring isoform of the human polypeptide.

In another embodiment, the product, e.g., polypeptide, e.g., a recombinant polypeptide, differs from a naturally occurring isoform of the human polypeptide by no more than 1, 2, 3, 4, 5, 10, 15 or 20 amino acid residues.

In yet another embodiment, the product, e.g., polypeptide, e.g., a recombinant polypeptide, differs from a naturally occurring isoform of the human polypeptide or protein by no more than 1, 2, 3, 4, 5, 6, 7, 8, 9, 10, or 15% of its amino acid residues.

In any of the methods or compositions disclosed herein, the product comprises a polypeptide, e.g., a recombinant polypeptide, selected from Table 1 or Table 2. In one embodiment, the product, e.g., polypeptide, e.g., a recombinant polypeptide, is a polypeptide from Table 1 or Table 2.

In another embodiment, the product, e.g., polypeptide, e.g., a recombinant polypeptide, differs from a polypeptide from Table 1 or Table 2 by no more than 1, 2, 3, 4, 5, 10, 15 or 20 amino acid residues.

In yet another embodiment, the product, e.g., polypeptide, e.g., a recombinant polypeptide, differs from a polypeptide from Table 1 or Table 2 by no more than 1, 2, 3, 4, 5, 6, 7, 8, 9, 10, or 15% of its amino acid residues.

In any of the methods or compositions described herein, an exogenous nucleic acid comprising a nucleic acid sequence that controls the expression of a product or encodes a product, e.g., a recombinant polypeptide, is introduced to the cell. In any of the methods or compositions described herein, the cell comprises an exogenous nucleic acid comprising a nucleic acid sequence encoding a product, e.g., a recombinant polypeptide. In one embodiment, the exogenous nucleic acid is integrated into a nucleic acid in the cell, e.g., the chromosomal genome of the cell. In another embodiment, the exogenous nucleic acid is not integrated into the chromosomal genome of the cell, but is integrated on an artificial chromosome or plasmid, e.g., such that the exogenous nucleic acid is maintained in the cell or progeny of the cell.

In any of the methods or compositions described herein, the exogenous nucleic acid may further comprise one or more, e.g., two, three, four, or five, additional nucleic acid sequences, e.g., encoding products or other sequences or polypeptides for controlling the expression of a product.

In any of the methods or compositions described herein, the exogenous nucleic acid comprises a plasmid or a vector, e.g., an expression or viral vector. In one embodiment, the exogenous nucleic acid comprises a glutamine synthetase (GS) expression vector. In one embodiment, the exogenous nucleic acid further comprises a nucleic acid sequence encoding a selection marker. In one embodiment, the selection marker comprises glutamine synthetase, DHFR, or a gene that confers antibiotic resistance. In one embodiment, the nucleic acid sequence encoding the selection marker is operably linked to a first promoter and the nucleic acid sequence encoding the product, e.g., the polypeptide, e.g., the recombinant polypeptide is operably linked to a second promoter. In one embodiment, the first promoter and the second promoter are different. In one embodiment, the promoter operably linked to the selection marker is a weak promoter, e.g., SV40E promoter. In one embodiment, the promoter operably linked to the nucleic acid sequence encoding the polypeptide, e.g., the recombinant polypeptide is a strong promoter, e.g., a CMV promoter, e.g., hCMV-MIE promoter.

In any of the methods described herein, the method comprises expressing the product, e.g., polypeptide, e.g., recombinant polypeptide, from the cell or a progeny cell. In one embodiment, the product, e.g., polypeptide, e.g., recombinant polypeptide, is secreted from the cell or progeny cell, e.g., into the culture medium.

In any of the methods or compositions described herein, the expressed product, e.g., polypeptide, e.g., recombinant polypeptide, is evaluated for a parameter related to a physical or functional property, e.g., primary sequence, glycosylation, primary, secondary, tertiary, or quaternary structure, activity, degree of glycosylation, degree of aggregation, proportion or level of the expressed protein having a preselected property, e.g., having a preselected monomeric, dimeric, or trimeric structure, or the level or proportion of the expressed polypeptide having a preselected structure, e.g., non-denatured or non-aggregated structure. In embodiments, the method comprises providing a value for the parameter. In embodiments, the method comprises comparing a value for the parameter with a reference value.

In embodiments of any of the methods or compositions described herein, the value for the effect of the inhibitor of protein degradation, e.g., proteasome inhibitor, on the parameter related to cell function exceeds the reference value by 5%, 10%, 20%, 30%, 40%, 50%, 60%, 70%, 80%, 90%, 100% or more. In embodiments the value for the effect of the inhibitor of protein degradation, e.g., proteasome inhibitor, on the parameter related to cell function exceeds the reference value by 1-fold, 2-fold, 3-fold, 4-fold, 5-fold, 6-fold, 7-fold, or 8-fold or more. In embodiments, the reference value is the value of the effect of the inhibitor of protein degradation on a parameter related to cell function of a reference cell or the value of the parameter related to cell function of the cell that has not been contacted with the inhibitor of protein degradation. In embodiments, the parameter comprises the ability to produce a product, e.g., a polypeptide, e.g., a recombinant polypeptide, e.g., a recombinant polypeptide expressed from an exogenous nucleic acid. In embodiments, the parameter comprises the ability to produce a product, e.g., a polypeptide, e.g., a recombinant polypeptide, and wherein the increase is determined by measuring or quantifying the product, e.g., the polypeptide, e.g., the recombinant polypeptide, in the cell or secreted by the cell. In embodiments, the parameter comprises cell survival, and wherein the increase or decrease is determined by measuring or quantifying the number of apoptotic cells. In embodiments, the parameter comprises culture viability, and wherein the increase or decrease is determined by measuring or quantifying the number live cells.

In embodiments where the recombinant polypeptide is secreted from the cell, the methods can include a step for retrieving, collecting, or separating the recombinant polypeptide from the cell, cell population, or the culture medium in which the cell was cultured.

In certain embodiments of any of the preparations described herein, at least 70, 80, 90, 95, 98 or 99%, by weight or number, of the polypeptides in the preparation are properly folded or functionally active.

In certain embodiments of any of the mixtures described herein, the product, e.g. the polypeptide, e.g., the recombinant polypeptide, is present at a higher concentration, e.g., at least, 1%, 2%, 5%, 10%, 20%, 30%, 40%, 50%, 60%, 70%, 80%, 90%, 100% or higher concentration, by weight or number, than would be seen in a cell that has not been contacted with inhibitor of protein degradation; or wherein at least 70, 80, 90, 95, 98 or 99%, by weight or number, of the product, e.g. the polypeptides, e.g., the recombinant polypeptides, in the mixture are properly folded or functionally active.

In certain embodiments of any of the preparations of medium described herein, the product, e.g., the polypeptide, e.g., the recombinant polypeptide, is present at a higher concentration, e.g., at least, 1, 2, 3, 4, 5, 6, 7, 8, 9, 10, 20, or 30% higher concentration, by weight or number, than would be seen in a cell that has not been contacted with an inhibitor of protein degradation; or wherein at least 70, 80, 90, 95, 98 or 99%, by weight or number, of the product e.g., the polypeptides, e.g., the recombinant polypeptides, in the mixture are properly folded or functionally active.

In embodiments, any of the methods described herein can further comprise any of steps (f), (g), or both (f) and (g):

f) culturing the cell, or progeny of the cell, in the absence of the exogenous inhibitor of protein degradation (e.g., for at least 1, 2, 3, 4, 5, 6, 7, 8, 9, 10, or more passages or for at least 12, 24, 48, 72 hours);

g) evaluating the level of recombinant protein produced by the cell, or progeny of the cell, e.g., to obtain a value of recombinant protein produced by the cell or progeny of the cell; and h) optionally, comparing the value obtained in g) with a reference value, wherein the reference value is the level of recombinant protein produced by a cell of the same type as the cell provided in a) cultured in the absence of the exogenous inhibitor of protein degradation.

In embodiments, e.g., embodiments of the methods of making herein, the method further comprises selecting the cell for use in a method of manufacturing a recombinant protein (e.g., a recombinant therapeutic protein). In embodiments, the method further comprises introducing an exogenous nucleic acid into the cell (e.g., after step c), after step d), after step e) or after step f)), optionally, wherein introducing the exogenous nucleic acid comprises transfection, electroporation, or transduction.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIGS. 7A and 7B show the MV151 probe, FIGS. 7C and 7D the MVB003 probe, and FIGS. 7E and 7F the MVB072 probe. The right hand images (FIGS. 7B, 7D, and 7F) show Coomassie blue stained images as loading controls.

FIGS. 8A and 8B show the RUB1001 probe, FIGS. 8C and 8D the RUB1018 probe, and FIGS. 8E and 8F the no probe control. The right hand images (FIGS. 8B, 8D, and 8F) show Coomassie blue stained images as loading controls.

DETAILED DESCRIPTION

Figure 1A:
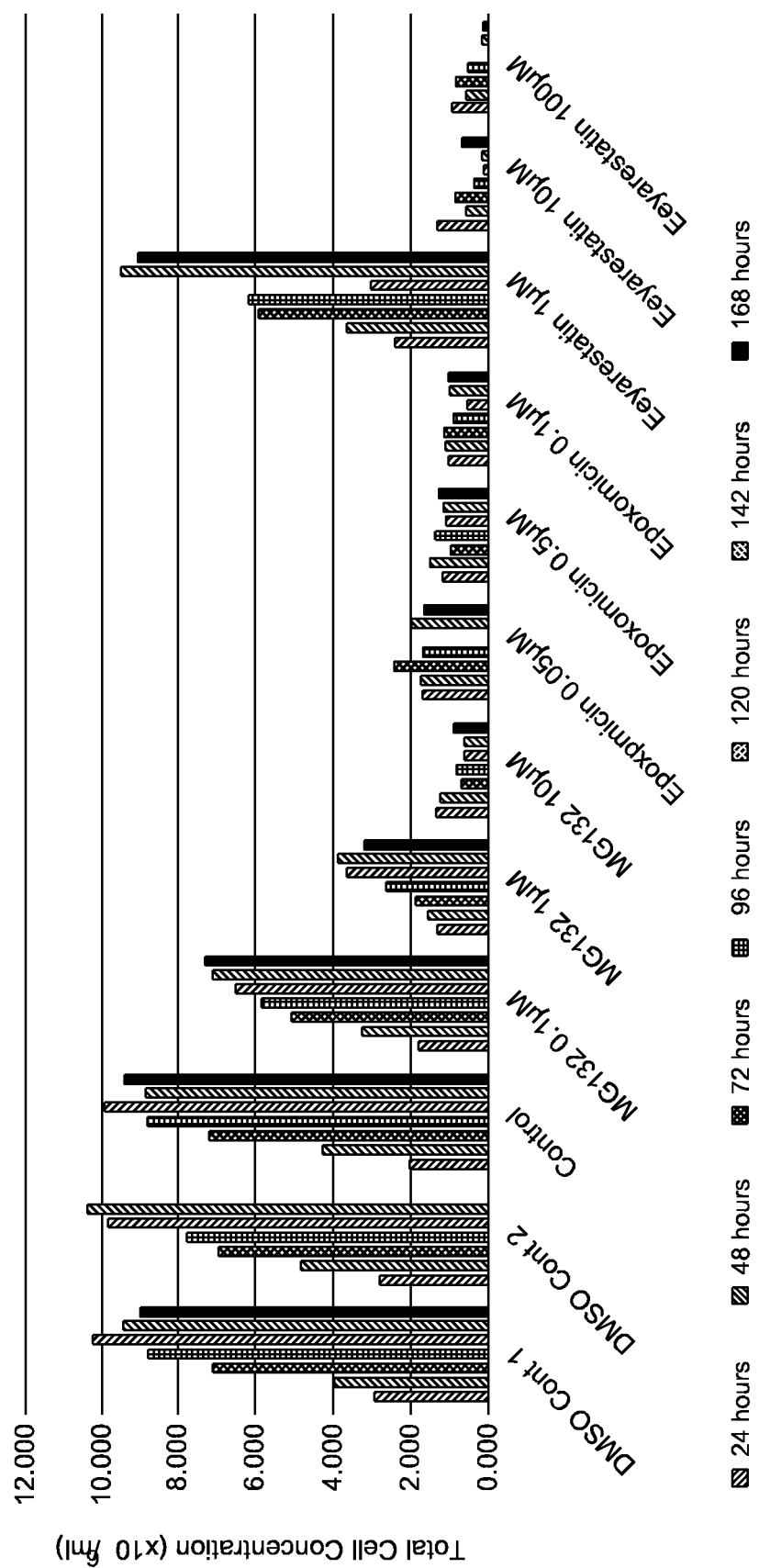
FIGS. 1A-1C are a series of graphs that show the initial assessment of the indicated protein degradation inhibitors at various concentrations on recombinant CHO cell line growth parameters. Samples were taken at the indicated timepoints and cell concentrations together with culture viability were determined on a ViCell instrument (%).
Figure 1B:
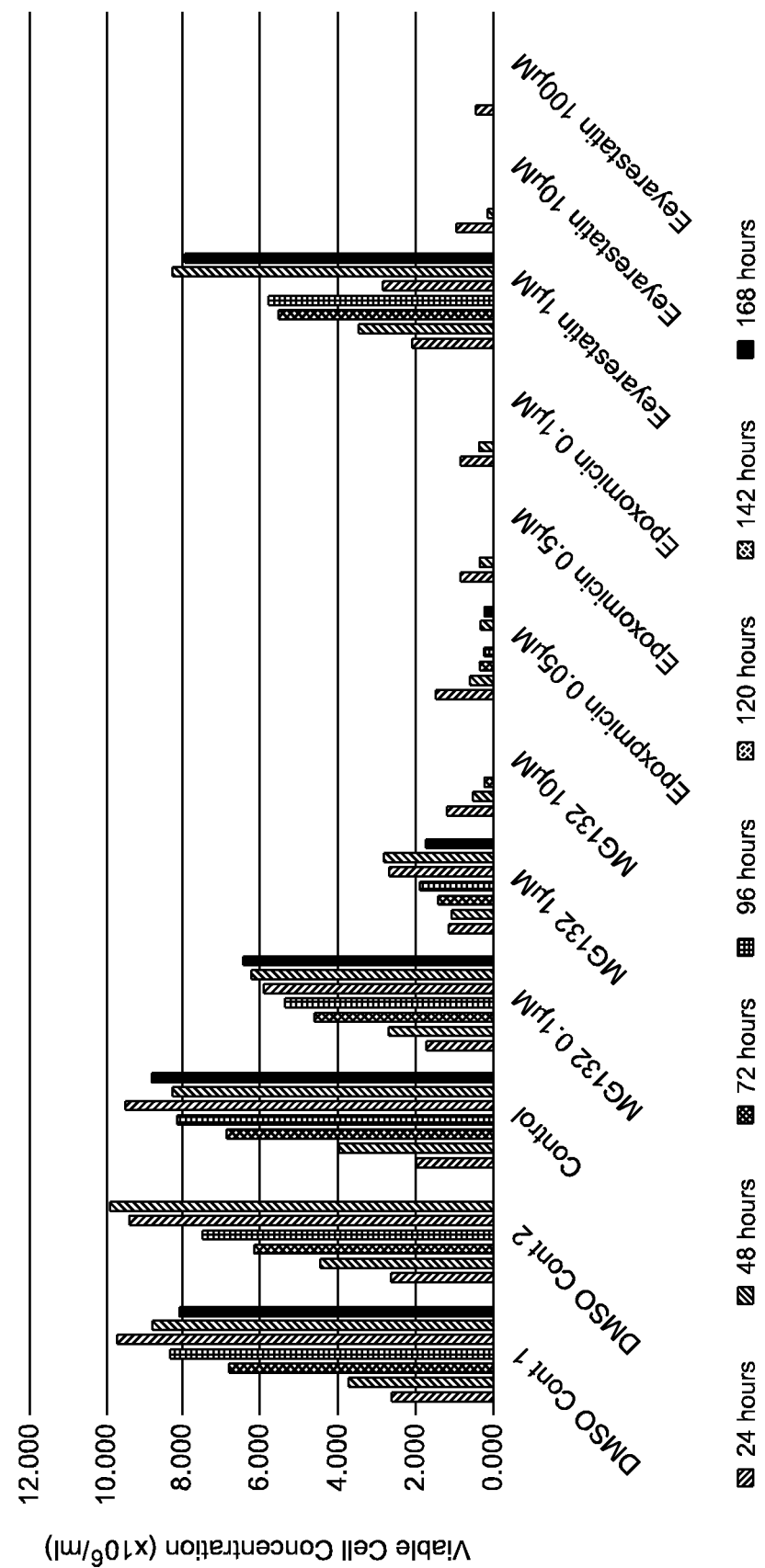
Figure 1C:
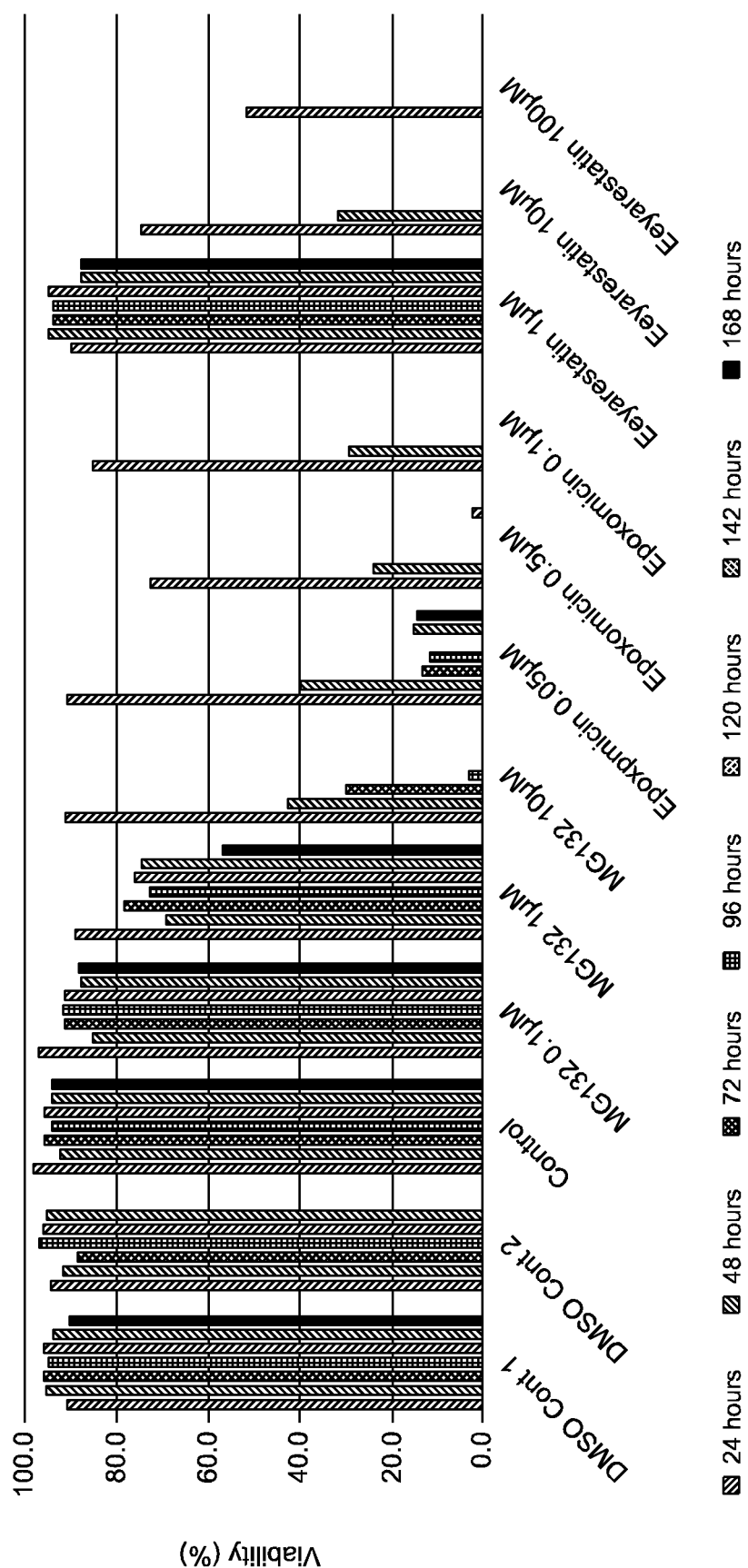
Figure 2A:
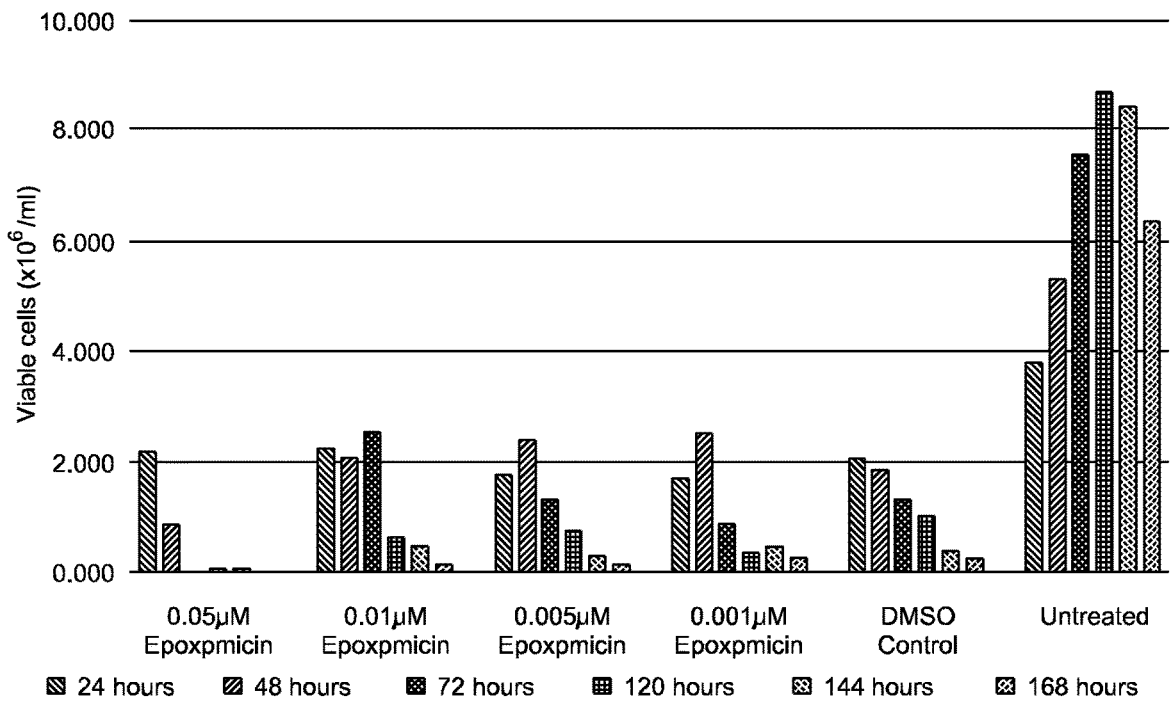
FIGS. 2A-2F are a series of graphs that show further assessment of the indicated protein degradation inhibitors at various concentrations on recombinant CHO cell line growth parameters. Samples were taken at the indicated timepoints and cell concentration together with culture viability was determined on a ViCell instrument (%).
Figure 2B:
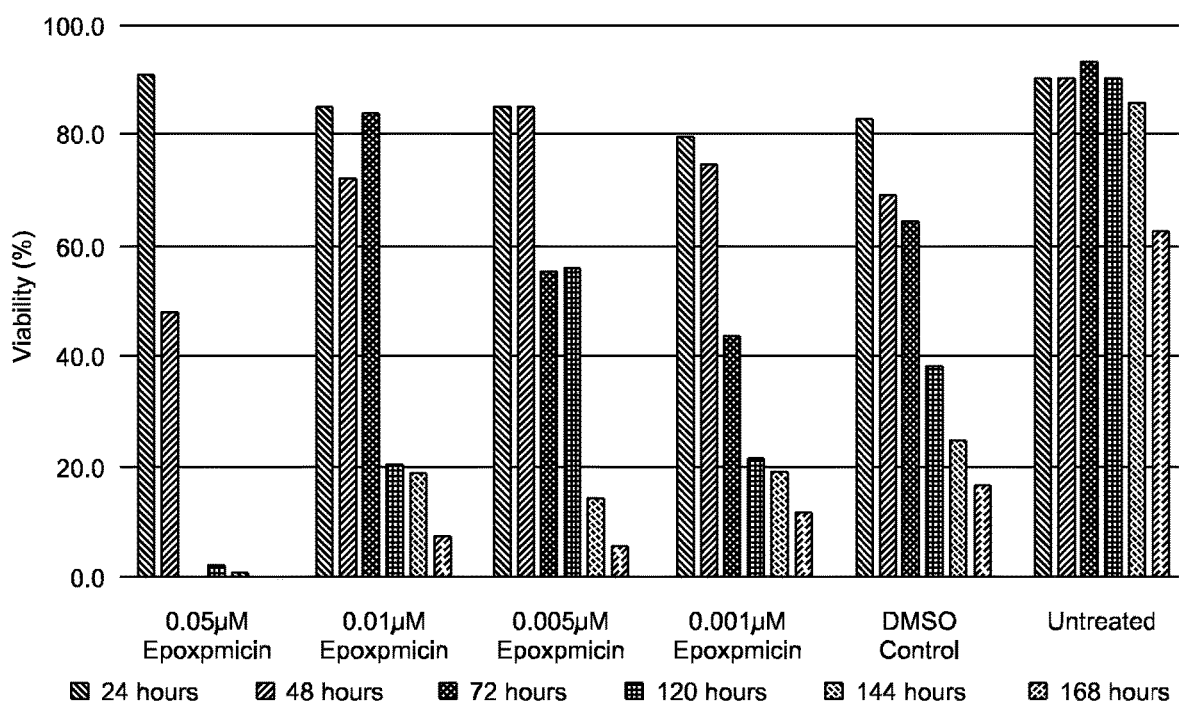
Figure 2C:
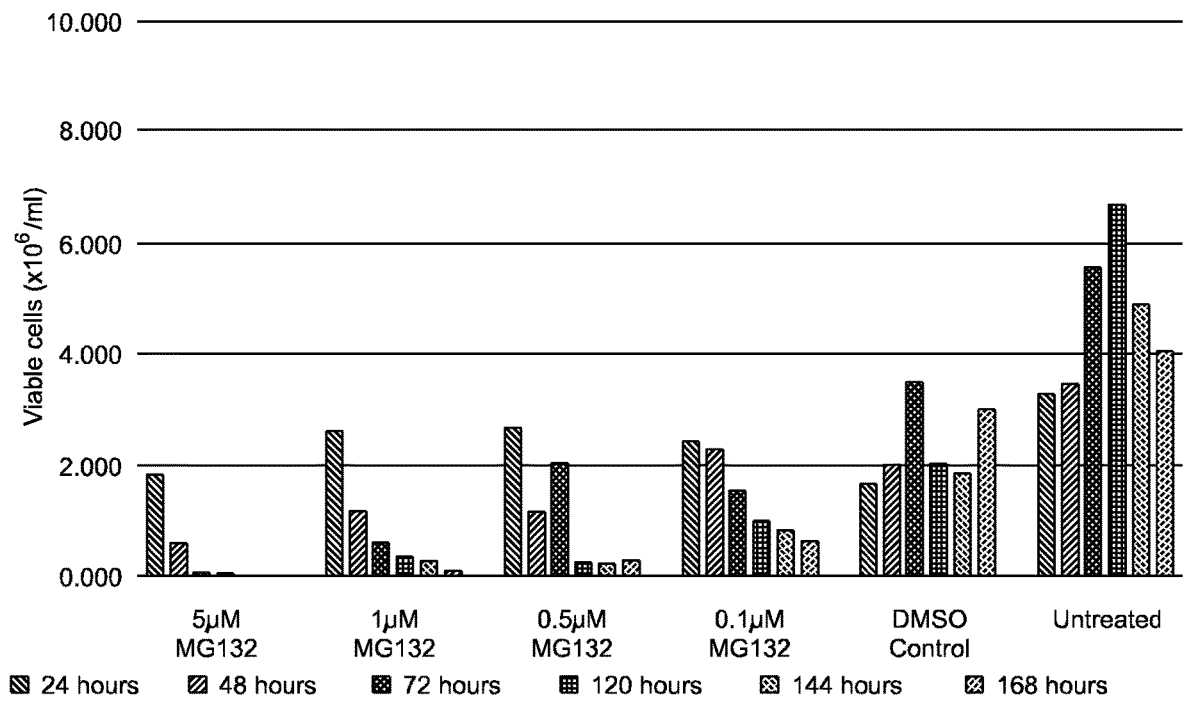
Figure 2D:
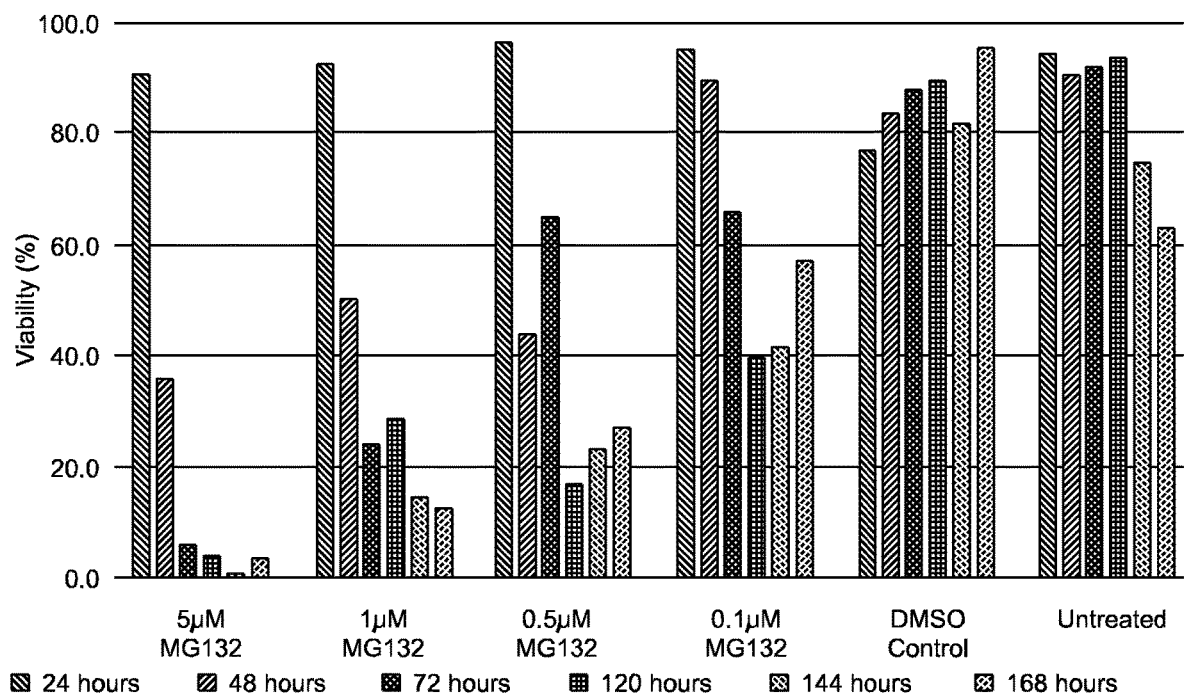
Figure 2E:
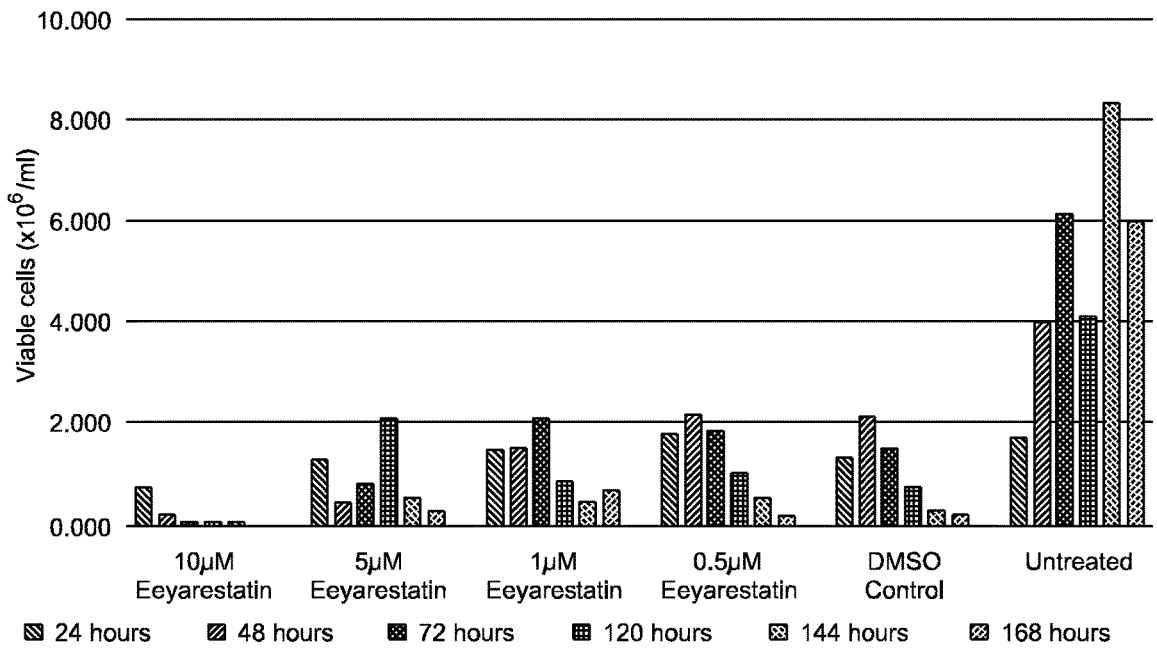
Figure 2F:
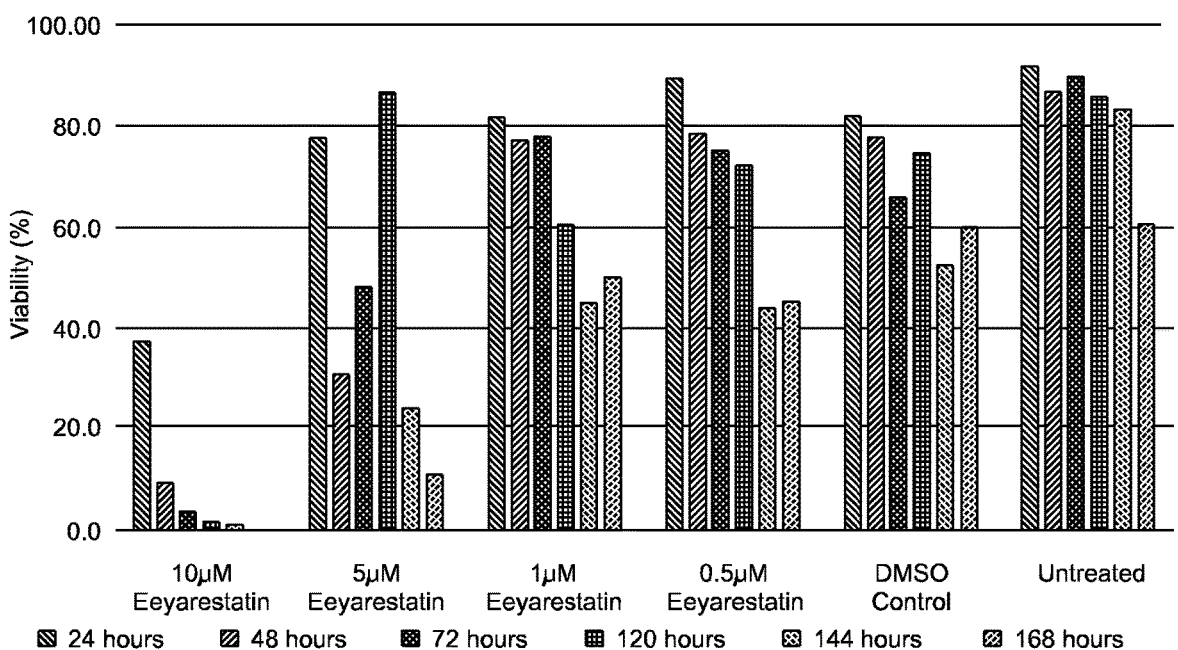
Figure 3A:
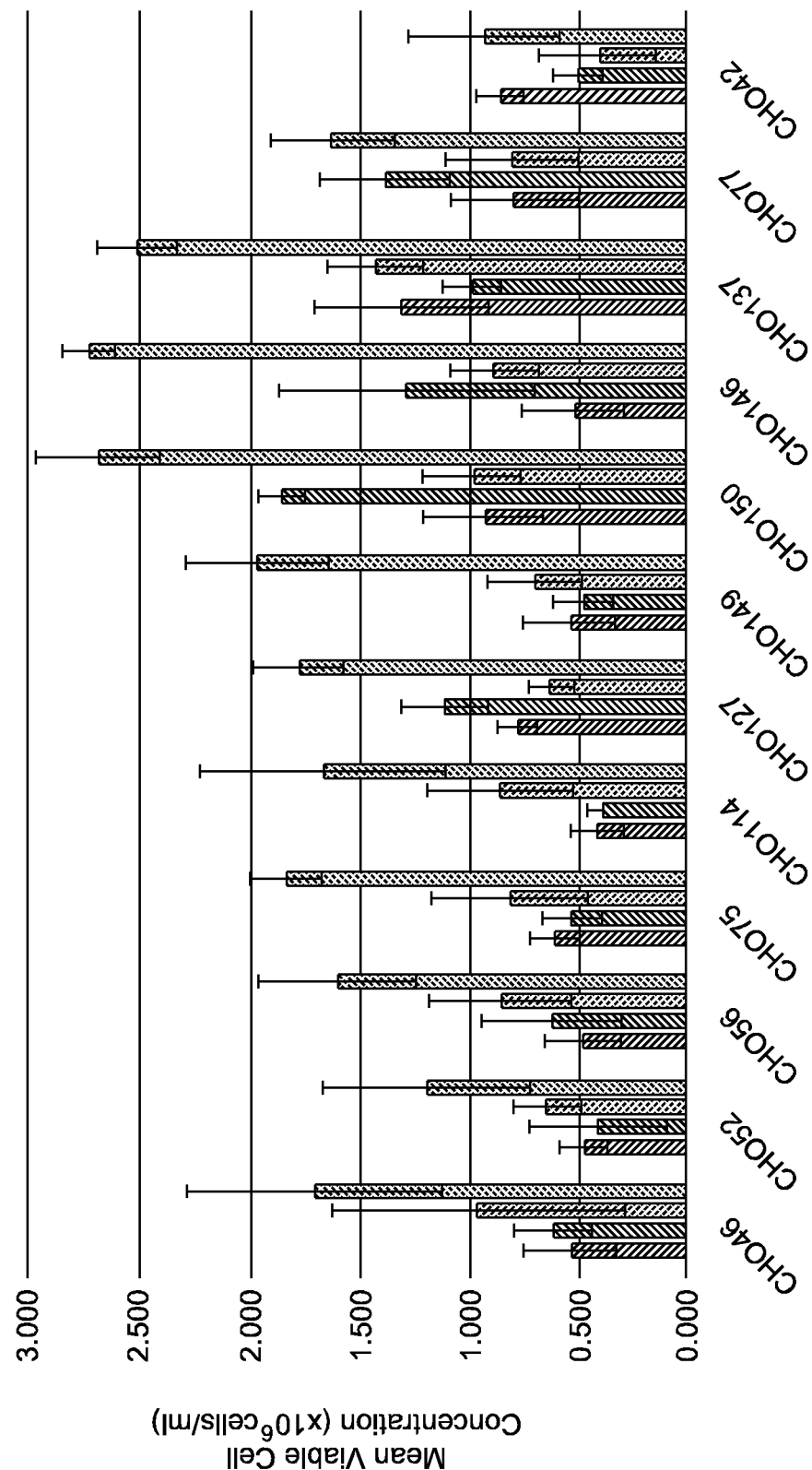
FIGS. 3A-3D are a series of graphs that show the viable cell concentration and culture viability for a panel of CHO antibody producing cell lines when cultured in the presence of MG132. Mean viable cell concentration and culture viability after culturing for 24 and 48 hours in the presence of 0.5 µM MG132 (bars with hatching) or DMSO (bars with dashed hatching). Error bars show the standard deviation of triplicate samples taken at each timepoint.
Figure 3B:
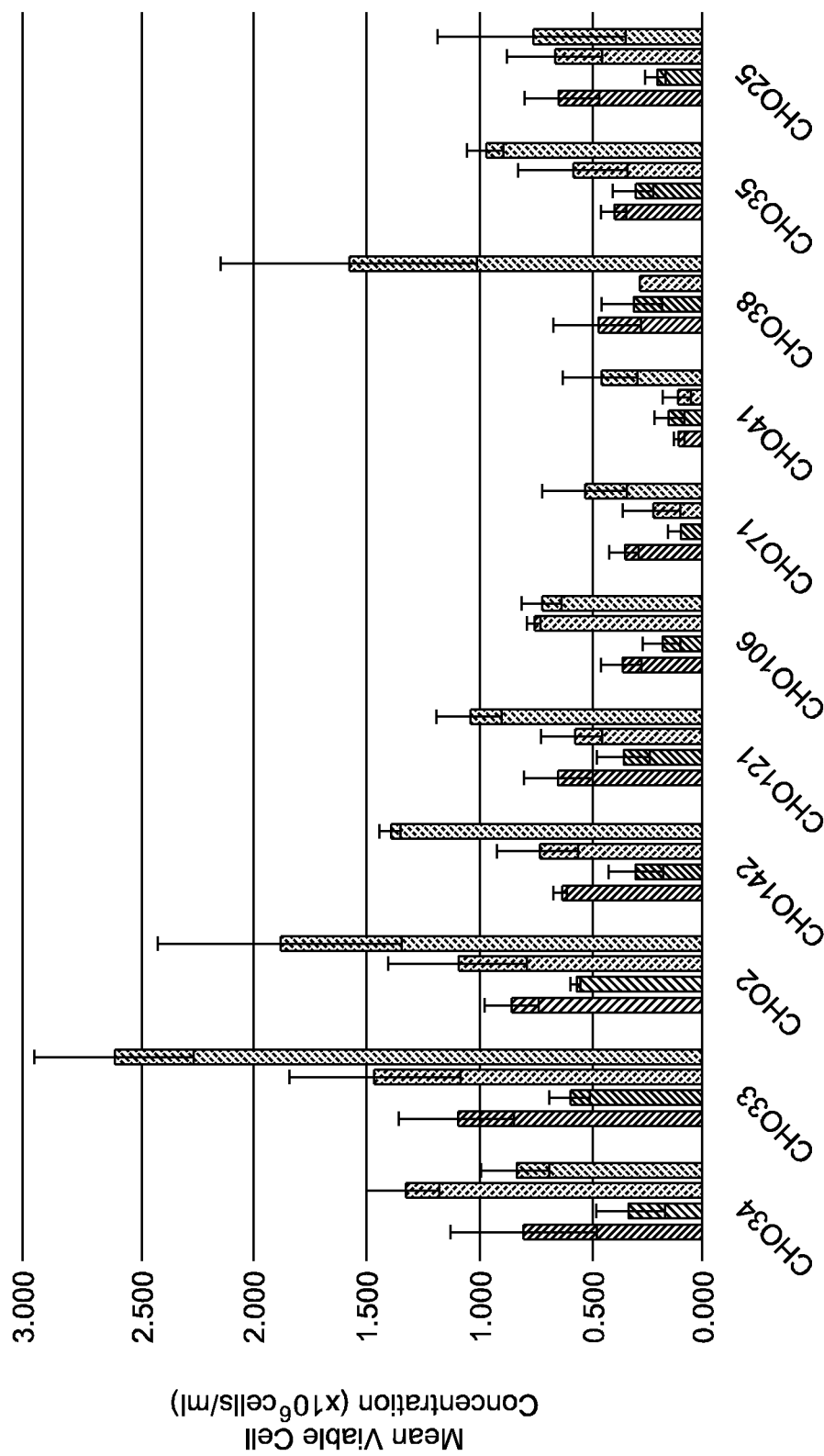
Figure 3C:
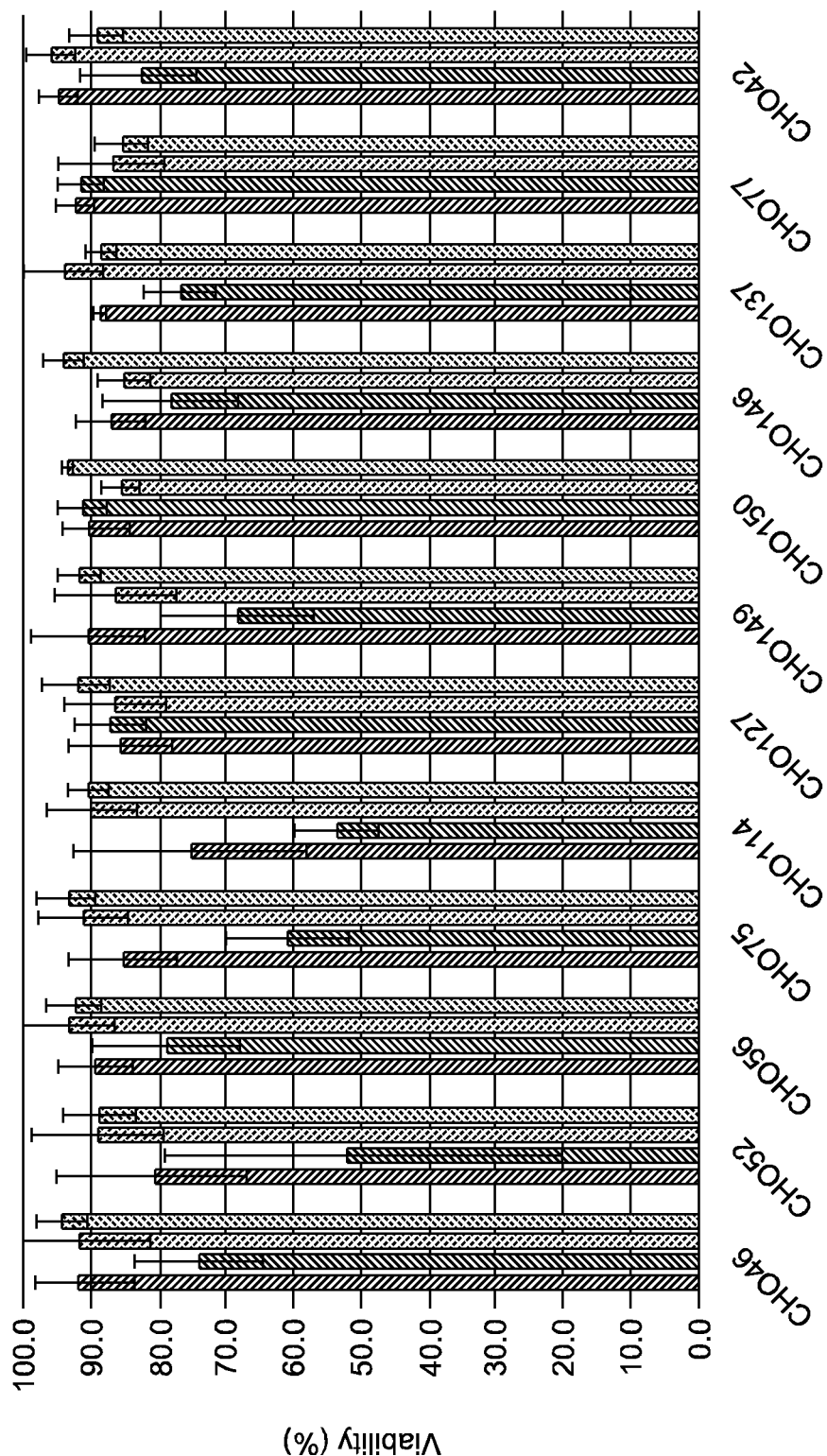
Figure 3D:
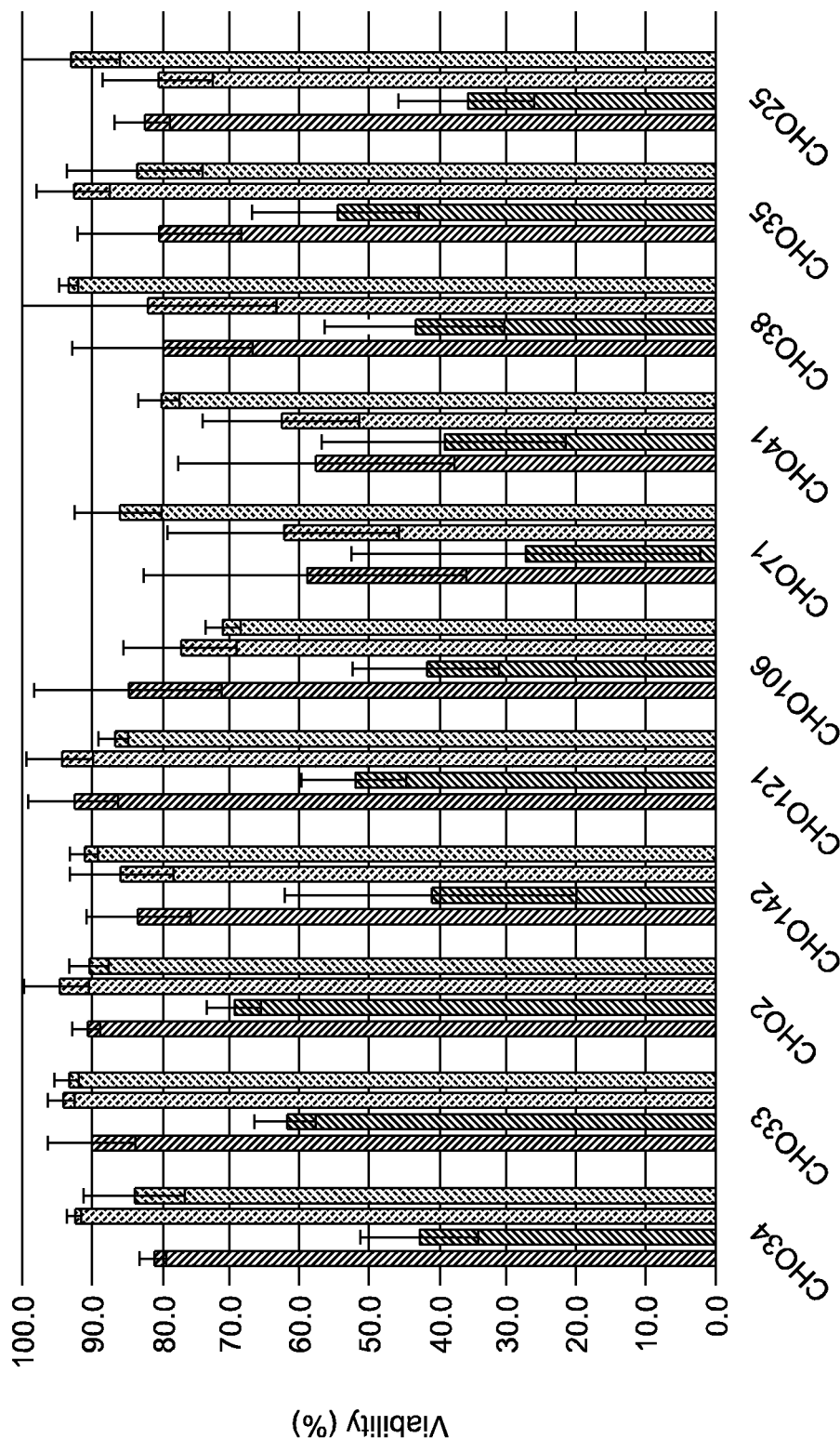
Figure 4A:
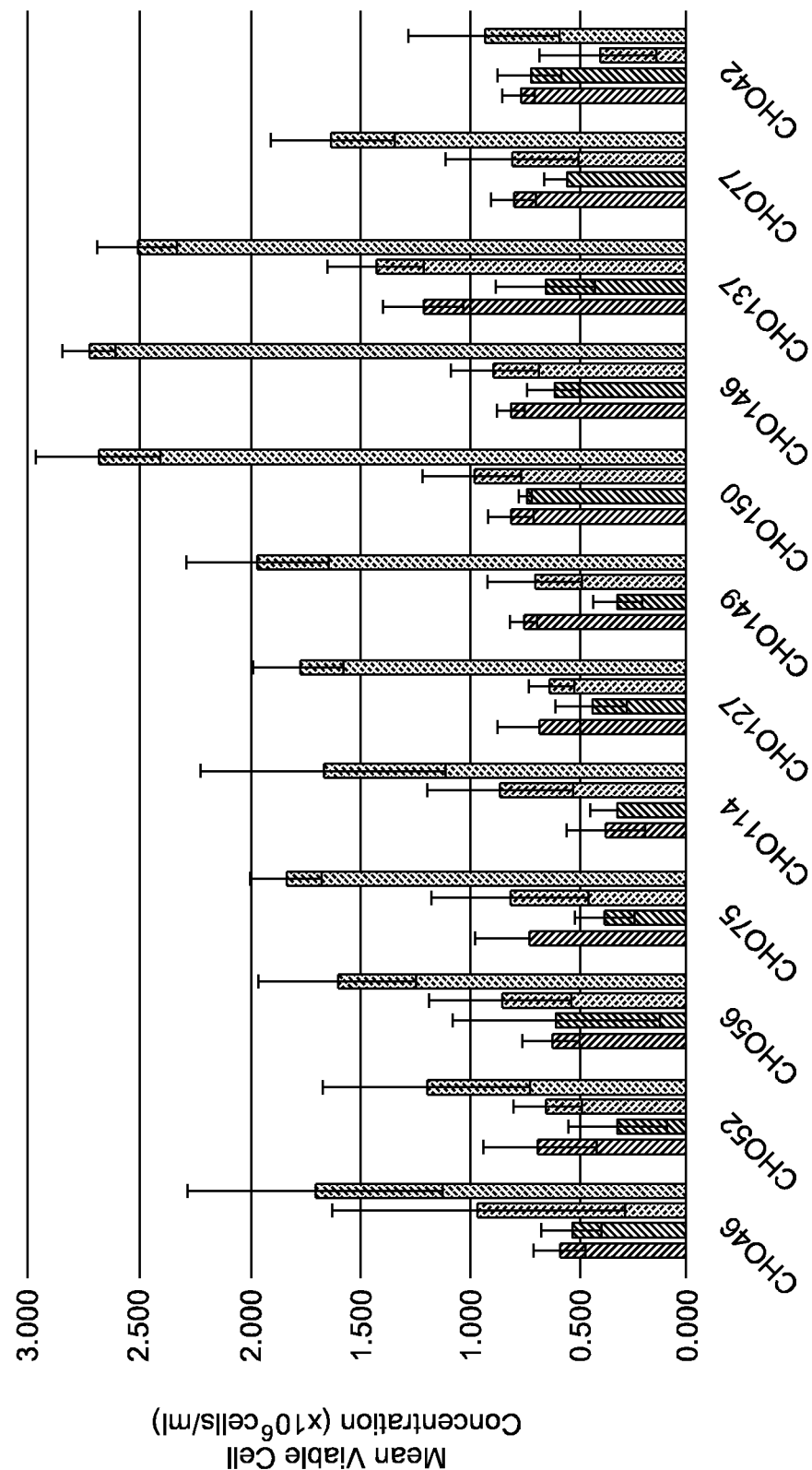
FIGS. 4A-4D are a series of graphs that show the viable culture cell concentration and culture viability for a panel of CHO antibody producing cell lines when cultured in the presence of epoxomicin. Mean viable cell concentration and culture viability after culturing for 24 and 48 hours in the presence of 0.05 µM epoxomicin (bars with hatching) or DMSO (bars with dashed hatching). Error bars show the standard deviation of triplicate samples taken at each timepoint.
Figure 4B:
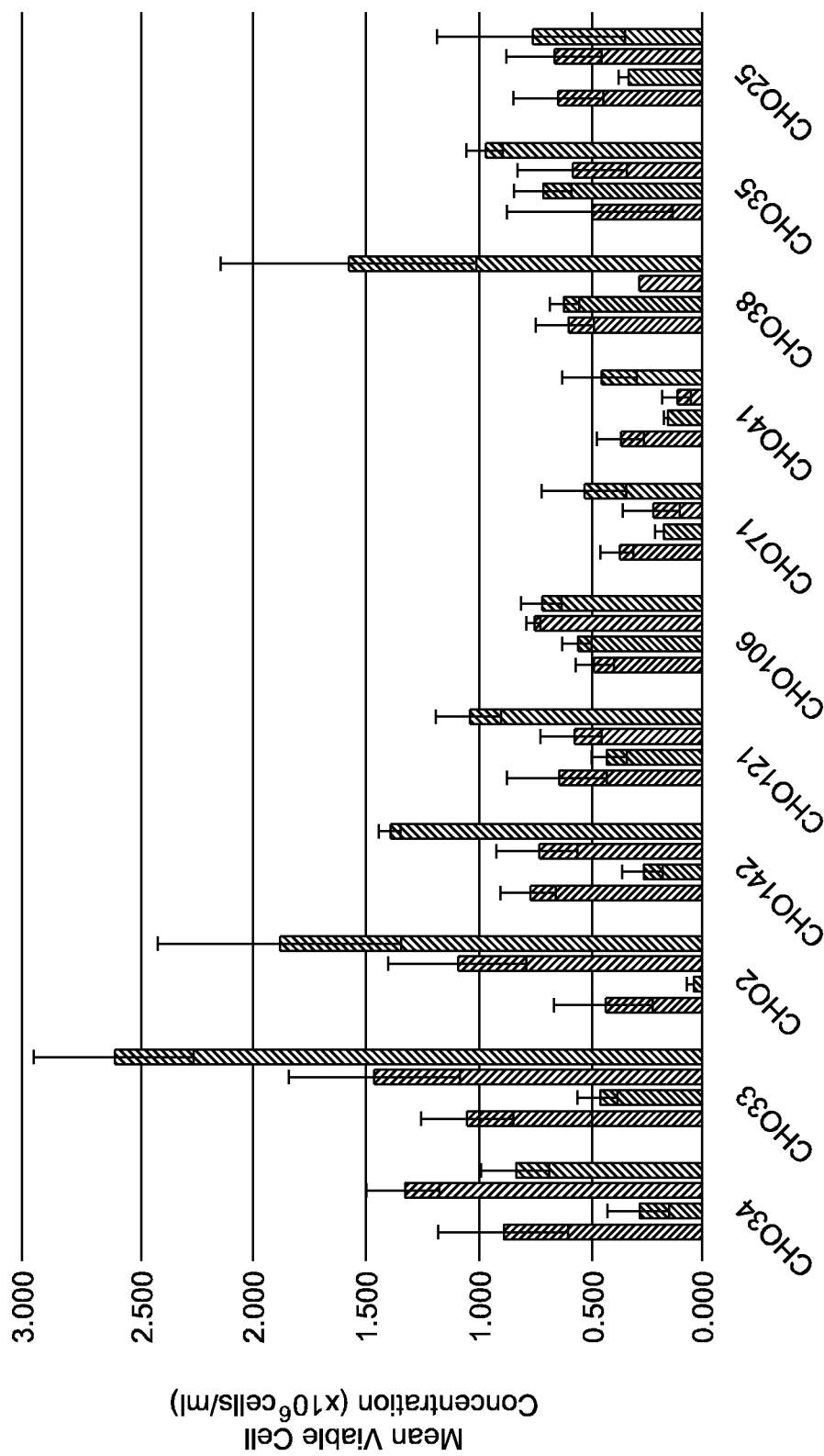
Figure 4C:
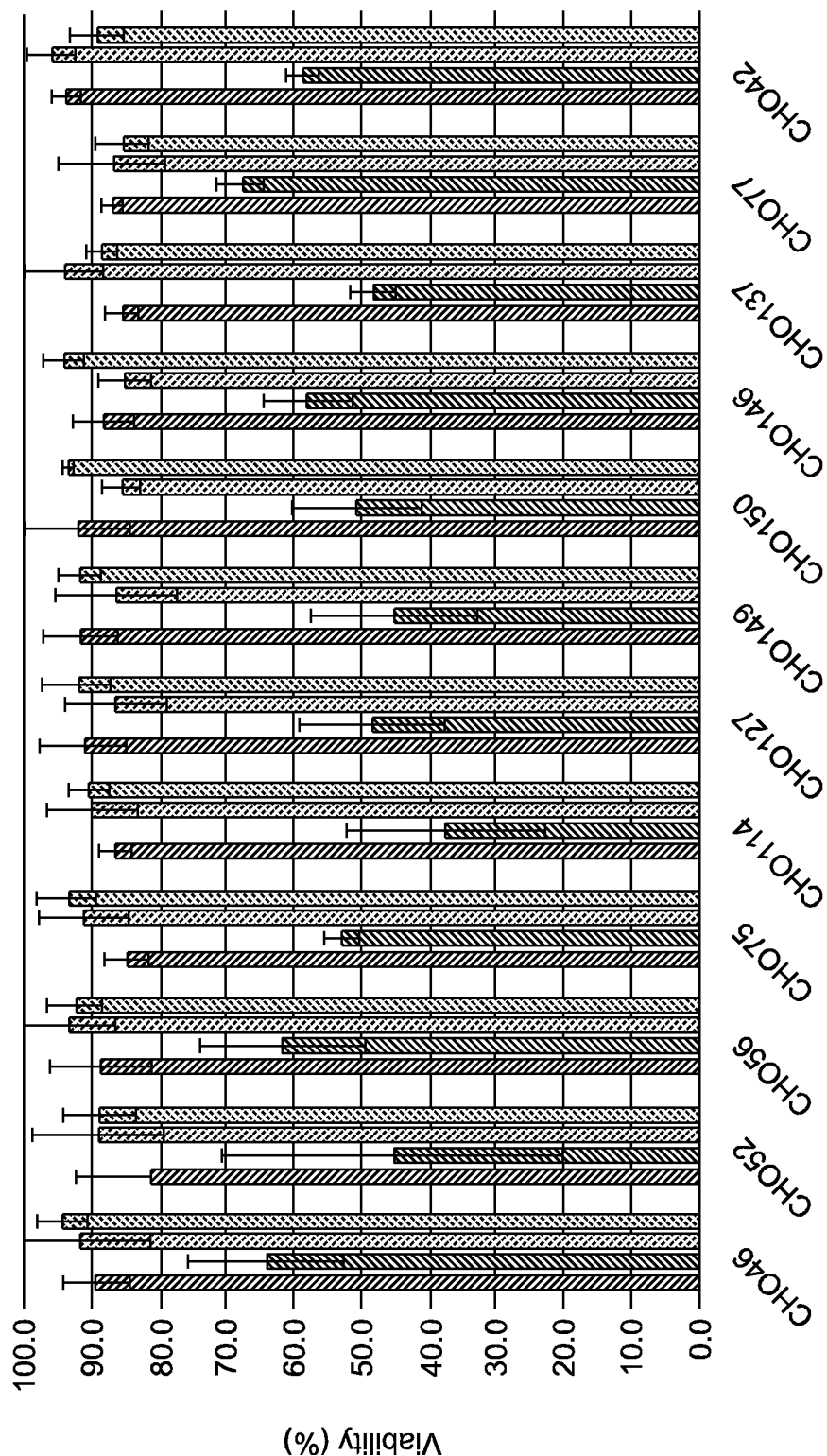
Figure 4D:
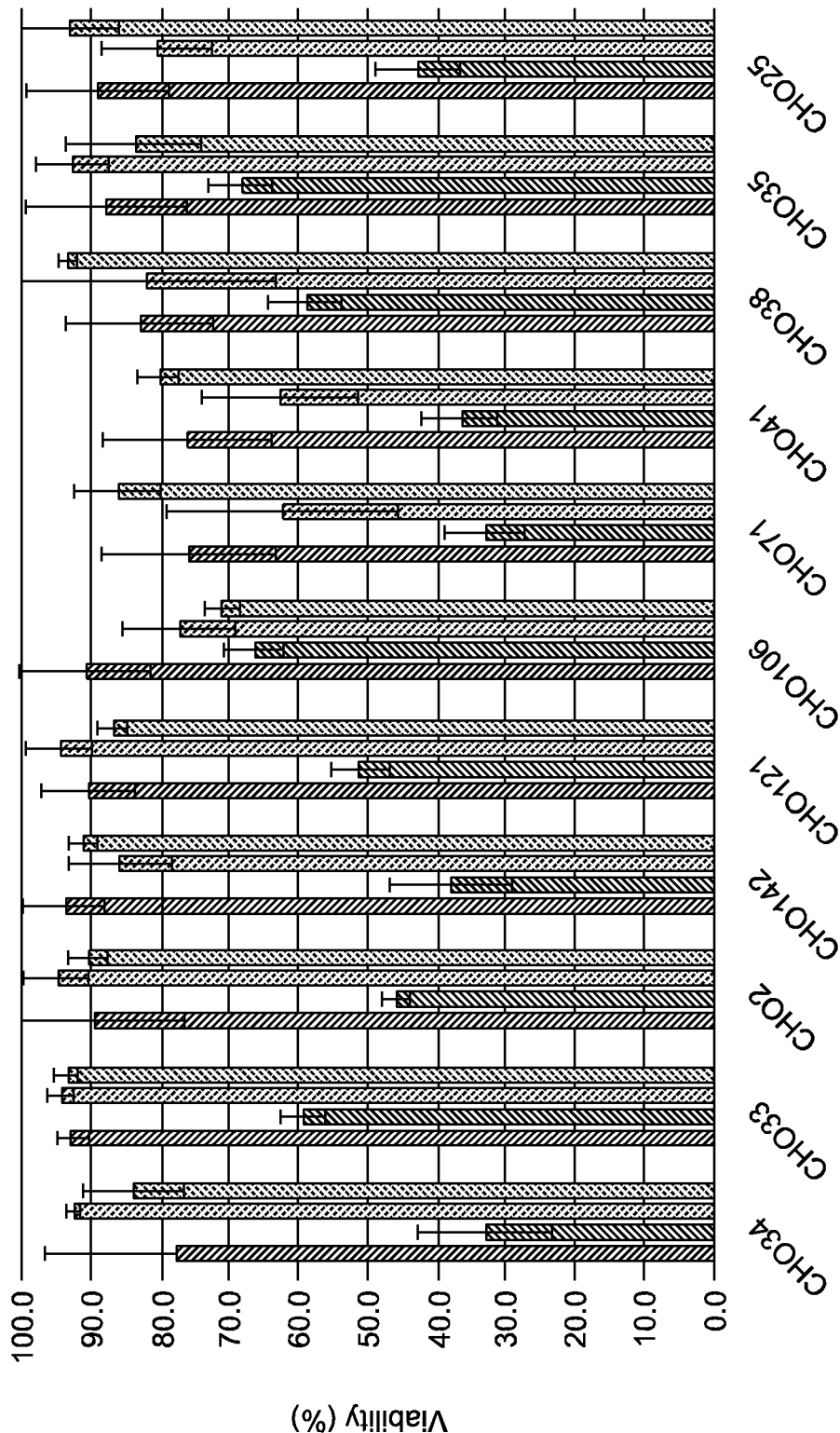
Figure 5A:
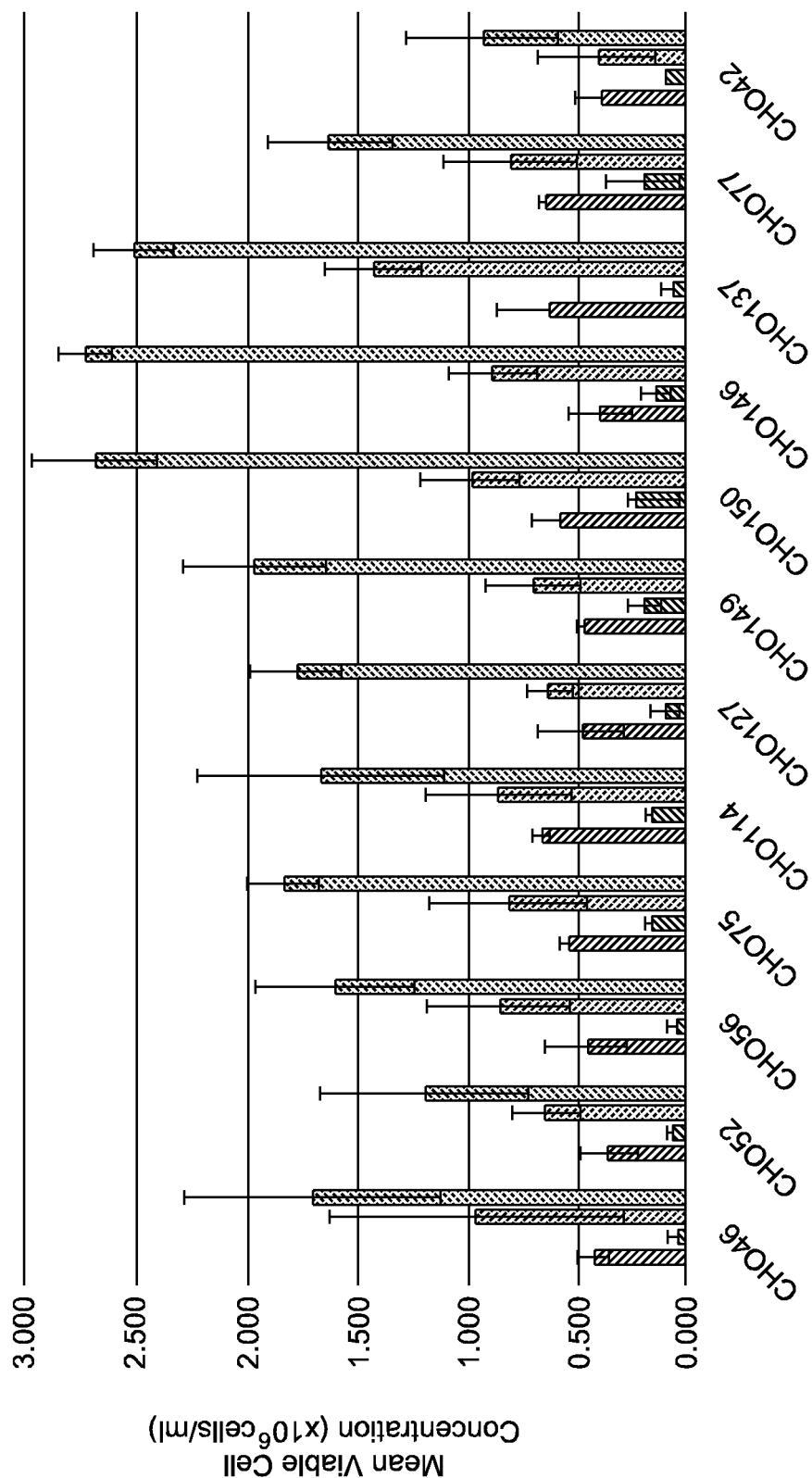
FIGS. 5A-5D are a series of graphs that show the viable cell concentration and culture viability for a panel of CHO antibody producing cell lines when cultured in the presence of eeyarestatin I. Mean viable cell concentration and culture viability after culturing for 24 and 48 hours in the presence of 10 µM eeyarestatin I (bars with hatching) or DMSO (bars with dashed hatching). Error bars show the standard deviation of triplicate samples taken at each timepoint.
Figure 5B:
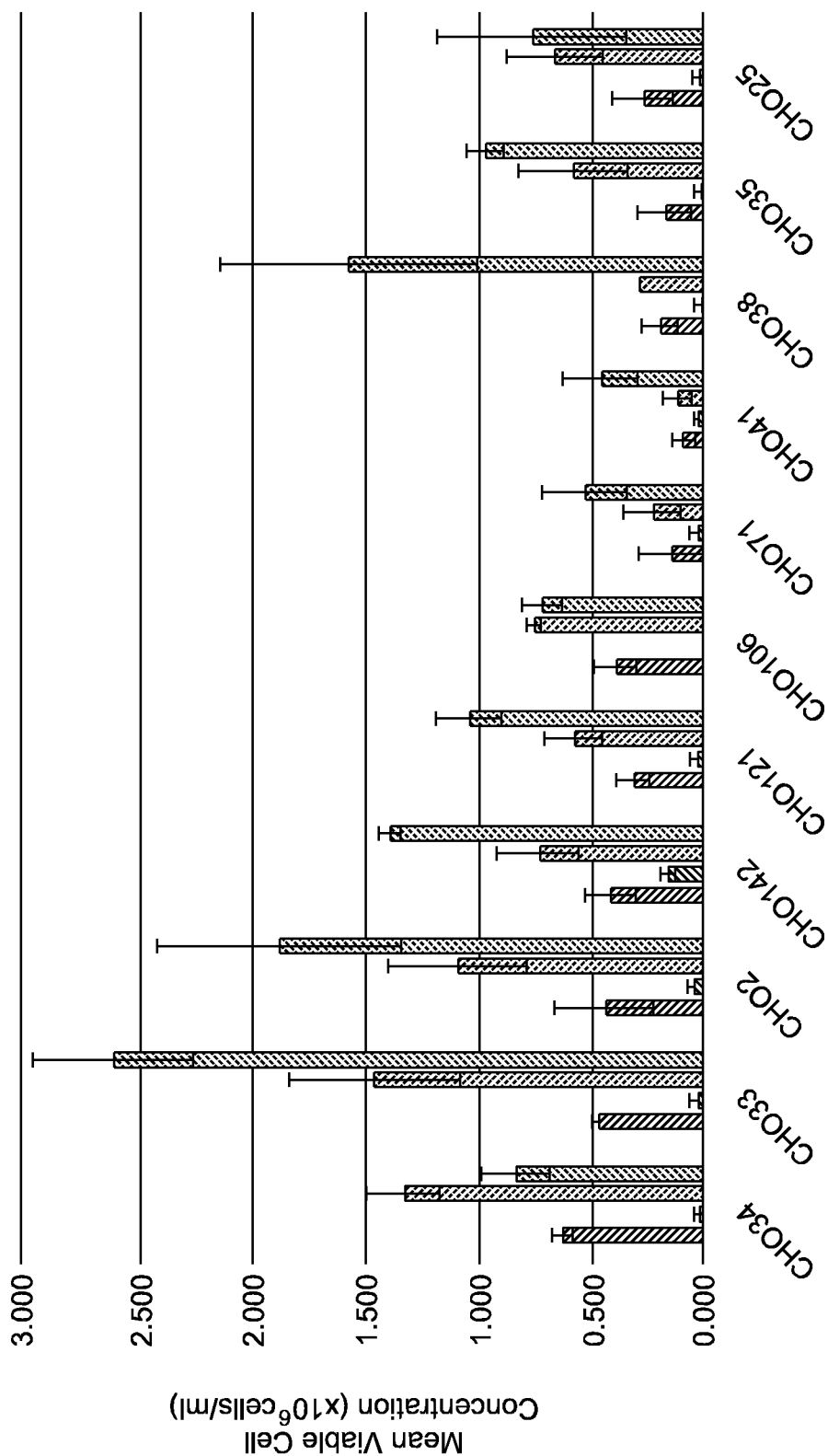
Figure 5C:
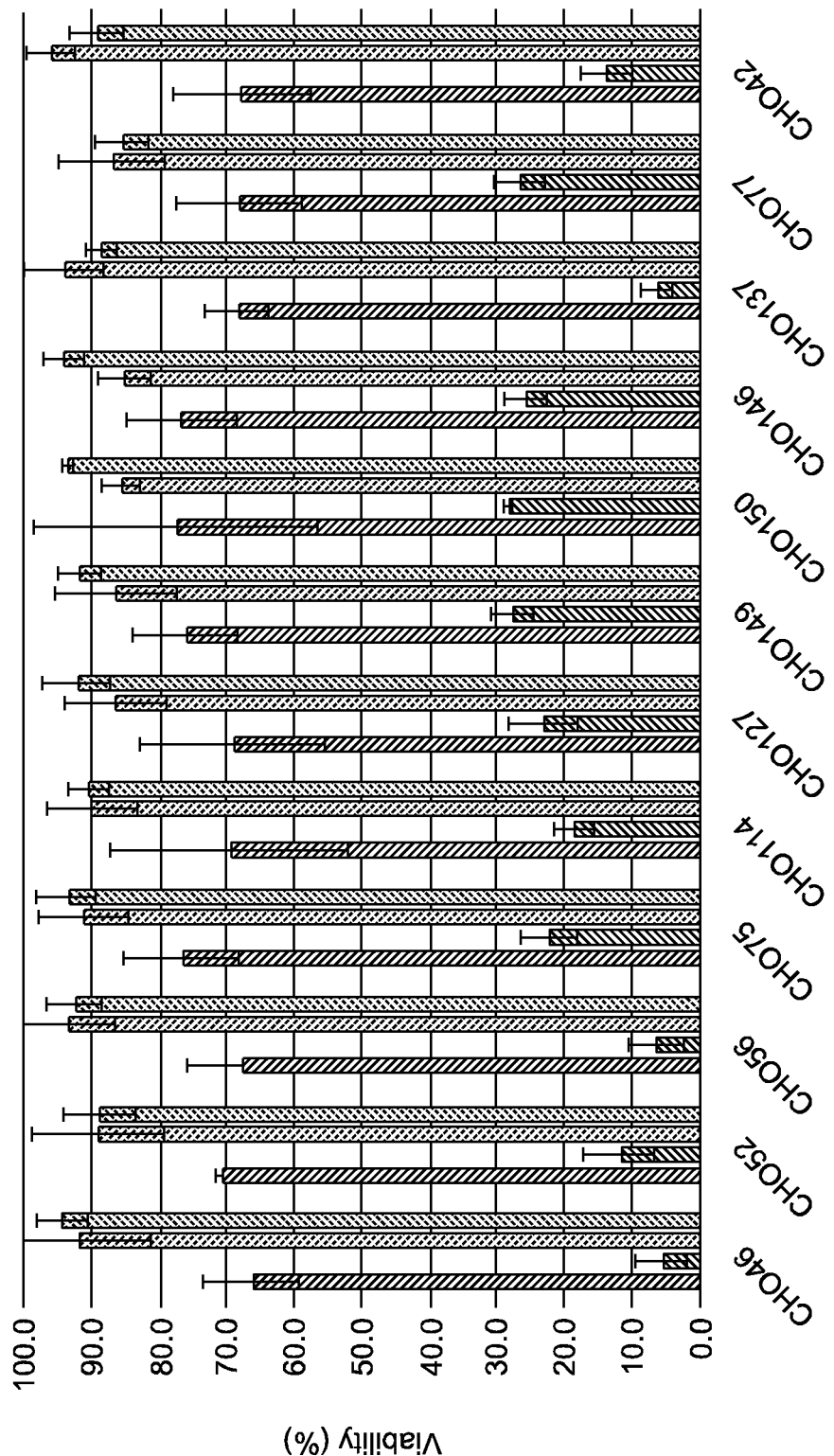
Figure 5D:
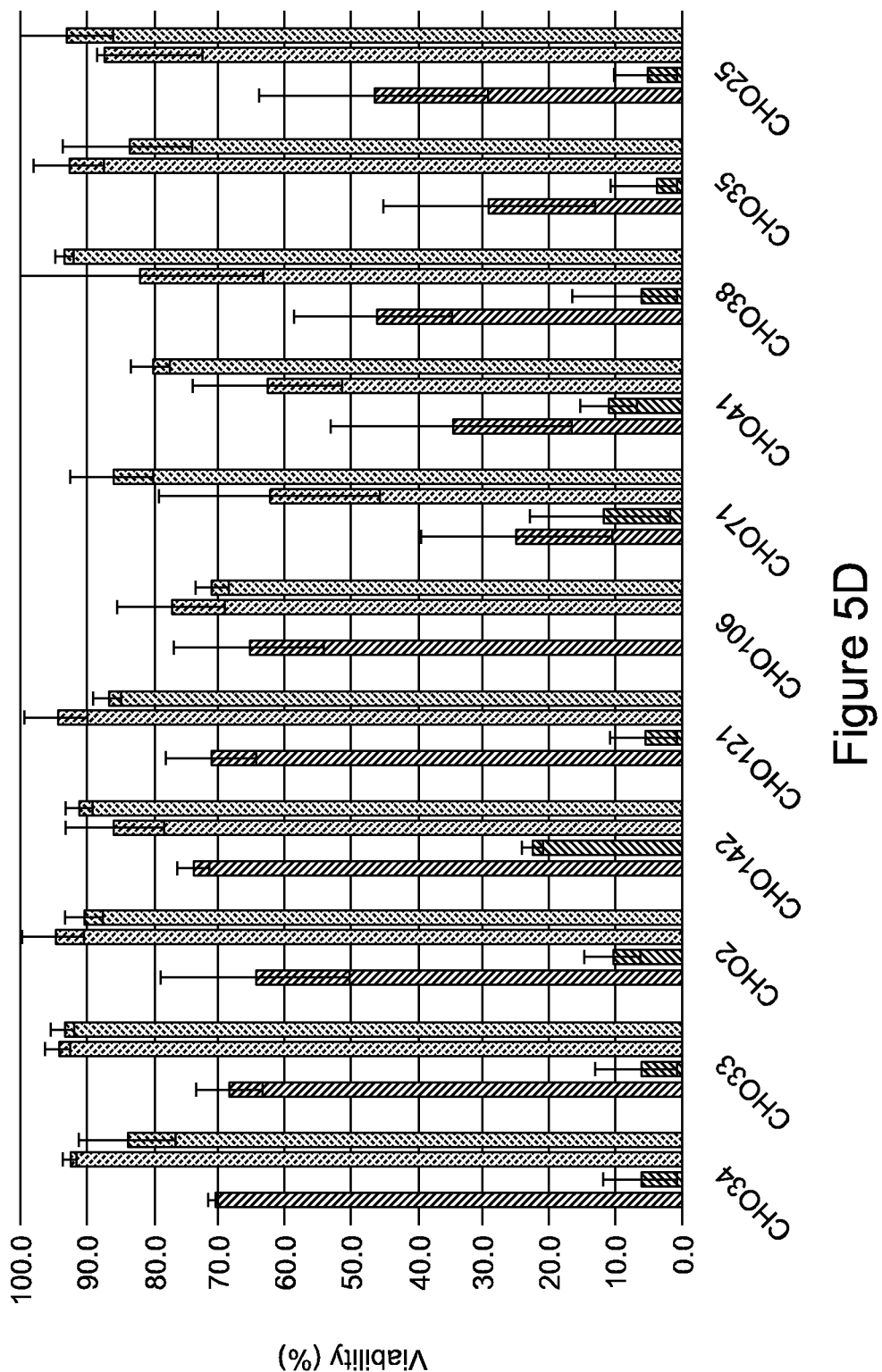
Figure 6B:
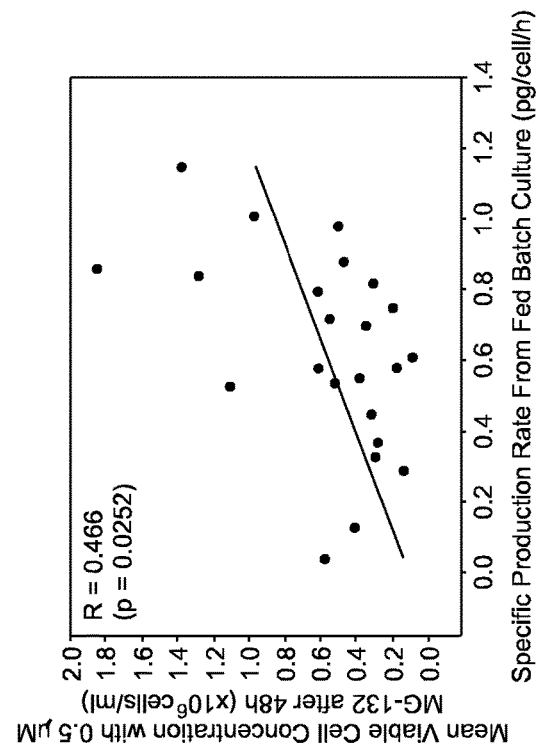
FIGS. 6A-6G are a series of plots that show the correlations between susceptibility (e.g., culture viability and/or viable cell concentration in the presence of inhibitor) to proteasome and ERAD inhibitors and productivity data from fed-batch and bioreactor cultures for the panel of CHO cell lines that produce a monoclonal antibody, at one concentration of the proteasome and ERAD inhibitors. The data was plotted and the best fit line identified by linear regression analysis. The relationship between the parameters was assessed using the Pearson Product Moment Correlation coefficient. The correlations found to be statistically significant ($p<0.05$) are shown.
Figure 6D:
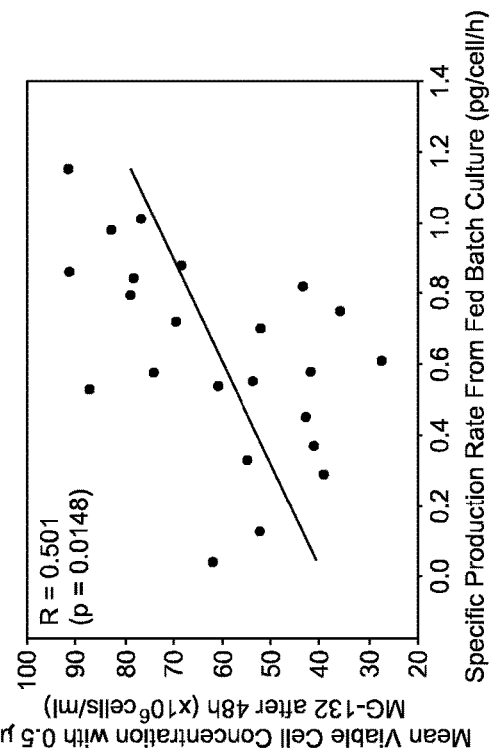
Figure 6A:
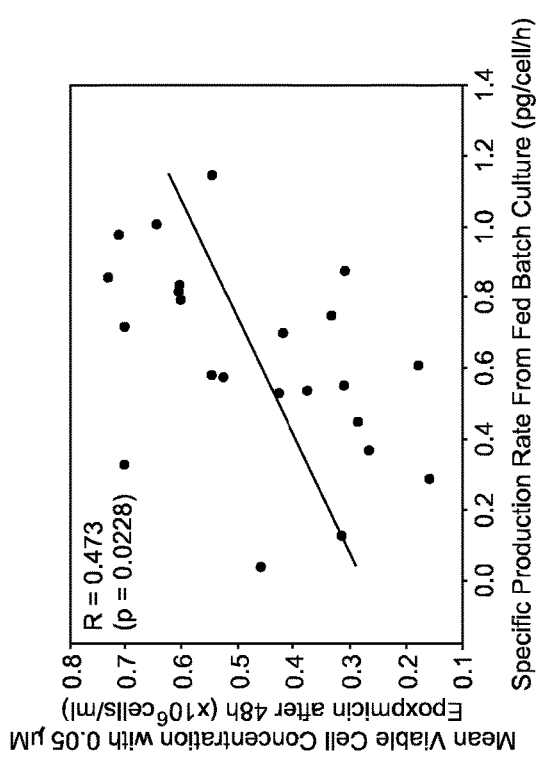
Figure 6C:
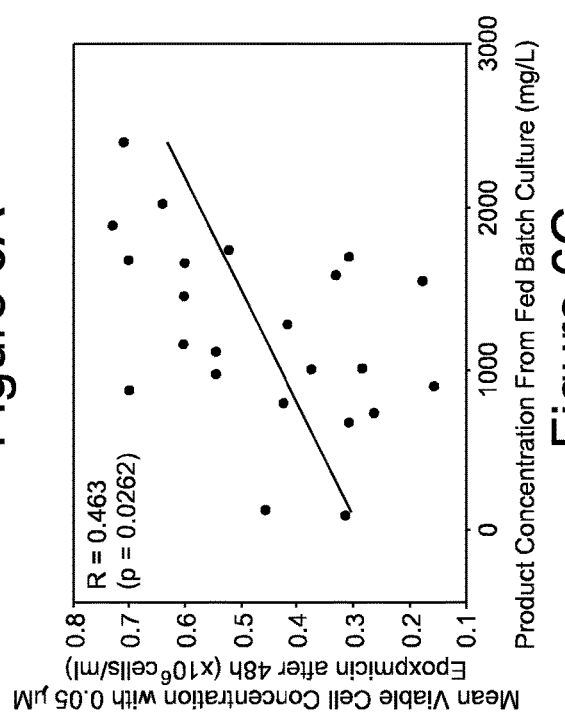
Figure 6F:
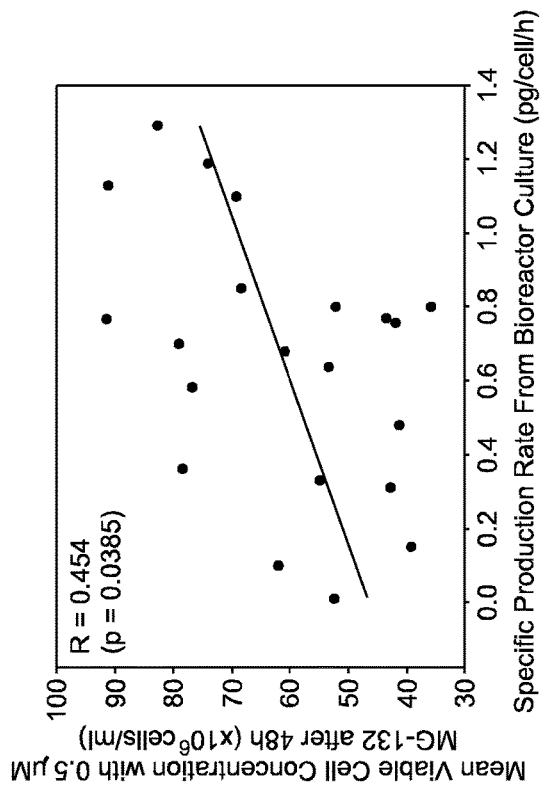
Figure 6E:
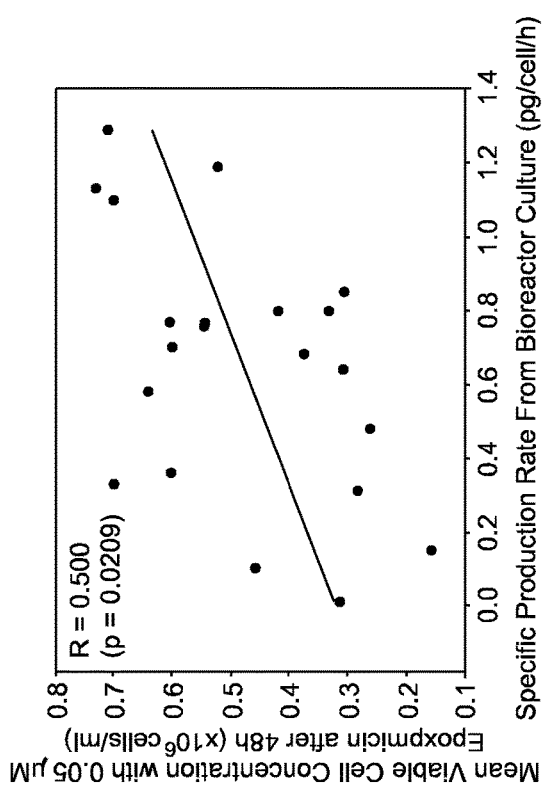
Figure 6G:
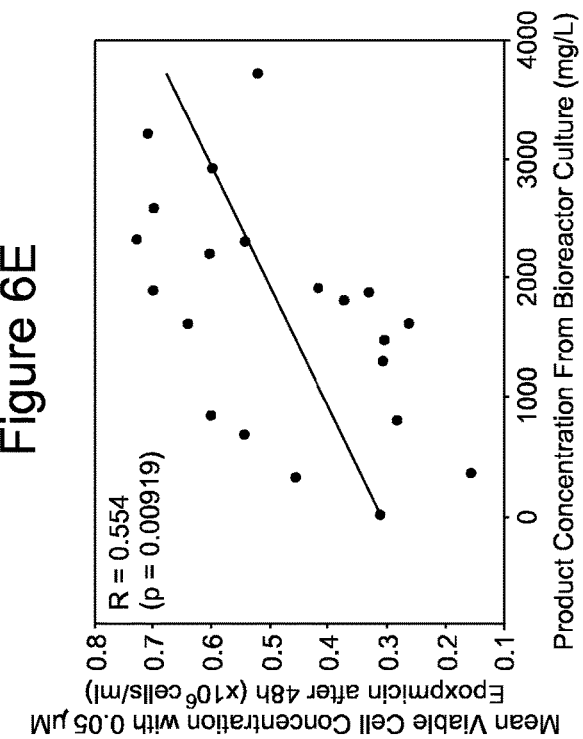
Figure 7B:
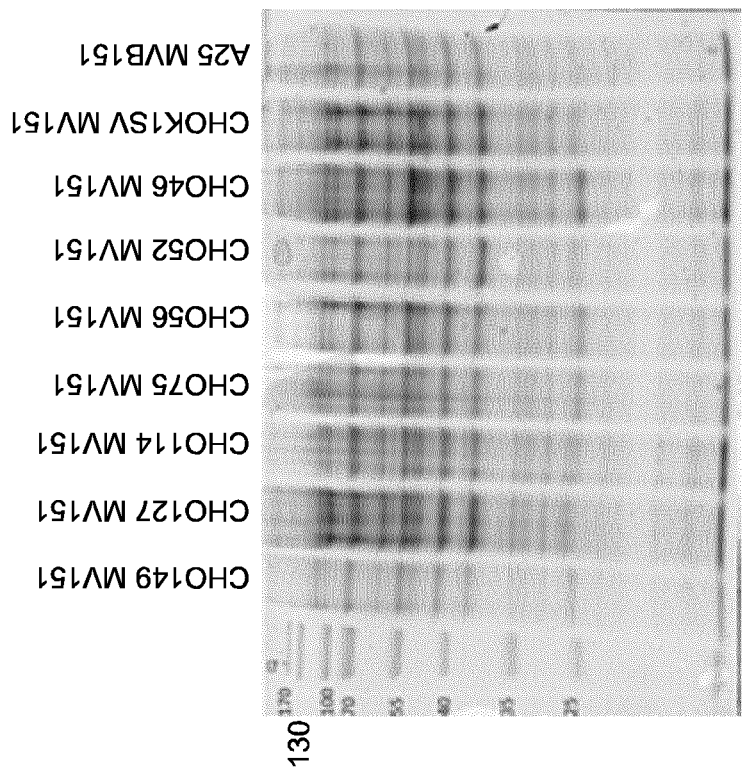
FIGS. 7A-7F are a series of gel images showing the analysis of proteasome activity using activity profiling probes and fluorescent intensity. Proteasome activity was determined in a range of antibody producing cell lines using fluorescently tagged activity probes with differing reactive groups. Cell lysates incubated with the probes were analyzed on 14% SDS-PAGE and the fluorescence was then measured on a Typhoon 9400 instrument using Cy3 and Cy2 filters.
Figure 7A:
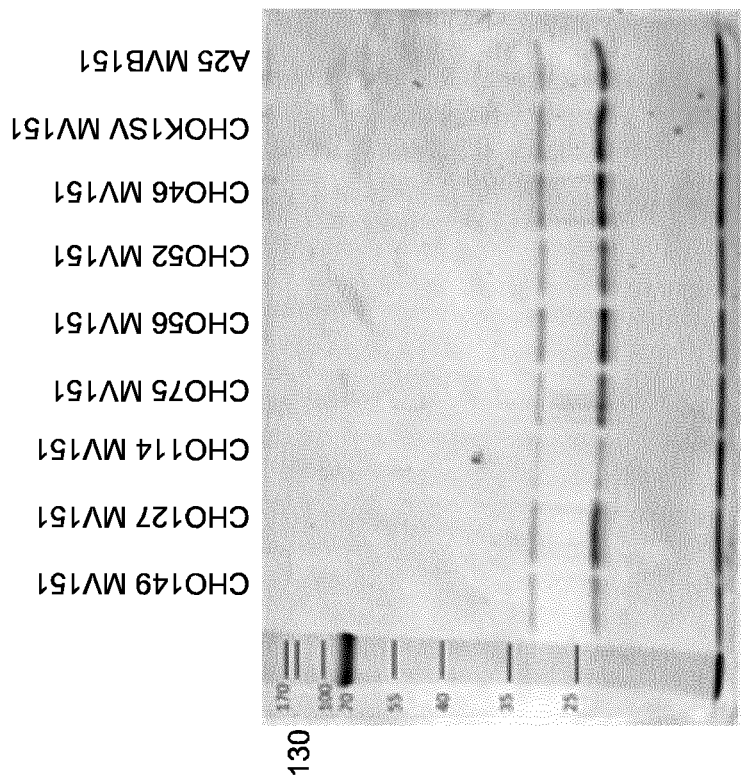
Figure 7D:
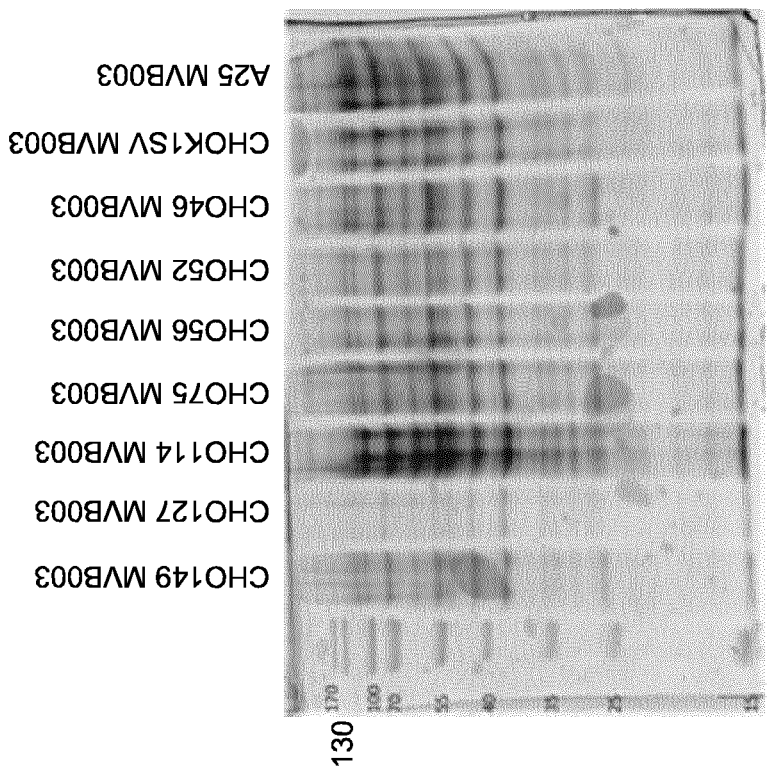
Figure 7C:
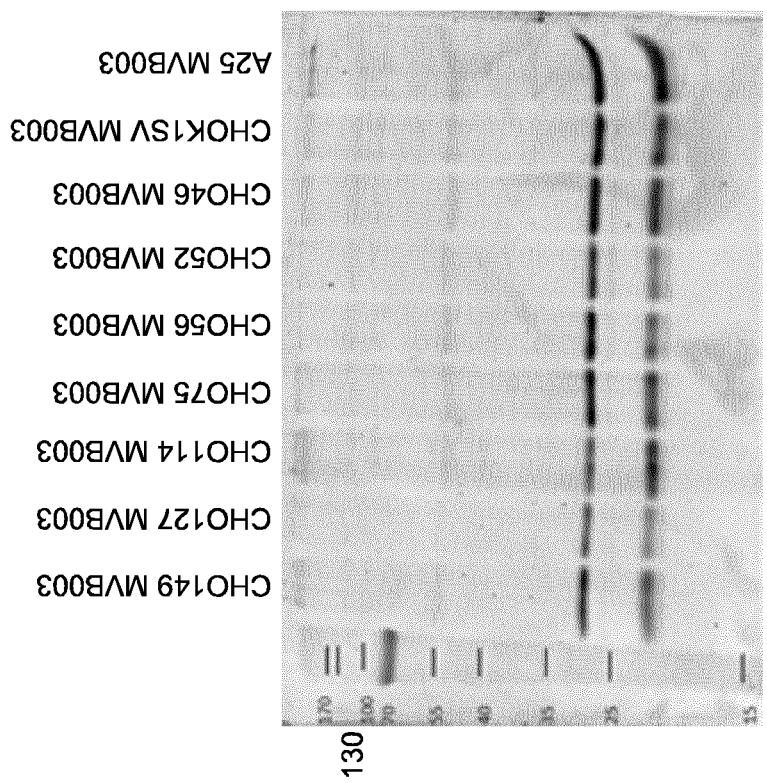
Figure 7F:
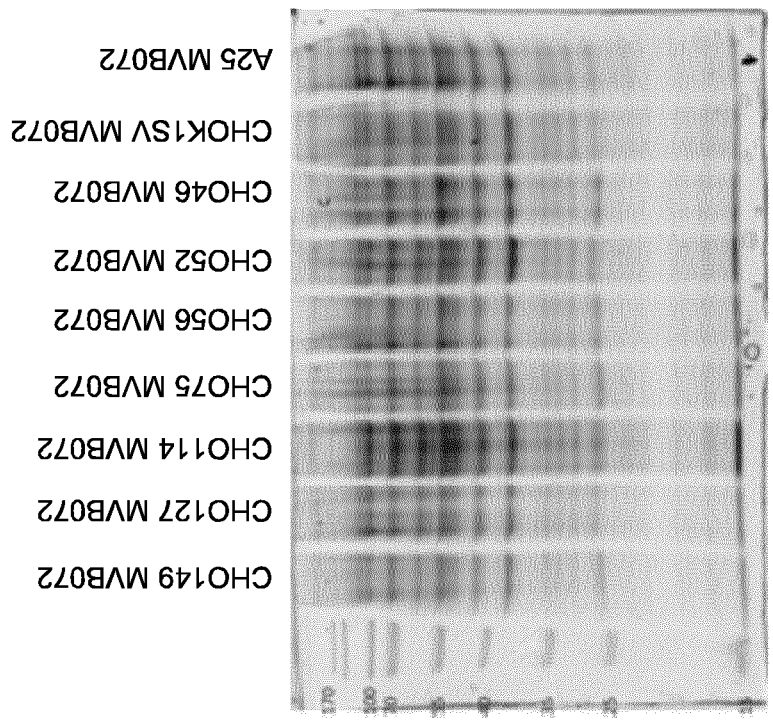
Figure 7E:
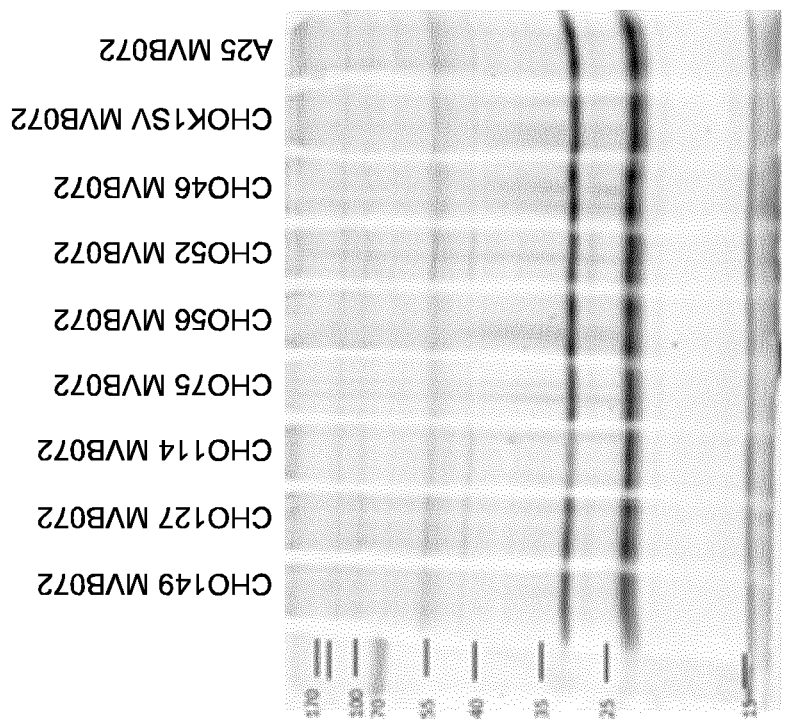
Figure 8B:
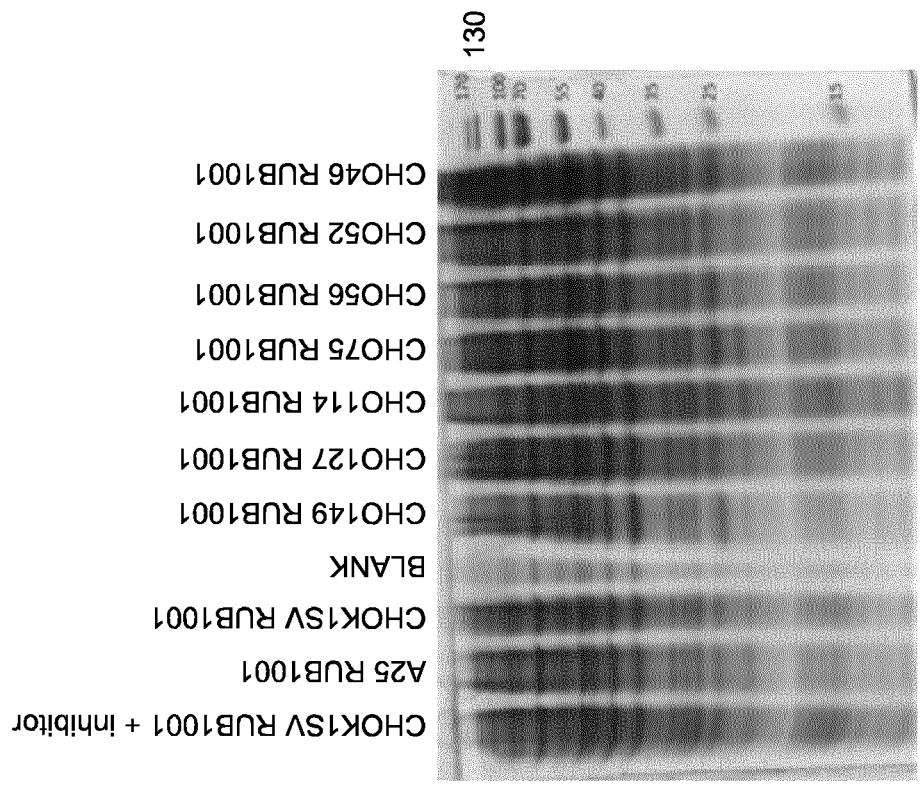
FIGS. 8A-8F are a series of images showing the analysis of proteasome activity using activity profiling probes and fluorescent intensity. Proteasome activity was determined in a range of antibody producing cell lines using fluorescently tagged activity probes with differing reactive groups. Cell lysates incubated with the probes were analyzed on 14% SDS-PAGE and the fluorescence was then measured on a Typhoon 9400 using Cy3 and Cy2 filters.
Figure 8A:
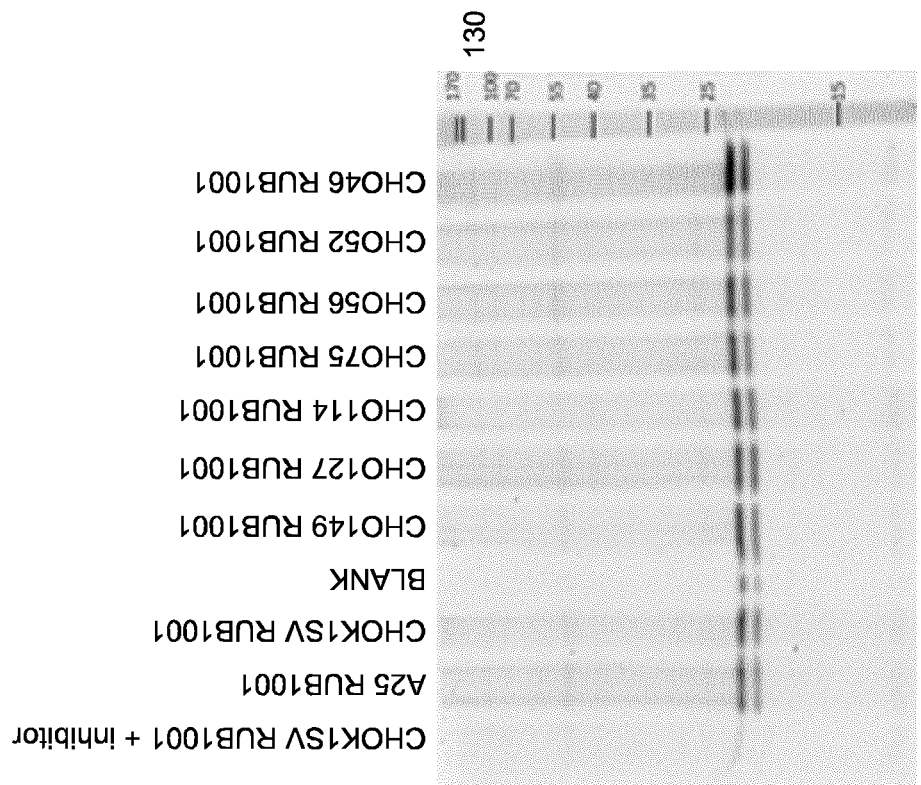
Figure 8D:
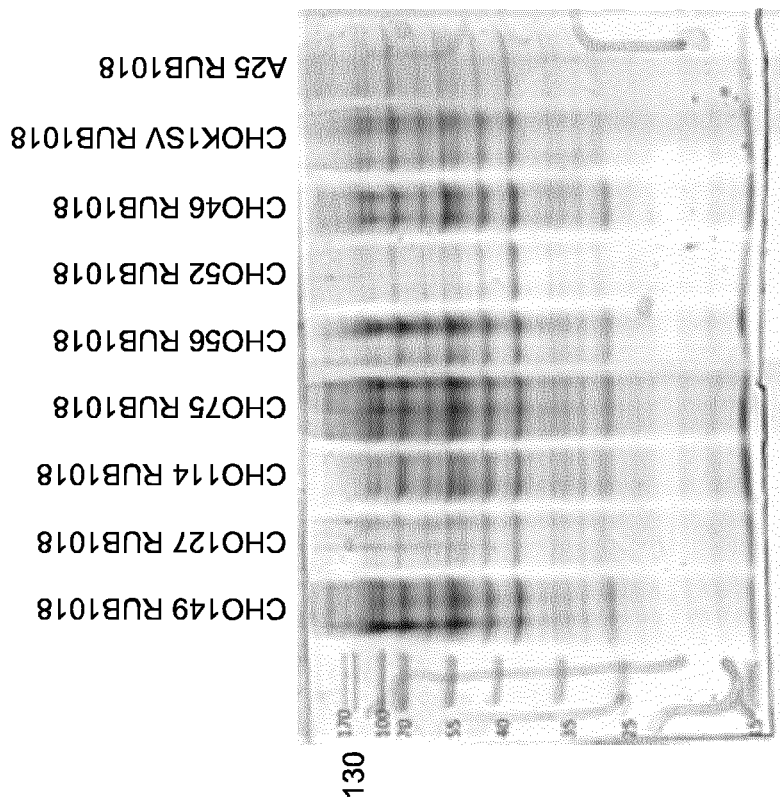
Figure 8C:
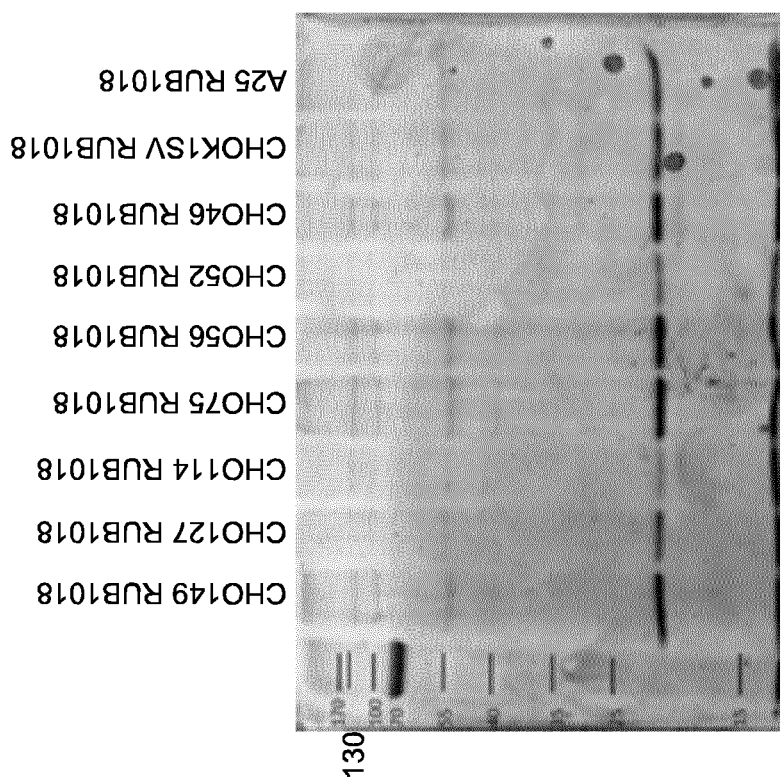
Figure 8F:
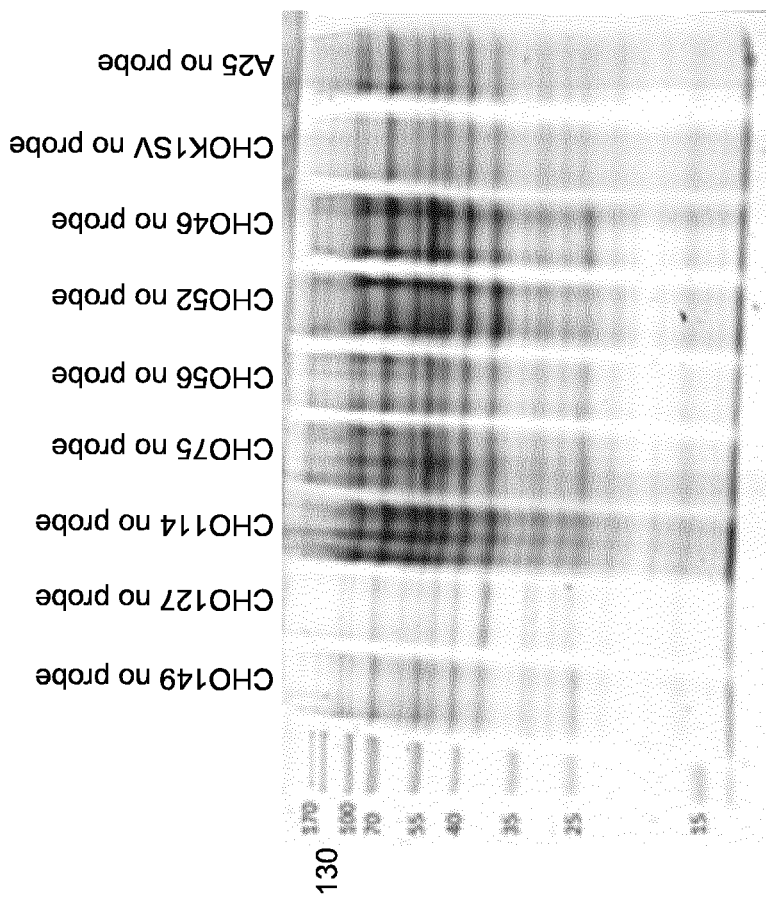
Figure 8E:
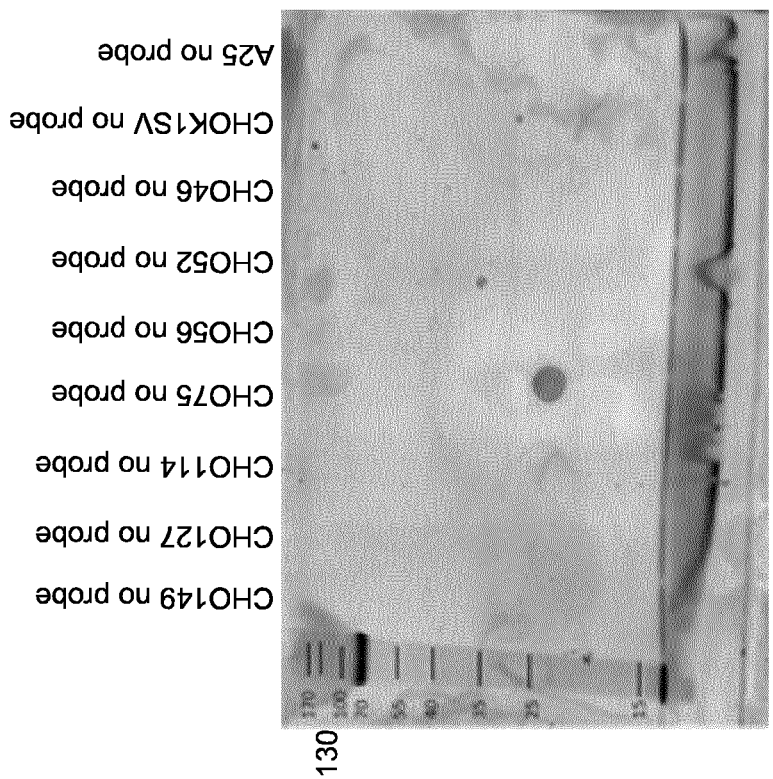
Figure 9A:
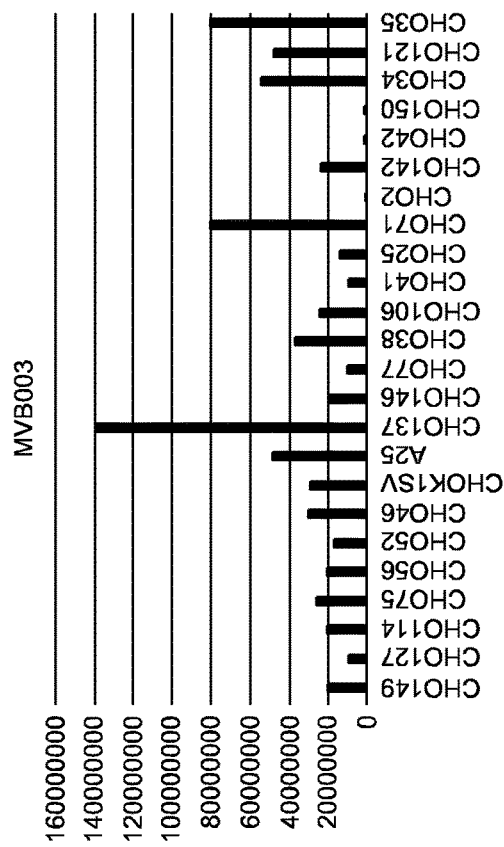
FIGS. 9A-9F are a series of graphs showing the activity of the different catalytic subunits of the proteasome as determined using the activity based profiling method and subsequent quantitation of band intensity. Densitometry of the bands from the gels in FIGS. 7A, 7C, and 7E, 8A, 8C, and 8E was performed using Life Technologies ImageQuant®. Graphs show intensity of the bands for each probes tested as well as the sum of all probes summarized in the total proteasome graph.
Figure 9B:
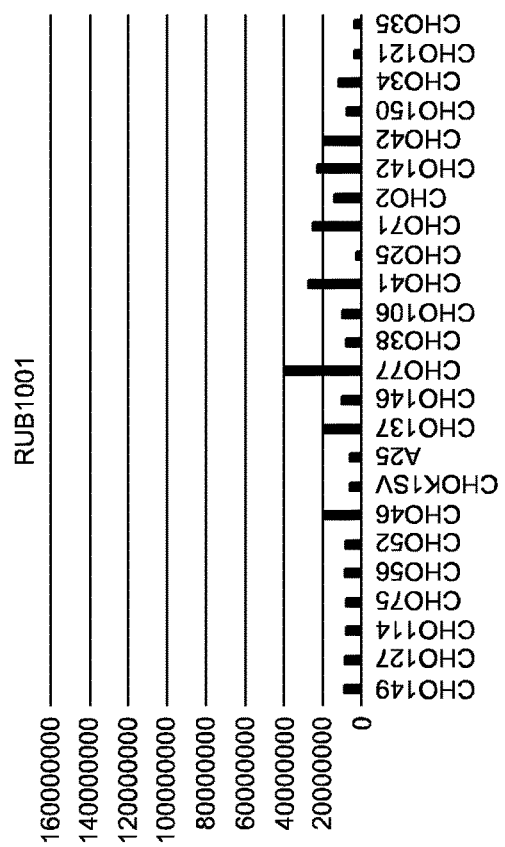
Figure 9C:
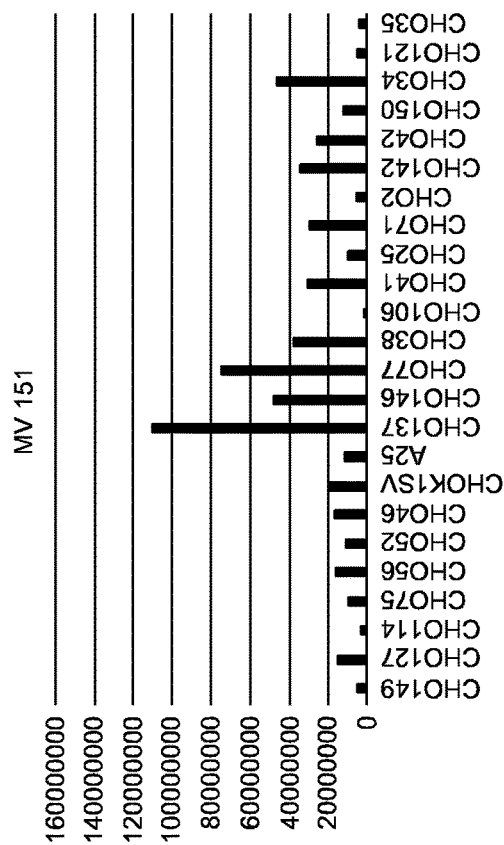
Figure 9D:
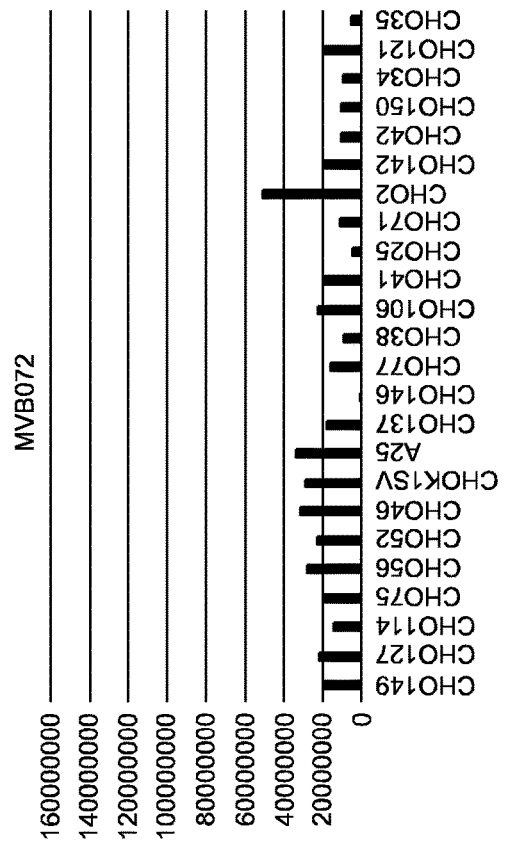
Figure 9F:
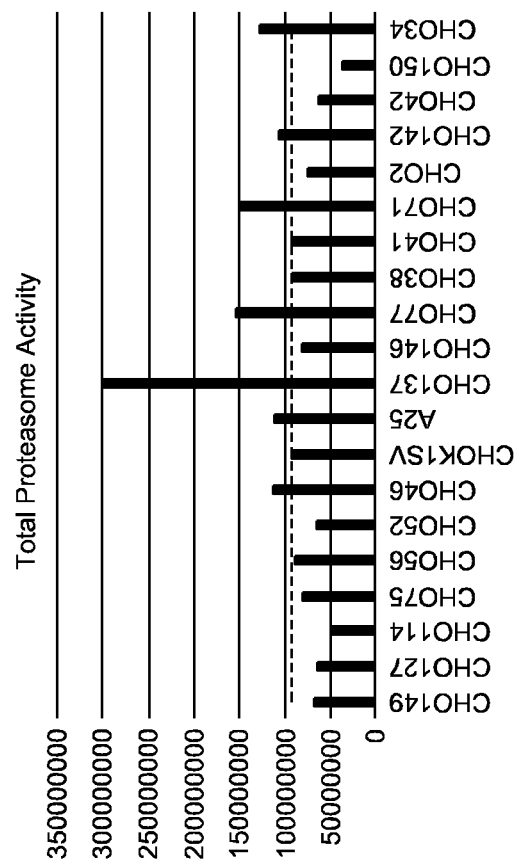
Figure 9E:
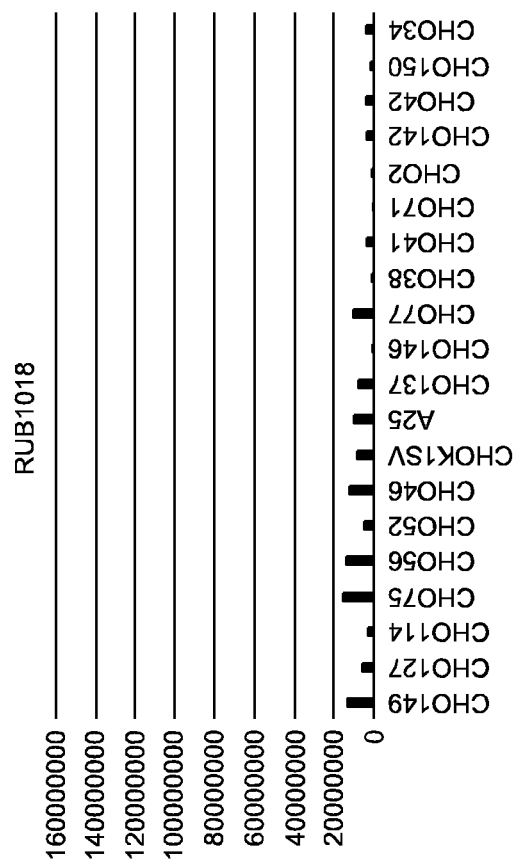

Recombinant proteins or polypeptides can be produced by recombinant DNA technology, expressed by host cells, and can be either purified from the host cell (e.g., *E. coli*) or secreted into the fluid, e.g., cell medium, in which the host cell is cultured and purified from the fluid. Cells capable of producing recombinant proteins or polypeptides in high yields and of appropriate quality are highly desired in the field. The methods disclosed herein for evaluating, classifying, identifying, making, or selecting a cell for production of a recombinant polypeptide are useful for identifying or making high productivity cells, to obtain high yields of recombinant polypeptide product or to provide higher quality preparations of recombinant polypeptide product. The methods disclosed herein are particularly useful for production of recombinant therapeutic polypeptides, where there is a demand for efficient cell line development, large quantities of the recombinant therapeutic polypeptide product, and high grade of quality for therapeutic use in patients.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

As used interchangeably herein, the terms "inhibitor of protein degradation" or "inhibitor of the protein degradation pathway", refers to an agent, e.g., a compound, which decreases (e.g., slows, attenuates, changes) the degradation of proteins, e.g., the reduction of proteins to their polypeptide, peptide, or amino acid constituents, either partially or fully, during protein synthesis and secretion in the cell. By way of example, an inhibitor of protein degradation can be identified by the ability to prevent or decrease (e.g., slow, attenuate, or change) one or more of the following: identification of a protein for degradation; tagging of a protein for degradation; retrotranslocation of a protein from the ER to the cytosol; association of a protein with the proteasome or association of the proteasome with the protein; entry of a protein to the proteasome; unfolding of a protein for entry into the proteasome; processing of the protein by the proteasome; release of the processed peptides from the proteasome; association of the proteasome with the endoplasmic reticulum; and/or proteasomal capacity of the cell; e.g., in a cell treated with a candidate inhibitor as compared to a similar cell not treated with the candidate inhibitor. In another embodiment, an inhibitor of protein degradation causes conditions to arise in the cell that prevents or reduces proteasomal activity, e.g., in a cell treated with a candidate inhibitor as compared to a similar cell not treated with the candidate inhibitor. In yet another embodiment, an inhibitor of protein degradation saturates the proteasomal activity of the cell, e.g., in a cell treated with a candidate inhibitor as compared to a similar cell not treated with the candidate inhibitor. Proteasomal degradation of a protein, e.g., an endogenously or exogenously expressed protein, can be measured or quantified by heavy/light isotope pulse-labelling approaches, such as stable isotope labeling by amino acids in cell culture (SILAC) followed by mass spectrometry (MS). Additional methodologies available in the art for assessing protein degradation are further described in Alvarez-Castelao et al., Biochemistry Research International, Volume 2012 (2012), Article ID 823597, 11 pages, hereby incorporated by reference.

As used herein, the term "protein degradation pathway" refers to cellular processes that result in the reduction of proteins to their polypeptide, peptide, or amino acid constituents, either partially or fully, e.g., the degradation of misfolded, surplus, truncated, or nonfunctional proteins. Exemplary elements of the protein degradation pathway include, but are not limited to, a proteasome (e.g. 26S proteasome or component thereof, e.g., 20S core or catalytic subunit, 19S regulatory subunit, or 11S regulatory subunit), enzymes that promote the identification of proteins to be degraded or ubiquitination (e.g., E1 ubiquitin activating enzyme, E2 ubiquitin conjugating enzyme, or E3 ubiquitin ligase); or enzymes that promote the translocation or retrotranslocation of proteins from the ER to another element of the protein degradation pathway, e.g., cytosol or proteasome (e.g., retrotranslocation enzyme/complex).

As used herein, the term "proteasome inhibitor" refers to a molecule that prevents or reduces the activity of a proteasome or a component of the proteasome. In one embodiment, the proteasome comprises a 20S catalytic or proteolytic core subunit, and one or more regulatory subunits, e.g., one or more 19S regulatory particles and/or one or more 11S regulatory particles. In embodiments, the activity of a proteasome or a component of the proteasome includes one or more of the following: association of a protein with the proteasome or association of the proteasome with the protein; entry of a protein to the proteasome; unfolding of a protein for entry into the proteasome; processing of the protein by the proteasome (e.g., reduction of the protein to peptide or amino acid constituents, partially or fully); release of the processed peptides or amino acids resulting from the processing of a protein from the proteasome; and association of the proteasome with the endoplasmic reticulum. In one embodiment, the proteasome inhibitor reduces the activity of the proteasome, or of a component of the proteasome, by about 1%, 2%, 5%, 10%, 15%, 20%, 25%, 30%, 35%, 40%, 45%, 50%, 55%, 60%, 65%, 70%, 75%, 80%, 85%, 90%, 95%, or 99%, as compared to the activity of a proteasome or a component thereof in the absence of the inhibitor.

As used herein, the term "ubiquitin pathway inhibitor" refers to a molecule that prevents or reduces the activity of one or more components of the ubiquitin pathway. The ubiquitin pathway is the process by which a target protein to be degraded is identified and tagged with ubiquitin molecules for recognition by the proteasome for degradation. Components of the ubiquitin pathway include ubiquitin activating enzymes (E1), ubiquitin conjugating enzymes (E2), and ubiquitin ligases (E3). In embodiments, the activity of one or more components of the ubiquitin pathway includes one or more of the following: identification of a protein for degradation, e.g., by an E3 ubiquitin ligase or substrate identification complex; activation of ubiquitin, e.g., by an E1 activating enzyme; transfer of the ubiquitin from an E1 to an E2 enzyme; and conjugation of a ubiquitin to a protein or to a ubiquitin molecule or chain (e.g., elongating a ubiquitin chain) on a protein, e.g, by an E3 ubiquitin ligase; deubiquitination by a deubiquitinating enzyme. In one embodiment, the ubiquitin pathway inhibitor reduces the activity of the one or more components of the ubiquitin pathway by about 1%, 2%, 5%, 10%, 15%, 20%, 25%, 30%, 35%, 40%, 45%, 50%, 55%, 60%, 65%, 70%, 75%, 80%, 85%, 90%, 95%, or 99% or more, as compared to the activity of one or more components of the ubiquitin pathway in the absence of the ubiquitin pathway inhibitor.

As used herein, the term "ERAD inhibitor" refers to a molecule that prevents or reduces the activity of one or more components of the endoplasmic reticulum associated degradation (ERAD) pathway. The ERAD pathway targets misfolded, mutated, or nonfunctional proteins of the endoplasmic reticulum for ubiquitination and subsequent degradation by the proteasome. Components of the ERAD pathway include chaperone proteins, e.g., Hsp70 family members, Hsp40 family members, Hsp90 family members, nucleotide exchange factors, small heat shock proteins, lectin-like chaperones; enzymes that identify or tag misfolded proteins, e.g., α-manosidases; enzymes or protein complexes that assist in retrotranslocation of misfolded proteins, e.g., retro-translocation complex (RTC); enzymes or protein complexes that ubiquitinate retro-translocated proteins, e.g., Hrd-Der ubiquitin ligase complex; and enzymes or protein complexes that deliver ubiquitinated proteins to the proteasome, e.g., Cdc48-Ufd1-Np14 complex. In embodiments, the activity of one or more components of the ERAD pathway includes one or more of the following: identification or tagging of a misfolded, nonfunctional protein for degradation; retrotranslocation of a protein from the ER to the cytosol; ubiquitination of the protein at the ER membrane, e.g., integrated into the ER membrane; delivery of the ubiquitinated protein to the proteasome; or deubiquitination of the proteins. In one embodiment, the ERAD inhibitor reduces the activity of the one or more components of the ERAD pathway by about 1%, 2%, 5%, 10%, 15%, 20%, 25%, 30%, 35%, 40%, 45%, 50%, 55%, 60%, 65%, 70%, 75%, 80%, 85%, 90%, 95%, or 99% or more, as compared to the activity of one or more components of the ERAD pathway in the absence of the ERAD inhibitor.

As used herein, the expression "a low concentration" when used in conjunction with an inhibitor of protein degradation, e.g., "a low concentration of a proteasome inhibitor", "a low concentration of an ubiquitination pathway inhibitor", or "a low concentration of an ERAD inhibitor", refers to a concentration of an inhibitor of protein degradation that results in a reduction in culture viability, e.g., 30%, 35%, 40%, 45%, 50%, 55%, 60%, 65%, 70%, 75%, 80%, 85%, 90%, 95%, or 99% reduction in culture viability when treated with the inhibitor of protein degradation, as compared to a culture that has not been treated with the inhibitor of protein degradation. As the purpose of using the inhibitor of protein degradation is to identify or select cells with improved production capacity or improved production quality, a low concentration of an inhibitor of protein degradation is a concentration that is less than that used to kill diseased cells for therapeutic benefit, e.g., cancer cells. It is understood that a culture viability below 30%, e.g., 20%, 10%, 5%, 1%, 0.5%, 0.1%, may still result in a population of selected cell that have improved productivity capacity and produce better quality products, and is also within the scope of the present disclosure. In another embodiment, the low concentration of the inhibitor of protein degradation is a concentration that partially, but not completely, inhibits protein degradation, e.g., a protein or process associated with protein degradation. By way of example, a low concentration of a proteasome inhibitor is a concentration that partially, but not completely inhibits protein degradation. Methods for assaying proteasome activity, e.g., inhibition of proteasome activity, are described herein.

As used herein, the term "endogenous" refers to any material from or naturally produced inside an organism, cell, tissue or system.

As used herein, the term "exogenous" refers to any material introduced to or produced outside of an organism, cell, tissue or system. Accordingly, "exogenous nucleic acid" refers to a nucleic acid that is introduced to or produced outside of an organism, cell, tissue or system. In an embodiment, sequences of the exogenous nucleic acid are not naturally produced, or cannot be naturally found, inside the organism, cell, tissue, or system that the exogenous nucleic acid is introduced into. In one embodiment, the sequences of the exogenous nucleic acids are non-naturally occurring sequences, or encode non-naturally occurring products.

As used herein, the term "heterologous" refers to any material from one species, when introduced to an organism, cell, tissue or system from a different species.

As used herein, the terms "nucleic acid," "polynucleotide," or "nucleic acid molecule" are used interchangeably and refers to deoxyribonucleic acid (DNA) or ribonucleic acid (RNA), or a combination of a DNA or RNA thereof, and polymers thereof in either single- or double-stranded form. The term "nucleic acid" includes, but is not limited to, a gene, cDNA, or an mRNA. In one embodiment, the nucleic acid molecule is synthetic (e.g., chemically synthesized or artificial) or recombinant. Unless specifically limited, the term encompasses molecules containing analogues or derivatives of natural nucleotides that have similar binding properties as the reference nucleic acid and are metabolized in a manner similar to naturally or non-naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the terms "peptide," "polypeptide," and "protein" are used interchangeably, and refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

As used herein, "product" refers to a molecule, nucleic acid, polypeptide, or any hybrid thereof, that is produced, e.g., expressed, by a cell which has been modified or engineered to produce the product. In one embodiment, the product is a naturally occurring product or a non-naturally occurring product, e.g., a synthetic product. In one embodiment, a portion of the product is naturally occurring, while another portion of the product is non-naturally occurring. In one embodiment, the product is a polypeptide, e.g., a recombinant polypeptide. In one embodiment, the product is suitable for diagnostic or pre-clinical use. In another embodiment, the product is suitable for therapeutic use, e.g., for treatment of a disease. In one embodiment, the product is selected from Table 1 or Table 2. In one embodiment, the modified or engineered cells comprise an exogenous nucleic acid that controls expression or encodes the product. In other embodiments, the modified or engineered cells comprise other molecules, e.g., that are not nucleic acids, that controls the expression or construction of the product in the cell.

In one embodiment, the modification of the cell comprises the introduction of an exogenous nucleic acid comprising a nucleic acid sequence that controls or alters, e.g., increases, the expression of an endogenous nucleic acid sequence, e.g., endogenous gene. In such embodiments, the modified cell produces an endogenous polypeptide product that is naturally or endogenously expressed by the cell, but the modification increases the production of the product and/or the quality of the product as compared to an unmodified cell, e.g., as compared to endogenous production or quality of the polypeptide.

In another embodiment, the modification of the cell comprises the introduction of an exogenous nucleic acid encoding a recombinant polypeptide as described herein. In such embodiments, the modified cell produces a recombinant polypeptide product that can be naturally occurring or non-naturally occurring. In such embodiments, the modified cell produces a recombinant polypeptide product that can also be endogenously expressed by the cell or not. In embodiments where the recombinant polypeptide product is also endogenously expressed by the cell, the modification increases the production of the product and/or the quality of the product as compared to an unmodified cell, e.g., as compared to endogenous production or quality of the polypeptide.

As used herein, "recombinant polypeptide" or "recombinant protein" refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering (of the cell or of a precursor cell); e.g., at least one nucleotide was altered, e.g., it was introduced into the cell or it is the product of a genetically engineered rearrangement. In an embodiment, the sequence of a recombinant polypeptide does not differ from a naturally occurring isoform of the polypeptide or protein. In an embodiment, the amino acid sequence of the recombinant polypeptide differs from the sequence of a naturally occurring isoform of the polypeptide or protein. In an embodiment, the recombinant polypeptide and the cell are from the same species. In an embodiment, the recombinant polypeptide is endogenous to the cell, in other words, the cell is from a first species and the recombinant polypeptide is native to that first species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from different species, e.g., the recombinant polypeptide is a human polypeptide and the cell is a non-human, e.g., a rodent, e.g., a CHO, or an insect cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally occurring isoform of the human polypeptide or protein. In an embodiment, the recombinant polypeptide differs from a naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide by no more than 1, 2, 3, 4, 5, 6, 7, 8, 9, 10, or 15% of its amino acid residues.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Modulation of the Protein Degradation Pathway

During cell line construction, e.g., recombinant cell line construction, cellular processes are triggered within the cell when the folding and modification capabilities of the cell are exceeded. The unfolded protein response (UPR) during ER stress and ER-associated degradation (ERAD) are key cellular processes that deal with misfolded or unassembled proteins during protein synthesis. Key responses that are activated by these processes include ER chaperone up-regulation, reduction in global protein synthesis by reducing translation initiation and, ultimately, if the stress persists, apoptosis (Schroder & Kaufman 2005; Chakrabarti et al. 2011). It is proposed that 30% of newly translated polypeptides are targeted for degradation, possibly as a result of misfolding (Du et al. 2013; Schubert et al. 2000; Yewdell & Nicchitta 2006). It is thought that these processes not only help to maintain protein quality but also provide an important source of 'recycled' amino acids as new building blocks for new polypeptide synthesis. It is therefore important that the cell has mechanisms in place to deal with, and recycle, the components of incorrectly folded polypeptides and maintains a quality control process.

ERAD requires that polypeptides/proteins in the ER destined for destruction are transported back out of the ER to the cytosol, e.g., retrotranslocated, where they are degraded by the proteasome (Olzmann et al. 2013). If homeostasis cannot be restored then the processes activated by the UPR can ultimately lead to apoptosis. The UPR provides the cell with the capability to adjust the ER capacity during periods of high demand and an element of UPR induction is thought to be beneficial to recombinant protein yield, however excessive and long term activation can be detrimental to the cell and culture viability.

The present disclosure is based, in part, on the results of a study to determine whether the capability of the cells to initiate protein turnover from the ER is linked to the ability of cells to produce a recombinant polypeptide, and further, whether inhibition of the protein degradation pathway, e.g., by inhibiting proteasome activity or polypeptide transport out of the ER during ERAD, could be used to select for cells with enhanced capability of these processes that would in turn reflect their ability to produce recombinant protein. The present disclosure provides methods and compositions for using inhibitors of protein degradation for identifying or selecting cells that have the capacity for high production of a product, e.g., a recombinant polypeptide, and for generating recombinant cell lines that have increased production, e.g., produce higher yields of a recombinant polypeptide product, and/or can produce higher quality recombinant polypeptide products.

Inhibitors of Protein Degradation

The methods described herein include contacting a cell, or a population of cells, with an inhibitor of protein degradation. In an embodiment, the inhibitors of protein degradation described herein inhibits or reduces the activity of a process or a protein involved in the protein degradation pathway, e.g., proteasome degradation, the ER-associated degradation pathway, and/or the ubiquitin pathway. As described herein, the inhibitor of protein degradation can include, but is not limited to, a proteasome inhibitor, an ubiquitin pathway inhibitor, or an ERAD inhibitor. In an embodiment, the inhibitor may be reversible or irreversible. In embodiments, the inhibitor can be a small molecule, a nucleic acid, or a polypeptide.

The proteasome is a large, multienzyme complex comprising one or more protein-digesting enzymes, e.g., proteases. The 26S proteasome comprises a 20S proteolytic core subunit and one or two 19S regulatory particles. The 20S core contains three types of active sites, e.g. proteolytic or peptidase sites. In embodiments, the proteasome inhibitors described herein can inhibit or reduce the activity of any component of the proteasome. In an embodiment, the proteasome inhibitor binds to and/or inhibits one or more active sites of a component of the proteasome, e.g., one or more of the active sites of the 20S proteolytic core. In an embodiment, the proteasome inhibitor inhibits or reduces the activity of the 20S proteolytic core. In an embodiment, the proteasome inhibitor inhibits or reduces the activity of the 19S regulatory particle. In some embodiments, the proteasome inhibitor inhibits or reduces the activity of a protease, e.g., a trypsin protease, a chymotrypsin protease, or a calpain. In one embodiment, the proteasome inhibitor reduces the activity of the proteasome or of a component of the proteasome by about 1%, 2%, 5%, 10%, 15%, 20%, 25%, 30%, 35%, 40%, 45%, 50%, 55%, 60%, 65%, 70%, 75%, 80%, 85%, 90%, 95%, or 99%, as compared to the activity of a proteasome or a component thereof in the absence of the inhibitor.

In an embodiment, the proteasome inhibitor is selected from MG132 or epoximicin. Other exemplary proteasome inhibitors are known in the art, and include, but are not limited to Z-Leu-Leu-Leu-B(OH)2 (MG262), bortezomib (PS-341, Velcade, pyrazylcarbonyl-Phe-Leu-boronate), carfilzomib (PR-171), marizomib, MLN9708 (Ninlaro), ixazomib (MLN2238), oprozomib (ONX 0912), delanzomib (CEP-18770), CEP1612, celastrol, ONX-0914 (PR-957), disulfiram, epigallocatchin-3-gallate, salinosporamide A, AM114, lactacystin, ps-341, eponomicin, Z-Leu-Leu-LeuVS, MG115, calpeptin, PSI, and calpain inhibitor II. Other exemplary proteasome inhibitors include NVLS, PS-519, antiprotealide, fluorosalinosporamide, and cinnabaramides (e.g., Cinnabaramides A-G).

The proteasome inhibitor may be any one described in Dick, et al., *Biochem.* 30: 2725 (1991); Goldberg, et al., *Nature* 357: 375 (1992); Goldberg, *Eur. Biochem.* 203: 9 (1992); Orlowski, *Biochem.* 29: 10289 (1989); Rivett, et al., *Archs. Biochem. Biophys.* 218: 1 (1989); Rivett, et al., *J. Biol. Chem.* 264: 12, 215 (1989); Tanaka, et al., *New Biol.* 4: 1 (1992), and U.S. Pat. No. 5,693,617.

The proteasome inhibitor can be a peptide aldehyde or a peptide alpha-keto esters containing a hydrophobic residue in the P1 position as described in Vinitsky, et al. (*Biochem.* 31: 9421 (1992), see also Orlowski, et al., *Biochem.* 32: 1563 (1993)), which were characterized as inhibitors of the chymotrypsin-like activity of the proteasome. The proteasome inhibitor can be a tripeptide, e.g., Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H and Z-Arg-Ile-Phe-H, where OR, along with the carbonyl of the preceding amino acid residue, represents an ester group.

The proteasome inhibitor can be an inhibitor of a chymotrypsin-like protease as disclosed by Siman, et al. (WO 01/13904). These inhibitors have the formula R-A4-A3-A2-Y, wherein R is hydrogen, or an N-terminal blocking group; A4 is a covalent bond, an amino acid or a peptide; A3 is a covalent bond, a D-amino acid, Phe, Tyr, Val or a conservative amino acid substitution of Val; A2 is a hydrophobic amino acid or lysine or a conservative amino acid substitution thereof, or when A4 includes at least two amino acids, A2 is any amino acid; and Y is a group reactive with the active site of said protease. The proteasome inhibitor can also be a peptide ketoamide, ketoacid, or ketoester useful in inhibiting serine proteases and cysteine proteases, as described in Powers (WO 92/12140). The proteasome inhibitor can also be a calpain inhibitor compound as described in Bartus, et al. (WO 92/1850).

Other proteasome inhibitors include, but are not limited to: Calpain Inhibitor I, MG101, Calpain Inhibitor II, Fraction I (FrI, Hela), Fraction II (FII), clasto-Lactacystin beta-lactone (omuralide), Lactacystin, MG-115, Antiserum to NEDD8, PA28 Activator, 20S Proteasome, Polyclonal Antibody to Proteasome 20S alpha-Type 1 Subunit, Polyclonal Antibody to Proteasome 26S Subunit S10B, Polyclonal Antibody to Proteasome 26S Subunit S2, Polyclonal Antibody to Proteasome 26S Subunit S4, Polyclonal Antibody to Proteasome 26S Subunit S5A, Polyclonal Antibody to Proteasome 26S Subunit S6, Polyclonal Antibody to Proteasome 26S Subunit S6', Polyclonal Antibody to Proteasome 26S Subunit S7, Polyclonal antibody to Proteasome 26S Subunit S8, Polyclonal antibody to Proteasome Activator PA28 Alpha, polyclonal antibody to Proteasome Activator PA28 Gamma, Polyclonal antibody to Proteasome Activator PA700 Subunit 10B, 26S Proteasome Fraction, Proteasome Inhibitor I, Proteasome Inhibitor II, Proteasome Substrate I (Fluorogenic), Proteasome Substrate II (Fluorogenic), Proteasome Substrate III (Fluorogenic), Proteasome Substrate IV (Fluorogenic), S-100 Fraction, SUMO-1/Sentrin-1 (1-101), SUMO-1/Sentrin-1 (1-97), Antiserum to SUMO-1/Sentrin-1, Ubc10, Ubc5b, Ubc5c, Ubc6, Ubc7, Antiserum to Ubc9, Ubc9, UbCH2/E2-14K, UbCH3/Cdc34, UbCH5a, Ubiquitin Activating Enzyme (E1), Ubiquitin Activating Enzyme (E1), Ubiquitin Aldehyde, Ubiquitin Conjugating Enzyme Fractions, Ubiquitin C-terminal Hydrolase, Ubiquitin K48R, Methylated Ubiquitin, GST-Ubiquitin, (His)6 Ubiquitin, Ubiquitin-AMC, Ubiquitin-Sepharose.

In addition to known proteasome inhibitors, a proteasome inhibitor useful in the methods described herein can be routinely tested for their ability to inhibit proteasome activity. Various strategies for the identification of such inhibitors are exemplified in the art. For example, small molecule libraries, often comprising extracts from plants or more simple organisms, may be screened for their ability to inhibit the proteasome or specific protease types. Alternatively, a rational design approach may be applied using, for example, peptide or peptidomimetic compounds designed specifically to interact with the active site of a proteasome component (see e.g., Siman, et al., WO91/13904; Powers, et al., in Proteinase Inhibitors, Barrett, et al. (eds.), Elsevier, pp. 55-152 (1986)). The inhibitors can be stable analogs of catalytic transition states such as Z-Gly-Gly-Leu-H, which inhibits the chymotrypsin-like activity of the proteasome (Orlowski, *Biochemistry* 29: 10289 (1990); see also Kennedy and Schultz, *Biochem.* 18: 349 (1979)).

In addition, a variety of natural and chemical proteasome inhibitors reported in the literature, or analogs thereof, are intended to be encompassed by the present invention including, but not limited to, peptides containing an α-diketone or an α-ketone ester, peptide chloromethyl ketone, peptide epoxyketones, peptide vinyl sulphones, beta-lactone-containing compounds, peptide boronates isocoumarins, peptide sulfonyl fluorides, peptidyl boronates, peptide epoxides, and peptidyl diazomethanes. Angelastro, et al., *J. Med. Chem.* 33: 11 (1990); Bey, et al., EPO 363, 284; Bey, et al., EPO 363, 284; Bey, et al., EPO 364, 344; Grubb, et al., WO 88/10266; Higuchi, et al., EPO 393, 457; Ewoldt, et al., *Mol. Immunol.* 29(6): 713 (1992); Hernandez, et al., *J. Med. Chem.* 35(6): 1121 (1992); Vlasak, et al., *J. Virol.* 63(5): 2056 (1989); Hudig, et al., *J. Immunol.* 147(4): 1360 (1991); Odake, et al., *Biochem.* 30(8): 2217 (1991); Vijayalakshmi, et al., *Biochem.* 30(8): 2175 (1991); Kam, et al., *Thrombosis and Haemostasis* 64(1): 133 (1990); Powers, et al., *J. Cell. Biochem.* 39(1): 33 (1989); Powers, et al., Proteinase Inhibitors, Barrett et al., Eds., Elsevier, pp. 55-152 (1986); Powers, et al., *Biochem* 29(12): 3108 (1990); Oweida, et al., *Thrombosis Res.* 58(2): 391 (1990); Hudig, et al., *Mol. Immunol.* 26(8): 793 (1989); Orlowski, et al., *Arch. Biochem. and Biophys.* 269(1): 125 (1989); Zunino, et al., *Biochem. et Biophys. Acta* 967(3): 331 (1988); Kam, et al., *Biochem.* 27(7): 2547 (1988); Parkes, et al., *Biochem. J.* 230: 509 (1985); Green, et al., *J. Biol. Chem.* 256: 1923 (1981); Angliker, et al., *Biochem. J.* 241: 871 (1987); Puri, et al., *Arch. Biochem. Biophys.* 27: 346 (1989); Hanada, et al., Proteinase Inhibitors: Medical and Biological Aspects, Katunuma, et al., Eds., *Springer-Verlag* pp. 25-36 (1983); Kajiwara, et al., *Biochem. Int.* 15: 935 (1987); Rao, et al., *Thromb. Res.* 47: 635 (1987); Tsujinaka, et al., *Biochem. Biophys. Res. Commun.* 153: 1201 (1988)).

Proteasome activity can be measured by proteasome activity assays known in the art and as described herein, e.g., in Examples 1 and 4.

Ubiquitination plays a critical role in protein degradation. Ubiquitin is a small, 8.5 kDa, protein that is attached to a substrate protein via an isopeptide bond between the carboxylic acid group of the ubiquitin's glycine and the epsilon amino group of a lysine in the substrate protein. Ubiquitination of a substrate protein occurs in three main steps: 1) activation of the ubiquitin by ATP-dependent E1 ubiquitin activating enzyme (also referred to herein as E1); 2) transfer of the ubiquitin from the E1 to the active site of an E2 ubiquitin conjugating enzyme (also referred to herein as E2); and 3) ligation of the ubiquitin to the substrate protein via an E3 ubiquitin ligase (also referred to herein as E3), e.g., formation of the isopeptide bond between the ubiquitin molecule and the substrate protein. Ubiquitinated proteins are targeted for degradation by the proteasome. In one embodiment, the ubiquitin pathway inhibitor reduces the activity of the one or more components of the ubiquitin pathway by about 1%, 2%, 5%, 10%, 15%, 20%, 25%, 30%, 35%, 40%, 45%, 50%, 55%, 60%, 65%, 70%, 75%, 80%, 85%, 90%, 95%, or 99% or more, as compared to the activity of one or more components of the ubiquitin pathway in the absence of the ubiquitin pathway inhibitor.

In an embodiment, the ubiquitin pathway inhibitors described herein can inhibit any of the steps or enzymes involved in the ubiquitination cascade. For example, an ubiquitination inhibitor can inhibit or reduce the activity of one or more of, e.g., one, two, or all of, E1, E2, or E3. In an embodiment, the ubiquitin pathway inhibitor inhibits or reduces the activity of any E1, E2, or E3 known in the art. For example, E3 ubiquitin ligases include, but are not limited to, APC/C ubiquitin ligase, HECT E3 ubiquitin ligase, β-TrCP1 ligase, MDM2, and the SCF ubiquitin ligase.

In an embodiment, the ubiquitin pathway inhibitor is (−)-parthenolide, thalidomide, TAME, A01 (Tocris, Cat. No. 5397), Apcin (R&D Systems, Cat. No. I-444), GS143 (Tocris, Cat No. 5636), Heclin (Tocris, Cat. No. 5433), HLI373 (Tocris, Cat. No. 3503), NSC 66811 (Tocris, Cat. No. 2936), NSC-687852 (Biovision, Cat. No. 2021-5), NAB 2 (R&D Systems, Cat. No. 5131), Nutlin-3 (Tocris, Cat. No. 3984), PRT 4165 (Tocris, Cat. No. 5047), PTC 209 (Tocris, Cat. No. 5191), RITA (Tocris, Cat. No. 2443), SKPin C1 (Tocris, Cat. No. 4817), SMER3 (Tocris, Cat. No. 437), SP141 (Tocris, Cat. No. 5332), SZL P1-31 (Tocris, Cat. No. 5076), TAME hydrochloride (Tocris, Cat. No. 4506), proTAME (R&D Systems, Cat No. I-440), or TCID (Biovision, Cat. No. 2204-5).

Ubiquitination can be measured by ubiquitination assays known in the art.

Elimination of misfolded proteins from the ER by ER-associated degradation involves, for example, identification and tagging of misfolded proteins to be degraded, retro-translocation of the misfolded protein from the ER lumen into the cytosol, ubiquitination of the protein, and delivery to the proteasome for degradation. A protein complex, p97-Ufd1-Np14 ATPase complex hydrolyzes ATP to dislocate ubiquitinated proteins into the cytosol. A p97-associated deubiquitinating enzyme prevents the components of the p97-Ufd1-Np14 ATPase complex itself from being targeted, e.g., ubiquitinated, and degraded by the proteasome. Thus, in an embodiment, an ERAD inhibitor inhibits or reduces the activity of one or more of the components of the p97-Ufd1-Np14 ATPase complex, e.g., inhibits or reduces the activity of the ATPase of the p97-Ufd1-Np14 ATPase complex. In one embodiment, the ERAD inhibitor reduces the activity of the one or more components of the ERAD pathway by about 1%, 2%, 5%, 10%, 15%, 20%, 25%, 30%, 35%, 40%, 45%, 50%, 55%, 60%, 65%, 70%, 75%, 80%, 85%, 90%, 95%, or 99% or more, as compared to the activity of one or more components of the ERAD pathway in the absence of the ERAD inhibitor.

In one embodiment, an ERAD inhibitor inhibits or reduces the activity of one or more components of the ERAD pathway. Components of the ERAD pathway include, but are not limited to, Hsp70 family members, Hsp40 family members, Hsp90 family members, nucleotide exchange factors (NEFs) (e.g., Nhs, Bag-1), Rot1, calnexin, alreticulin, α-mannosidase (Mns1), ER Degradation Enhancing α-mannosidase-like protein (EDEM), Kar2, Sec61 complex (components include, e.g., Sec61α and Sec61γ), protein disulfide isomerases (PDI), Yos9, Cdc48p, p9'7, VCP/p97 complex, Hrd1, Doa10, Ubc1, Cue1, Ubc6, and Ubc7.

In an embodiment, an ERAD inhibitor includes, but is not limited to, eeyarestatin I (also referred to as ESI), cotransin, CAM741, apratoxin A, exotoxin A, HUN-7293, decatransin, valinomycin, mycolactone, NSC 630668-R/1 (also referred to as R/1), MAL3-39, MAL3-101, E6 Berbamine, Ophiobolin A, CADA cyclotriazadisulfoniamide, e.g., inhibitors described in Kalies et al., 2015, Traffic, 16:1027-1038; incorporated herein by reference.

In one embodiment, one or more inhibitors of protein degradation, as described herein, are used in the methods described herein. For example, two, three, four, or five, or more, inhibitors of protein degradation as described herein are used. In an embodiment, the two or more inhibitors of protein degradation may disrupt the same process in the protein degradation pathway, e.g., the two or more inhibitors inhibit or reduce proteasome activity. In an alternative embodiment, the two or more inhibitors of protein degradation disrupt different processes in the protein degradation pathway, e.g., one inhibitor inhibits or reduces proteasome activity while another inhibitor inhibits or reduces ERAD activity or the ubiquitin pathway.

Determination of the appropriate concentrations of the inhibitors of protein degradation is well within the skill of the ordinary skilled artisan. Assay for determining concentrations of such inhibitors, e.g., determining appropriate concentrations of the inhibitor for desired culture viability, and/or protein degradation inhibition, e.g., proteasome inhibition, are described herein and in the Examples herein. The appropriate concentration of the inhibitors of protein degradation for use in the methods described herein may differ in different cell types or cells from different species. In the embodiments described herein, the inhibition or reduction of proteasome activity is determined as compared to a cell that has not been contacted with the proteasome inhibitor, or as compared to a reference cell that has been contacted with the proteasome inhibitor.

In some embodiments, a low concentration of the inhibitor of protein degradation is used in the methods described herein. Low concentrations of the inhibitor of protein degradation may be preferred for cells that have undergone one or more selection steps prior to contacting with, e.g., exposure to, the inhibitor of protein degradation as described herein. By way of example, a low concentration of the inhibitor of protein degradation is administered to the cell after selection is performed to identify cells that have stably integrated an exogenous nucleic acid into the genome.

In one embodiment, the concentration of the inhibitor of protein degradation is a concentration that results in the inhibition or reduction of protein degradation, e.g., inhibition or reduction of activity of one or more component of the proteasome, the ubiquitin pathway, or the ERAD pathway as described herein. In an embodiment, the concentration of the inhibitor of protein degradation is a concentration that results in about 20%, 25%, 30%, 35%, 40%, 45%, 50%, 55%, 60%, 65%, 70%, 75%, 80%, 85%, 90%, 95%, or 99% or more culture viability (e.g., 20%, 25%, 30%, 35%, 40%, 45%, 50%, 55%, 60%, 65%, 70%, 75%, 80%, 85%, 90%, 95%, or 99% or more of cells are viable or survive in a population of cells contacted by, e.g., cultured in the presence of, an inhibitor of protein degradation described herein) in a culture or population of cells that are contacted by, e.g., cultured in the presence of, the inhibitor of protein degradation. In an embodiment, the concentration of the inhibitor of protein degradation is a concentration at which some portion of the cells contacted by the inhibitor of protein degradation continue to proliferate, e.g., 20%, 25%, 30%, 35%, 40%, 45%, 50%, 55%, 60%, 65%, 70%, 75%, 80%, 85%, 90%, 95%, or 99% or more of cells continue to proliferate when contacted by, e.g., cultured in the presence of, the inhibitor of protein degradation. In some embodiments, the concentration of an inhibitor of protein degradation described herein results in less than 20%, e.g., 15%, 10%, 5%, 1%, 0.5%, or 0.1%, of the total number of cells remaining after contacting the cell with, e.g., culturing the cell in the presence of, the inhibitor of protein degradation.

In one embodiment, the inhibitor of protein degradation is MG-132. MG-132 has been used at 1.5 µM to induce apoptosis (Meriin et al. 1998). In an embodiment, the concentration of MG-132 suitable for the methods described herein is less than 1.5 µM, less than 1.25 µM, less than 1.0 µM, less than 0.9 µM, less than 0.8 µM, less than 0.7 µM, less than 0.6 µM, less than 0.5 µM, less than 0.4 µM, less than 0.3 µM, less than 0.2 µM, less than 0.1 µM, less than 0.09 µM, less than 0.08 µM, less than 0.07 µM, less than 0.06 µM, less than 0.05 µM, less than 0.04 µM, less than 0.03 µM, less than 0.02 µM, less than 0.01 µM, or less than 0.005 µM. In an embodiment, the concentration of MG-132 is about 0.1 µM or 0.0625 µM.

In one embodiment, the inhibitor of protein degradation is epoxomicin. Concentrations of epoxomicin at 0.04-0.08 µM has been shown to inhibit chymotrypsin activity of the proteasome (Meng et al. 1999). In an embodiment, the concentration of epoxomicin suitable for the methods described herein is less than 0.08 µM, less than 0.07 µM, less than 0.06 µM, less than 0.05 µM, less than 0.04 µM, less than 0.03 µM, less than 0.02 µM, less than 0.01 µM, less than 0.009 µM, less than 0.008 µM, less than 0.007 µM, less than 0.006 µM, less than 0.005 µM, less than 0.004 µM, less than 0.003 µM, less than 0.002 µM, less than 0.001 µM, less than 0.009 µM, less than 0.008 µM, less than 0.007 µM, less than 0.006 µM, less than 0.005 µM, less than 0.004 µM, less than 0.003 µM, less than 0.002 µM, or less than 0.001 µM. In an embodiment, the concentration of epoxomicin is about 0.05 µM or 0.025 µM.

In one embodiment, the inhibitor of protein degradation is eeyarestatin I. The concentration of 8 µM eeyarestatin I has previously been shown in vivo to be sufficient to block ER translocation (Cross et al. 2009). In an embodiment, the concentration of eeyarestatin I suitable for the methods described herein is less than 20 µM, less than 15 µM, less than 14 µM, less than 13 µM, less than 12 µM, less than 11 µM, less than 10 µM, less than 9 µM, less than 8 µM, less than 7 µM, less than 6 µM, less than 5 µM, less than 4 µM, less than 3 µM, less than 2 µM, less than 1 µM, or less than 0.5 µM.

In any of the methods described herein for evaluation or identification of cells with certain characteristics, e.g., susceptibility to the inhibitors of protein degradation, one or more cells can be screened at the same time in a high throughput format. For example, cells can be grown in separate aliquots, e.g., in different wells of a multi-well plate, where each individual aliquot of cells is cultured or selected under different conditions. The different conditions can include different concentrations of the inhibitor of protein degradation, additional selection steps, or introduction of different exogenous nucleic acids. In such embodiments, comparison of a value of one or more parameter related to cell function determined from each aliquot can be used to identify, select, or classify a cell as a high producer, or as a cell for further development as a high production cell line.

Products and Nucleic Acids Encoding them

Provided herein are methods for identifying, selecting, or making a cell or cell line capable of producing high yields of a product. The products encompassed by the present disclosure include, but are not limited to, molecules, nucleic acids, polypeptides (e.g., recombinant polypeptides), or hybrids thereof, that can be produced by, e.g., expressed in, a cell. In some embodiments, the cells are engineered or modified to produce the product. Such modifications include the introducing molecules that control or result in production of the product. For example, a cell is modified by introducing an exogenous nucleic acid that encodes a polypeptide, e.g., a recombinant polypeptide, and the cell is cultured under conditions suitable for production, e.g., expression and secretion, of the polypeptide, e.g., recombinant polypeptide. In another example, a cell is modified by introducing an exogenous nucleic acid that controls, e.g., increases, expression of a polypeptide that is endogenously expressed by the cell, such that the cell produces a higher level or quantity of the polypeptide than the level or quantity that is endogenously produced, e.g., in an unmodified cell.

In embodiments, the cell or cell line identified, selected, or generated by the methods described herein produces a product, e.g., a recombinant polypeptide, useful in the treatment of a medical condition, disorder or disease. Examples of medical conditions, disorders or diseases include, but are not limited to, metabolic disease or disorders (e.g., metabolic enzyme deficiencies), endocrine disorders (e.g., hormone deficiencies), haemostasis, thrombosis, hematopoietic disorders, pulmonary disorders, gastro-intestinal disorders, immunoregulation (e.g., immunodeficiency), infertility, transplantation, cancer, and infectious diseases.

In some embodiments, the product is an exogenous protein, e.g., a protein that is not naturally expressed by the cell. The product can be a therapeutic protein or a diagnostic protein, e.g., useful for drug screening. The therapeutic or diagnostic protein can be an antibody molecule, e.g., an antibody or an antibody fragment, a fusion protein, a hormone, a cytokine, a growth factor, an enzyme, a glycoprotein, a lipoprotein, a reporter protein, a therapeutic peptide, or a structural and/or functional fragment or hybrid of any of these.

In one embodiment, the product, e.g., recombinant polypeptide, is an antibody molecule. Products encompassed herein comprise diagnostic and therapeutic antibody molecules. A diagnostic antibody molecule includes an antibody, e.g., a monoclonal antibody or antibody fragment thereof, useful for imaging techniques. A therapeutic antibody molecule is suitable for administration to subjects, e.g., for treatment or prevention of a disease or disorder.

An antibody molecule is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

Exemplary products, e.g., polypeptides, e.g., recombinant polypeptides, produced in the methods or cells described herein are provided in the tables below.

TABLE 1

Exemplary Products

| Therapeutic Product type | Product | Trade Name |
| --- | --- | --- |
| Hormone | Erythropoietin, Epoein-α | Epogen, Procrit |
|  | Darbepoetin-α | Aranesp |
|  | Growth hormone (GH), somatotropin | Genotropin, Humatrope, Norditropin, NovIVitropin, Nutropin, Omnitrope, Protropin, Siazen, Serostim, Valtropin |
|  | Human follicle-stimulating hormone (FSH) | Gonal-F, Follistim |
|  | Human chorionic gonadotropin | Ovidrel |
|  | Lutropin-α | Luveris |
|  | Glucagon | GlcaGen |
|  | Growth hormone releasing hormone (GHRH) | Geref |
|  | Secretin | ChiRhoStim (human peptide), SecreFlo (porcine peptide) |
|  | Thyroid stimulating hormone (TSH), thyrotropin | Thyrogen |
| Blood Clotting/Coagulation Factors | Factor VIIa | NovoSeven |
|  | Factor VIII | Bioclate, Helixate, Kogenate, Recombinate, ReFacto |
|  | Factor IX | Benefix |
|  | Antithrombin III (AT-III) | Thrombate III |
|  | Protein C concentrate | Ceprotin |
| Cytokine/Growth factor | Type I alpha-interferon | Infergen |
|  | Interferon-αn3 (IFNαn3) | Alferon N |
|  | Interferon-β1a (rIFN-β) | Avonex, Rebif |
|  | Interferon-β1b (rIFN-β) | Betaseron |
|  | Interferon-γ1b (IFN γ) | Actimmune |
|  | Aldesleukin (interleukin 2(IL2), epidermal theymocyte activating factor; ETAF | Proleukin |
|  | Palifermin (keratinocyte growth factor; KGF) | Kepivance |
|  | Becaplemin (platelet-derived growth factor; PDGF) | Regranex |
|  | Anakinra (recombinant IL1 antagonist) | Anril, Kineret |

TABLE 1-continued

Exemplary Products

| Therapeutic Product type | Product | Trade Name |
|---|---|---|
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In another embodiment, the product is a bispecific molecule. Bispecific molecules, as described herein, include molecules that can bind to two or more distinct antigens or targets. In an embodiment, a bispecific molecule comprises antibody fragments. In one embodiment, the bispecific molecule comprises a bispecific antibody, a bispecific antibody fusion protein, or a bispecific antibody conjugate, a Bi-specific T cell Engager (BiTE) molecule, a Dual Affinity Re-Targeting (DART) Molecule, a Dual Action Fab (DAF) molecule, a nanobody, or other arrangement of antibody fragments resulting in a molecule having the ability to recognize or bind to two distinct antigens.

TABLE 2

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |

TABLE 2-continued

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase I | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |

TABLE 2-continued

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

Other exemplary therapeutic or diagnostic proteins include, but are not limited to any protein described in Tables 1-10 of Leader et al., "Protein therapeutics: a summary and pharmacological classification", Nature Reviews Drug Discovery, 2008, 7:21-39 (incorporated herein by reference); or any conjugate, variant, analog, or functional fragment of the recombinant polypeptides described herein.

Other recombinant products include non-antibody scaffolds or alternative protein scaffolds, such as, but not limited to: DARPins, affibodies and adnectins. Such non-antibody scaffolds or alternative protein scaffolds can be engineered to recognize or bind to one or two, or more, e.g., 1, 2, 3, 4, or 5 or more, different targets or antigens.

Also provided herein are nucleic acids, e.g., exogenous nucleic acids that encode the products, e.g., polypeptides, e.g., recombinant polypeptides described herein. The nucleic acid sequences coding for the desired recombinant polypeptides can be obtained using recombinant methods known in the art, such as, for example by screening libraries from cells expressing the desired nucleic acid sequence, e.g., gene, by deriving the nucleic acid sequence from a vector known to include the same, or by isolating directly from cells and tissues containing the same, using standard techniques. Alternatively, the nucleic acid encoding the recombinant polypeptide can be produced synthetically, rather than cloned. Recombinant DNA techniques and technology are highly advanced and well established in the art. Accordingly, the ordinarily skilled artisan having the knowledge of the amino acid sequence of a recombinant polypeptide described herein can readily envision or generate the nucleic acid sequence that would encode the recombinant polypeptide.

In some embodiments, the exogenous nucleic acid controls the expression of a product that is endogenously expressed by the host cell. In such embodiments, the exogenous nucleic acid comprises one or more nucleic acid sequences that increase the expression of the endogenous product (also referred to herein as "endogenous product transactivation sequence"). For example, the nucleic acid sequence that increases the expression of an endogenous product comprises a constitutively active promoter or a promoter that is stronger, e.g., increases transcription at the desired site, e.g., increases expression of the desired endogenous gene product. After introduction of the exogenous nucleic acid comprising the endogenous product transactivation sequence, said exogenous nucleic acid is integrated into the chromosomal genome of the cell, e.g., at a preselected location proximal to the genomic sequence encoding the endogenous product, such that the endogenous product transactivation sequence increases the transactivation or expression of the desired endogenous product. Other methods for modifying a cell, e.g., introducing an exogenous nucleic acid, for increasing expression of an endogenous product is described, e.g., in U.S. Pat. No. 5,272,071; hereby incorporated by reference in its entirety.

The expression of a product described herein is typically achieved by operably linking a nucleic acid encoding the recombinant polypeptide or portions thereof to a promoter, and incorporating the construct into an expression vector. The vectors can be suitable for replication and integration eukaryotes or prokaryotes. Typical cloning vectors contain other regulatory elements, such as transcription and translation terminators, initiation sequences, and promoters useful for regulation of the expression of the desired nucleic acid sequence.

The nucleic acid sequences described herein encoding a product, e.g., a recombinant polypeptide, or comprising a nucleic acid sequence that can control the expression of an endogenous product, can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In embodiments, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193). Vectors derived from viruses are suitable tools to achieve long-term gene transfer since they allow long-term, stable integration of a transgene and its propagation in daughter cells.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection, e.g., a selection marker or a reporter gene.

In one embodiment, the vector comprising a nucleic acid sequence encoding a polypeptide, e.g., a LMM or a recombinant polypeptide, further comprises a promoter sequence responsible for the recruitment of polymerase to enable transcription initiation for expression of the polypeptide, e.g., the LMM or recombinant polypeptide. In one embodiment, promoter sequences suitable for the methods described herein are usually associated with enhancers to drive high amounts of transcription and hence deliver large copies of the target exogenous mRNA. In an embodiment, the promoter comprises cytomegalovirus (CMV) major immediate early promoters (Xia, Bringmann et al. 2006) and the SV40 promoter (Chernajovsky, Mory et al. 1984), both derived from their namesake viruses or promoters derived therefrom. Several other less common viral promoters have been successfully employed to drive transcription upon inclusion in an expression vector including Rous Sarcoma virus long terminal repeat (RSV-LTR) and Moloney murine leukaemia virus (MoMLV) LTR (Papadakis, Nicklin et al. 2004). In another embodiment, specific endogenous mammalian promoters can be utilized to drive constitutive transcription of a gene of interest (Pontiller, Gross et al. 2008). The CHO specific Chinese Hamster elongation factor 1-alpha (CHEF1a) promoter has provided a high yielding alternative to viral based sequences (Deer, Allison 2004). In addition to promoters, the vectors described herein further comprise an enhancer region as described above; a specific nucleotide motif region, proximal to the core promoter, which can recruit transcription factors to upregulate the rate of transcription (Riethoven 2010). Similar to promoter sequences, these regions are often derived from viruses and are encompassed within the promoter sequence such as hCMV and SV40 enhancer sequences, or may be additionally included such as adenovirus derived sequences (Gaillet, Gilbert et al. 2007).

In one embodiment, the vector comprising a nucleic acid sequence encoding a product, e.g., a polypeptide, e.g, a recombinant polypeptide, described herein further comprises a nucleic acid sequence that encodes a selection marker. In one embodiment, the selectable marker comprises glutamine synthetase (GS); dihydrofolate reductase (DHFR) e.g., an enzyme which confers resistance to methotrexate (MTX); or an antibiotic marker, e.g., an enzyme that confers resistance to an antibiotic such as: hygromycin, neomycin (G418), zeocin, puromycin, or blasticidin. In another embodiment, the selection marker comprises or is compatible with the Selexis® selection system (e.g., SUREtechnology Platform™ and Selexis Genetic Elements™ commercially available from Selexis® SA) or the Catalant selection system.

In one embodiment, the vector comprising a nucleic acid sequence encoding a recombinant product described herein comprises a selection marker that is useful in identifying a cell or cells comprise the nucleic acid encoding a recombinant product described herein. In another embodiment, the selection marker is useful in identifying a cell or cells that comprise the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

Suitable vectors for use are commercially available, and include vectors associated with the GS Expression System™, GS Xceed™ Gene Expression System, or Potelligent® CHOK1SV technology available from Lonza Biologics, Inc, e.g., vectors as described in Fan et al., *Pharm. Bioprocess.* (2013); 1(5):487-502, which is incorporated herein by reference in its entirety. GS expression vectors comprise the GS gene, or a functional fragment thereof (e.g., a GS mini-gene), and one or more, e.g., 1, 2, or 3, or more, highly efficient transcription cassettes for expression of the gene of interest, e.g., a nucleic acid encoding a recombinant polypeptide described herein. A GS mini-gene comprises, e.g., consists of, intron 6 of the genomic CHO GS gene. In one embodiment, a GS vector comprises a GS gene operably linked to a SV40L promoter and one or two polyA signals. In another embodiment, a GS vector comprises a GS gene operably linked to a SV40E promoter, SV40 splicing and polyadenylation signals. In such embodiments, the transcription cassette, e.g., for expression of the gene of interest or recombinant polypeptide described herein, includes the hCMV-MIE promoter and 5' untranslated sequences from the hCMV-MIE gene including the first intron. Other vectors can be constructed based on GS expression vectors, e.g., wherein other selection markers are substituted for the GS gene in the expression vectors described herein.

Vectors suitable for use in the methods described herein include, but are not limited to, other commercially available vectors, such as, pcDNA3.1/Zeo, pcDNA3.1/CAT, pcDNA3.3TOPO (Thermo Fisher, previously Invitrogen); pTarget, HaloTag (Promega); pUC57 (GenScript); pFLAG-CMV (Sigma-Aldrich); pCMV6 (Origene); pEE12 or pEE14 (Lonza Biologics), or pBK-CMV/pCMV-3Tag-7/pCMV-Tag2B (Stratagene).

Cells and Cell Culture

In one aspect, the present disclosure relates to methods for evaluating, classifying, identifying, selecting, or making a cell or cell line that produces a product, e.g., a recombinant polypeptide as described herein. In another aspect, the present disclosure relates to methods and compositions for evaluating, classifying, identifying, selecting, or making a cell or cell line with improved, e.g., increased, productivity and product quality.

In embodiments, the cell is a mammalian cell. In other embodiments, the cell is a cell other than a mammalian cell. In an embodiment, the cell is from mouse, rat, Chinese hamster, Syrian hamster, monkey, ape, dog, horse, ferret, or cat. In embodiments, the cell is a mammalian cell, e.g., a human cell or a rodent cell, e.g., a hamster cell, a mouse cell, or a rat cell. In another embodiment, the cell is from a duck, parrot, fish, insect, plant, fungus, or yeast. In one embodiment, the cell is an Archaebacteria. In an embodiment, the cell is a species of Actinobacteria, e.g., *Mycobacterium tuberculosis*.

In one embodiment, the cell is a Chinese hamster ovary (CHO) cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1SV GS knockout cell (Lonza Biologics, Inc.). The CHO FUT8 knockout cell is, for example, the Potelligent® CHOK1 SV (Lonza Biologics, Inc.).

In another embodiment, the cell is a Hela, HEK293, HT1080, H9, HepG2, MCF7, Jurkat, NIH3T3, PC12, PER.C6, BHK (baby hamster kidney cell), VERO, SP2/0, NS0, YB2/0, YO, EB66, C127, L cell, COS, e.g., COS1 and COS7, QC1-3, CHOK1, CHOK1SV, Potelligent CHOK1SV, CHO GS knockout, CHOK1SV GS-KO, CHOS, CHO DG44, CHO DXB11, and CHOZN, or any cells derived therefrom. In one embodiment, the cell is a stem cell. In one embodiment, the cell is a differentiated form of any of the cells described herein. In one embodiment, the cell is a cell derived from any primary cell in culture.

In an embodiment, the cell is any one of the cells described herein that comprises an exogenous nucleic acid encoding a recombinant polypeptide, e.g., expresses a recombinant polypeptide, e.g., a recombinant polypeptide selected from Table 1 or 2.

In an embodiment, the cell culture is carried out as a batch culture, fed-batch culture, draw and fill culture, or a continuous culture. In an embodiment, the cell culture is a suspension culture. In one embodiment, the cell or cell culture is placed in vivo for expression of the recombinant polypeptide, e.g., placed in a model organism or a human subject.

In one embodiment, the culture media is free of serum. Serum-free and protein-free media are commercially available, e.g., Lonza Biologics.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4$^{th}$ edition, Wiley-Liss/N.Y., 2000.

Other suitable cultivation methods are known to the skilled artisan and may depend upon the recombinant polypeptide product and the host cell utilized. It is within the skill of an ordinarily skilled artisan to determine or optimize conditions suitable for the expression and production of the recombinant polypeptide to be expressed by the cell.

In one aspect, the cell or cell line comprises an exogenous nucleic acid that encodes a product, e.g., a recombinant polypeptide. In an embodiment, the cell or cell line expresses the product, e.g., a therapeutic or diagnostic product. Methods for genetically modifying or engineering a cell to express a desired polypeptide or protein are well known in the art, and include, for example, transfection, transduction (e.g., viral transduction), or electroporation.

Physical methods for introducing a nucleic acid, e.g., an exogenous nucleic acid or vector described herein, into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Chemical means for introducing a nucleic acid, e.g., an exogenous nucleic acid or vector described herein, into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In embodiments, the integration of the exogenous nucleic acid into a nucleic acid of the host cell, e.g., the genome or chromosomal nucleic acid of the host cell is desired. Methods for determining whether integration of an exogenous nucleic acid into the genome of the host cell has occurred can include a GS/MSX selection method. The GS/MSX selection method uses complementation of a glutamine auxotrophy by a recombinant GS gene to select for high-level expression of proteins from cells. Briefly, the GS/MSX selection method comprises inclusion of a nucleic acid encoding glutamine synthetase on the vector comprising the exogenous nucleic acid encoding the recombinant polypeptide product. Administration of methionine sulfoximine (MSX) selects cells that have stably integrated into the genome the exogenous nucleic acid encoding both the recombinant polypeptide and GS. As GS can be endogenously expressed by some host cells, e.g., CHO cells, the concentration and duration of selection with MSX can be optimized to identify high producing cells with stable integration of the exogenous nucleic acid encoding the recombinant polypeptide product into the host genome. The GS selection and systems thereof is further described in Fan et al., *Pharm. Bioprocess.* (2013); 1(5):487-502, which is incorporated herein by reference in its entirety.

Other methods for identifying and selecting cells that have stably integrated the exogenous nucleic acid into the host cell genome can include, but are not limited to, inclusion of a reporter gene on the exogenous nucleic acid and assessment of the presence of the reporter gene in the cell, and PCR analysis and detection of the exogenous nucleic acid.

In one embodiment, the cells selected, identified, or generated using the methods described herein are capable of producing higher yields of protein product than cells that are selected using only a selection method for the stable expression, e.g., integration of exogenous nucleic acid encoding the recombinant polypeptide. In an embodiment, the cells selected, identified, or generated using the methods described herein produce 2-fold, 3-fold, 4-fold, 5-fold, 6-fold, 7-fold, 8-fold, 9-fold, or 10-fold or more of the product, e.g., recombinant polypeptide, as compared to cells that were not contacted with an inhibitor of protein degradation, or cells that were only selected for stable expression, e.g., integration, of the exogenous nucleic acid encoding the recombinant polypeptide.

Evaluating, Classifying, Selecting, or Identifying a Cell

In one aspect, the disclosure features methods for evaluating a cell, e.g., a candidate cell, for capability of product production, e.g., recombinant polypeptide production. The results of such evaluation can provide information useful for selection or identification of cells for generating a cell or cell line that is a high production cell or cell line. In another embodiment, the responsive to the evaluation described herein, the cell or cell line can be classified, e.g., as a cell or cell line that has the capability of high production.

A high production cell or cell line is capable of producing higher yields of a recombinant polypeptide product than compared to a reference cell or a cell that has not been selected or generated by the methods described herein. In an embodiment, a high production cell line is capable of producing 25 mg/L, 50 mg/L, 100 mg/L, 200 mg/L, 300 mg/L, 400 mg/L, 500 mg/L, 600 g/L, 700 g/L, 800 g/L, 900 g/L, 1 g/L, 2 g/L, 3 g/L, 4 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, or 100 g/L or more of a product, e.g., a recombinant polypeptide product. In an embodiment, a high production cell line is produces 100 mg/L, 200 mg/L, 300 mg/L, 400 mg/L, 500 mg/L, 600 g/L, 700 g/L, 800 g/L, 900 g/L, 1 g/L, 2 g/L, 3 g/L, 4 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, or 100 g/L or more of a product, e.g., a recombinant polypeptide product. The quantity of product produced may vary depending on the cell type, e.g., species, and the recombinant polypeptide to be expressed. By way of example, a high production cell is capable of producing at least 1 g/L, 2 g/L, 5 g/L, 10 g/L, 15 g/L, 20 g/L, or 25 g/L or more of a recombinant polypeptide, e.g., as described herein.

In embodiments where the product is difficult to express, the high production cell may produce lower concentrations of products, e.g., less than 1 g/L, however, the productivity is higher or increased than that observed for cells that have not been contacted with an inhibitor of protein degradation. For example, the level, amount, or quantity of the product produced by the identified or selected cell is increased, e.g., by 1-fold, 2-fold, 3-fold, 4-fold, 5-fold, 6-fold, 7-fold, 8-fold, 9-fold, 10-fold, 20-fold, 50-fold, or 100-fold or more, as compared to the level, amount, or quantity produced by a cell that has not been contacted by the inhibitor of protein degradation.

The methods described herein for evaluating a cell include evaluating the effect of an inhibitor of protein degradation on one or more parameters related to cell function. Parameters related to cell function include, but are not limited to, cell survival, culture viability, the ability to proliferate, the ability to produce a product, and protein degradation. In embodiments, the value of the effect of an inhibitor of protein degradation on one or more parameters related to cell function is compared to a reference value, for determining the effect of the inhibitor on the parameter related to cell function, e.g., for determining whether contacting the cell with the inhibitor results in an increase or decrease in one of the parameters related to cell function. In one embodiment, a cell can be selected or identified for development as a cell production line in response to the determination of an increases or decrease in one or more of the parameters related to cell function. In one embodiment, a cell can be identified as a high production cell, e.g., a cell capable of producing higher yields of a product, in response to the determination of an increase or decrease in one or more of the parameters related to cell function.

In any of the embodiments described herein, the reference value can be the value of the effect of the inhibitor of protein degradation on a parameter related to cell function of a reference cell, e.g., a cell with a predetermined productivity. Alternatively or in addition, in any of the embodiments described herein, the reference value can be the value of the parameter related to cell function of the same cell being tested, where the cell has not been contacted with the inhibitor, e.g., the value of the parameter was measured before contacting the cell with the inhibitor of protein degradation, or a separate aliquot of the cell that has not been contacted with the inhibitor of protein degradation.

In one embodiment, cell survival can be measured by determining or quantifying cell apoptosis, e.g., the number or amount of cells that have been killed or died in response to a concentration of an inhibitor of protein degradation described herein. An increase in cell survival comprises a 1%, 2%, 5%, 10%, 20%, 30%, 40%, 50%, 60%, 70%, 80%, 90%, one-fold, two-fold, three-fold, four-fold, or five-fold or more increase in the number of cells, e.g., intact or live cells, remaining after contacting with the inhibitor of protein degradation. Alternatively, an increase in cell survival comprises a 1%, 2%, 5%, 10%, 20%, 30%, 40%, 50%, 60%, 70%, 80%, 90%, or more decrease in the number of apoptotic cells after contacting with the inhibitor of protein degradation. Methods for detecting cell survival or apoptosis are known in the art, e.g., Annexin V assays, and are described herein in the Examples.

In one embodiment, culture viability can be measured by determining or quantifying the number or amount of live cells, e.g., live cells in a culture or population of cell, or cells that have a characteristic related to viability, e.g., proliferation markers, intact DNA, or do not display apoptotic markers. An increase in culture viability comprises a 1%, 2%, 5%, 10%, 20%, 30%, 40%, 50%, 60%, 70%, 80%, 90%, one-fold, two-fold, three-fold, four-fold, or five-fold or more increase in the number of cells, e.g., intact or live cells, remaining after contacting with the inhibitor of protein degradation. Methods for determining culture viability are known in the art, and are described herein in Examples 1 and 3. Other methods for assessing culture viability include, but are not limited to, trypan blue exclusion methods followed by counting using a haemocytometer or Vi-CELL (Beckman-Coulter). Other methods for assessing culture viability can comprise determining viable biomass, and includes using radiofrequency impedance or capacitance (e.g., as described in Carvell and Dowd, 2006, Cytotechnology, 50:35-48), or using Raman spectroscopy (e.g., as described in Moretto et al., 2011, American Pharmaceutical Review, Vol. 14).

In one embodiment, the ability of a cell to proliferate can be measured by quantifying or counting the number of cells, cell doublings, or growth rate of the cells. Alternatively, proliferating cells can be identified by analysis of the genomic content of the cells (e.g., replicating DNA), e.g., by flow cytometry analysis, or presence of proliferation markers, e.g., Ki67, phosphorylated cyclin-CDK complexes involved in cell cycle. An increase in the ability to proliferate comprises a 1%, 2%, 5%, 10%, 20%, 30%, 40%, 50%, 60%, 70%, 80%, 90%, one-fold, two-fold, three-fold, four-fold, or five-fold or more increase in the number of cells, or number of cells expressing a proliferation marker, after contacting the cell with the inhibitor of protein degradation. Alternatively, an increase in the ability to proliferate comprises a 1%, 2%, 5%, 10%, 20%, 30%, 40%, 50%, 60%, 70%, 80%, 90%, one-fold, two-fold, three-fold, four-fold, or five-fold or more increase in the doubling or growth rate of the cells after contacting the cells with the inhibitor of protein degradation.

The methods provided herein are useful for identifying, selecting, or making a cell or cell line that has improved capacity for producing a recombinant polypeptide, e.g., a product. In one embodiment, the methods provided herein are also useful for identifying, selecting, or making a cell or cell line that produces an improved quality of the recombinant polypeptide.

In one embodiment, the ability of the cell to produce a product can be measured by determining or quantifying the amount or concentration of product that is produced. An increase in the ability to produce a product comprises a 1%, 2%, 5%, 10%, 20%, 30%, 40%, 50%, 60%, 70%, 80%, 90%, one-fold, two-fold, three-fold, four-fold, or five-fold or more increase in protein production after contacting the cell with the inhibitor of protein degradation.

In one embodiment, the quality of the product, e.g., expressed recombinant polypeptide, can be measured by determining or quantifying the amount or concentration of properly folded product, functional product, or non-aggregated product. An increase in the quality of the product produced by the cell comprises a 1%, 2%, 5%, 10%, 20%, 30%, 40%, 50%, 60%, 70%, 80%, 90%, one-fold, two-fold, three-fold, four-fold, or five-fold or more increase in the amount or concentration of properly folded product, functional product, or non-aggregated product, e.g., expressed recombinant polypeptide, after contacting the cell with the inhibitor of protein degradation.

Methods of measuring increased protein production are well-known to those skilled in the art. For example, an increase in recombinant protein production might be determined at small-scale by measuring the titer in tissue culture medium by ELISA (Smales et al. 2004 Biotechnology Bioengineering 88:474-488). It can also be determined quantitatively by the ForteBio Octet, for example for high throughput determination of recombinant monoclonal antibody (mAb) concentration in medium (Mason et al. 2012 Biotechnology Progress 28:846-855) or at a larger-scale by protein A HPLC (Stansfield et al. 2007 Biotechnology Bioengineering 97:410-424). Other methods for determining production of a product, e.g., a recombinant polypeptide described herein, can refer to specific production rate (qP) of the product, in particular the recombinant polypeptide in the cell and/or to a time integral of viable cell concentration (IVC). Recombinant polypeptide production or productivity, being defined as concentration of the polypeptide in the culture medium, is a function of these two parameters (qP and IVC), calculated according to Porter et al. (Porter et al. 2010 Biotechnology Progress 26:1446-1455). Methods for measuring protein production are also described in further detail in the Examples provided herein, e.g., Examples 1 and 5.

Methods for measuring improved quality of product produced by the cell lines generated as described herein are known in the art. In one embodiment, methods for determining the fidelity of the primary sequence of the expressed recombinant polypeptide product are known in the art, e.g., mass spectrometry. An increase in the amount or concentration of properly folded product, e.g., expressed recombinant polypeptide, can be determined by circular dichroism or assessing the intrinsic fluorescence of the expressed recombinant polypeptide. An increase in the amount or concentration of functional product can be tested using various functional assays depending on the identity of the recombinant polypeptide. For example, antibodies can be tested by the ELISA or other immunoaffinity assay.

Methods for Cell Line and Recombinant Polypeptide Production

The current state of the art in both mammalian and microbial selection systems is to apply selective pressure at the level of the transcription of DNA into RNA. The gene of interest is tightly linked to the selection marker making a high level of expression of the selective marker likely to result in the high expression of the gene of interest. Cells which express the selection marker at high levels are able to survive and proliferate, those which do not are less likely to survive and proliferate, e.g., apoptose and/or die. In this way a population of cells can be enriched for cells expressing the selection marker and by implication the gene of interest at high levels. This method has proved very successful for expressing straightforward proteins.

However, for some proteins the bottleneck for expression is not the transcription of DNA into RNA but rather the correct folding and if necessary posttranslational modifications of the protein. Current selection systems targeting transcription do not apply pressure for the selection of cell lines that are good at producing and correctly processing proteins. In fact high levels of transcription can exasperate problems with downstream protein synthesis steps by overloading the cells capacity to produce and process these proteins. The use of selection systems applying selective pressure at an alternative stage of protein production can greatly improve the stringency of selection. Such selection systems can be termed orthogonal selection systems because their mode of action is independent of the current state of the art selection systems operating at the level of gene transcription. These alternative selection systems may also operate independently of each other and hence be orthogonal to each other. For example selection systems targeting transcription, translation, posttranslational modification and secretion might all be independent of each other in mode of action. Orthogonal selection systems can be used together to increase the stringency of selection and to hit multiple targets in selection.

The current invention is an example of an orthogonal selection system, operating at the level of protein folding and posttranslational modification. However other example of orthogonal selection systems can be envisioned working on the same broad principle of inhibiting the growth of cells within the population that perform poorly in a step of protein expression downstream of transcription.

In one aspect, the disclosure provides methods for generating a cell or cell line for producing a product, e.g., a recombinant polypeptide. In another aspect, the disclosure provides methods for producing a product, e.g., a recombinant polypeptide described herein using a cell that is identified, classified, selected, or generated using the methods described herein. Any of the foregoing methods include evaluating, identifying, classifying, or selecting a cell as described herein, e.g., by contacting the cell with an inhibitor of protein degradation, to identify or make a cell that has the capacity for high production of a product, e.g., a recombinant polypeptide. The methods described herein increase the production, e.g., expression and/or secretion of a recombinant polypeptide.

Without wishing to be bound by theory, it is believed that cells capable of higher productivity are less susceptible to inhibitors of protein degradation, and therefore, it is believed that contacting the cells with an inhibitor of protein degradation comprising an exogenous nucleic acid described herein results in the selection for a cell capable of higher productivity.

In one aspect, utilization of two or more selection steps, e.g., selection for stable integration of the exogenous nucleic acid and selection for susceptibility for inhibition of protein degradation, results in higher producing cells and cell lines than cells generated by a single selection step. Accordingly, the present disclosure features a method for generating a high producing cell comprising:
  i) providing a cell that comprises an exogenous nucleic acid encoding a recombinant polypeptide product;
  ii) administering a first selective pressure, e.g., selection for a first property, e.g., selecting for cells having stable integration of the exogenous nucleic acid; and
  iii) administering a second selective pressure, e.g., performing a selection for a second property, e.g., selecting for cells having lower susceptibility to inhibition of protein degradation.

In embodiments, the first selective pressure is administered prior to, simultaneously with, or after the second selective pressure is administered. In one embodiment, the first selective pressure is administered prior to the second selective pressure. In one embodiment, the first selective pressure is completed prior to initiation of the second selective pressure. In one embodiment, the second selective pressure is administered prior to the first selective pressure. In one embodiment, the second selection pressure is completed prior to the initiation of the first selective pressure. In one embodiment, the first selection pressure and the second selection pressure is administered simultaneously. In one embodiment, the administration of the first and second selection pressure overlap fully or in part. In one embodiment, the second selection pressure is initiated 12 hours, 24 hours, 48 hours, 72 hours, 96 hours, or 168 hours or more prior to the completion of the first selection pressure. In one embodiment, the second selection pressure is initiated 12 hours, 24 hours, 48 hours, 72 hours, 96 hours, or 168 hours or more after the completion of the first selection pressure.

In an embodiment, the first selective pressure comprises selection for stable integration of the exogenous nucleic acid, e.g., a GS/MSX selection. In an embodiment, the second selective pressure comprises selection for susceptibility to inhibition of protein degradation comprises contacting the cells with an inhibitor of protein degradation. In an embodiment, an inhibitor of protein degradation is administered prior to, simultaneously with, or after a selection pressure comprising identification of cells comprising genomic integration of the exogenous nucleic acid. In an embodiment, the inhibitor of protein degradation is administered 12 hours, 24 hours, 48 hours, 72 hours, 96 hours, or 168 hours or more after the completion of a prior selection step to identify cells comprising genomic integration of the exogenous nucleic acid.

The selective pressures are applied in a manner to select for cells with improved capacity to produce recombinant polypeptides, and/or with ability to produce recombinant polypeptides with improved quality. In one embodiment, each selective pressure, e.g., a first and/or second selective pressure described herein, is applied for at least 24 hours, 48 hours, 72 hours, 96 hours, or 120 hours, or 168 hours. As described herein, the concentration of an inhibitor of protein degradation results in at least 20%, 25%, 30%, 35%, 40%, 45%, 50%, 55%, 60%, 65%, or 70% culture viability, e.g., at least 20%, 25%, 30%, 35%, 40%, 45%, 50%, 55%, 60%, 65%, or 70% of the number of cells remain, e.g., survive, after culturing in the presence of an inhibitor of protein degradation described herein. In some embodiments, the methods described herein, e.g., particularly after application of two or more selective pressures, results in less than 20%, e.g., 15%, 10%, 5%, 1%, 0.5%, 0.1%, or less, total cells remaining after the selection. The percentage of culture viability or cell survival after selection in the presence of an inhibitor of protein degradation described herein is determined as compared to the percentage of culture viability or cell survival in the absence of the presence of an inhibitor of protein degradation. The remaining viable cells after culture in the presence of inhibitor of protein degradation described herein can be further cultured to generate a cell line.

In embodiments, viable cells that remain after two selective pressures, e.g., selection for stable integrants comprising the exogenous nucleic acid and selection for low susceptibility to inhibitors to protein degradation, have increased capacity for protein production. For example, the cells having increased capacity for protein production produce 2-fold, 3-fold, 4-fold, 5-fold, 6-fold, 7-fold, 8-fold, 9-fold, or 10-fold or more, or at least 1%, 2%, 5%, 10%, 20%, 30%, 40%, 50%, 60%, 70%, 80%, 90%, 100% or more of a product, e.g., a recombinant polypeptide, as compared to cells that were only administered one selective pressure or were not administered any selective pressure.

In embodiments, viable cells that remain after two selective pressures as described herein, produce an improved quality of the expressed recombinant polypeptide. For example, the improved quality of the product comprises one or more of: a more homogeneous product, an increased proportion of properly folded expressed recombinant polypeptides, or an increased proportion of functional recombinant polypeptides, a reduced proportion of aggregated recombinant polypeptides. For example, the cells producing improved quality of the product produce 2-fold, 3-fold, 4-fold, 5-fold, 6-fold, 7-fold, 8-fold, 9-fold, or 10-fold or more, or at least 1%, 2%, 5%, 10%, 20%, 30%, 40%, 50%, 60%, 70%, 80%, 90%, 100% or more, properly folded or functional recombinant polypeptides, as compared to cells that were only administered one selective pressure or were not administered any selective pressure.

In one embodiment, the methods used herein for generating a cell line with improved production capacity or improved quality of the produced product are useful with pre-existing or commercially available cell lines that express a recombinant polypeptide described herein, e.g., selected from Table 1 or 2. In such methods, the cells are cultured in the presence of an effective concentration of an inhibitor of protein degradation described herein suitable to identify cells with improved production capacity or improved quality of product, e.g., the concentration of an inhibitor of protein degradation that results in at least 20%, 25%, 30%, 35%, 40%, 45%, 50%, 55%, 60%, 65%, or 70% culture viability, e.g., at least 20%, 25%, 30%, 35%, 40%, 45%, 50%, 55%, 60%, 65%, or 70% of the number of cells remain, e.g., survive, after culturing in the presence of an inhibitor of protein degradation described herein. In some embodiments, the culturing cells in the presence of an inhibitor of protein degradation described herein results in less than 20%, e.g., 15%, 10%, 5%, 1%, 0.5%, 0.1%, or less, total cells remaining after the culturing in the presence of an inhibitor of protein degradation described herein. The remaining viable cells after culture in the presence of inhibitor of protein degradation described herein can be further cultured to generate a cell line, e.g., an improved cell line.

In some embodiments, additional steps may be performed to improve the expression of the product, e.g., transcription, translation, and/or secretion of the product, or the quality of the product, e.g., proper folding and/or fidelity of the primary sequence. Such additional steps include introducing an agent that improves product expression or product quality. In an embodiment, an agent that improves product expression or product quality can be a small molecule, a polypeptide, or a nucleic acid that encodes a polypeptide that improves protein folding, e.g., a chaperone protein. In one embodiment, the nucleic acid comprises an inhibitory nucleic acid, e.g., a microRNA or a lncRNA. In an embodiment, the agent that assists in protein folding comprises a nucleic acid that encodes a chaperone protein, e.g., BiP, PD1, or ERO1 (Chakravarthi & Bulleid 2004; Borth et al. 2005; Davis et al. 2000). Other additional steps to improve yield and quality of the product include overexpression of transcription factors such as SBP1 and ATF6 (Tigges & Fussenegger 2006; Cain et al. 2013; Ku et al. 2008) and of lectin binding chaperone proteins such as calnexin and calreticulin (Chung et al. 2004). Overexpression of the agents that assist or improve protein folding and product quality and yield proteins described herein can be achieved by introduction of exogenous nucleic acids encoding the proteins. In another embodiment, the agent that improves product expression or product quality is a small molecule that can be added to the cell culture to increase expression of the product or quality of the product. In one embodiment, culture of the cells at a lower temperature, e.g., 1° C., 2° C., 3° C., 4° C., 5° C., 6° C., 7° C., 8° C., 9° C., or 10° C. lower, than the temperature that the cells are normally grown in.

Any of the methods described herein can further include additional selection steps for identifying cells that have high productivity or produce high quality products. For example, FACS selection can be utilized to select and isolate specific cells with desired characteristics, e.g., higher expression of protein folding proteins, e.g., chaperones; or improved expression of the product.

In one aspect, the disclosure provides methods that include a step for recovering or retrieving the recombinant polypeptide product. In embodiments where the recombinant polypeptide is secreted from the cell, the methods can include a step for retrieving, collecting, or separating the recombinant polypeptide from the cell, cell population, or the culture medium in which the cells were cultured. In embodiments where the recombinant polypeptide is within the cell, the purification of the recombinant polypeptide product comprises separation of the recombinant polypeptide produced by the cell from one or more of any of the following: host cell proteins, host cell nucleic acids, host cell lipids, and/or other debris from the host cell.

In embodiments, the process described herein provides a substantially pure protein product. As used herein, "substantially pure" is meant substantially free of pyrogenic materials, substantially free of nucleic acids, and/or substantially free of endogenous cellular proteins enzymes and components from the host cell, such as polymerases, ribosomal proteins, and chaperone proteins. A substantially pure protein product contains, for example, less than 25%, 20%, 15%, 10%, 9%, 8%, 7%, 6%, 5%, 4%, 3%, 2%, or 1% of contaminating endogenous protein, nucleic acid, or other macromolecule from the host cell.

Methods for recovering and purification of a product, e.g., a recombinant polypeptide, are well established in the art. For recovering the recombinant polypeptide product, a physical or chemical or physical-chemical method is used. The physical or chemical or physical-chemical method can be a filtering method, a centrifugation method, an ultracentrifugation method, an extraction method, a lyophilization method, a precipitation method, a crystallization method, a chromatography method or a combination of two or more methods thereof. In an embodiment, the chromatography method comprises one or more of size-exclusion chromatography (or gel filtration), ion exchange chromatography, e.g., anion or cation exchange chromatography, affinity chromatography, hydrophobic interaction chromatography, and/or multimodal chromatography.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Methods

The methods and assays provided in this example are related to evaluating the effect of an inhibitor of protein degradation on a parameter related to cell function, e.g., cell survival and culture viability. These methods and assays were used for the experiments described in the following examples.

Inhibitor Kill Curves in the 96DWP Format 96 deep well plates (Nunc) were seeded at $4 \times 10^6$ cells/ml at 300 µl per well for analysis of proteasome and ERAD inhibitors. Triplicate wells were prepared for each inhibitor for each of the panel of cell lines. 1 µl of each inhibitor stock was added to each well to give a final concentration of 0.05 µM epoxomicin, 0.5 µM MG-132 and 10 µM eeyarestatin I. Plates were incubated at 36.5° C. with 5% CO2 and 90% humidity with 375 rpm shake speed until appropriate 24 hour time-points. 100 µl of the well volume was combined with 900 µl PBS and a cell count performed using the ViCell apparatus. The remaining 200 µl was centrifuged at 1000 rpm for 5 minutes and the supernatant and pellet stored at −20° C. prior to further analysis.

Proteasome Activity Analysis

Cell pellets were prepared at 5×106 cells from the required cell lines by centrifugation of the required culture volume at 1000 rpm for five minutes. The pellet was then stored at −20° C. until activity assessment was performed. The pellet was resuspended in lysis buffer (20 mM HEPES NaOH pH 7.2, 100 mM NaCl, 10 mM Na β-glycerophosphate, 0.5% w/v Triton X-100). A Bradford assay was then performed to determine the total protein in the lysate material, and the required volume to obtained 100 µg total protein for each reaction was calculated. Multiple pellets were pooled where required to ensure sufficient material for the activity probe assessment and the subsequent inhibitor challenge. The Bradford assay was repeated for the pooled material. 100 µg protein was combined with 1 µl of probe or DMSO and the reaction volume made up to 200 µl with lysis buffer. Mixtures were vortexed and left to shake at room temperature for 1 hour in the dark (wrapped in foil). 1 ml of ice cold 100% acetone was then added, vortexed and then spun at 13000 rpm for 5 minutes. Acetone was removed and the pellet resuspended in 20 µl 2×SDS sample buffer. Samples were heated at 95° C. for 5 minutes with occasional shaking, before brief centrifugation at 13000 rpm and then storage at −20° C. prior to further analysis. The inhibitor challenge with epoxomicin was repeated on the samples from the same lysate material. Reaction mixes were prepared in the same manner as before with 100 µg of protein and 1 µl of probe with a final reaction volume of 200 µl. However, prior to the addition of the probe to the reaction, 1 µl of epoxomicin at 50 µM or 20 µM were added and the reactions incubated with shaking at room temperature for 30 minutes in the dark. Following the pre-incubation with the inhibitor, the probe was added and the reaction continued as before for the activity probe assessment. Samples were prepared using acetone precipitation as before and stored at −20° C. until analysis was performed. The 20 µl volume was loaded onto 14% SDS-PAGE resolving gels with a 5% stacking gel. Prior to loading gel samples were re-heated at 95° C. for 5 minutes and briefly centrifuged at 13,000 rpm. Gels were run at 200 V for approximately 1 hour until complete. Gels were then analyzed for fluorescence using the Typhoon 9400. The RUB1001 probe used the Cy2 analysis (Filter: 520BP40, Laser: Blue 2 (488 nm), sensitivity: normal). Probes MV151, MVB003, MVB072, RUB1018 and no probe used the Cy3 analysis (Filter: 580BP30, Laser: Green (532 nm), sensitivity: normal), with a typical image resolution of 100 microns and 600 PMT. After fluorescence analysis, gels were placed in Coomassie stain overnight and placed in de-stain the following day to provide a loading control of the total protein.

Polyclonal Stable Pool Generation for Cell Line Construction Experiment

The electroporation was performed in the GSKO suspension cell line. A count was performed of the culture in mid exponential phase and the remaining culture centrifuged at 1000 rpm and the supernatant removed. 1×10$^7$ cells were required per electroporation cuvette in a volume of 700 µl. Therefore, the pellet was resuspended to achieve the concentration of cells for the number of electroporations required. Electroporations were performed with 20 µg linearized plasmid at 300 V, a capacitance of 900 µF and using cuvettes with a 4 mm gap. Each cuvette was added to 20 ml of fresh media with 2 ml of that volume used to rinse out the cuvette. For the cell line construction experiment, then all electroporations were pooled together to give a final volume of 300 ml. This was thoroughly mixed and then distributed in 10 ml volumes between 30×T75 tissue culture flasks. The flasks were then incubated statically at 36.5° C. with 5% $CO_2$. 24 hours after the transfection, the glutamine synthetase inhibitor (MSX) was added to provide selection of the cells successfully taking up the plasmid and expressing the selection marker GS. 5 ml volumes of the MSX stocks with CD-CHO media were added to give either a final culture concentration of either 25, 37.5 or 50 µM MSX. The addition of the proteasome inhibitors was then performed at the appropriate time-point following MSX selection as determined by the design of experiments layout detailed in Table 3. Filter sterilized DMSO was added as a control where no drug was required in the combinations. Cultures were then incubated statically at 36.5° C. and 5% $CO_2$ for approximately two weeks following addition of MSX. Viability counts were performed if cultures were observed to increase in cell concentration or at least once a week. Once a viable cell concentration of at least 0.2×10$^6$ cells/ml was achieved, the cultures were moved into 20 ml shake flask cultures at 36.5° C. and 5% $CO_2$ with shaking at 140 rpm. From this point onwards routine sub-culture was performed every 3-4 days.

TABLE 3

In Vitro Optimal Response Surface Design

| Run | Time of proteasome inhibitor addition post MSX (hours) | Concentration of MG-132 (µM) | Concentration of Epoxomicin (µM) | Concentration of MSX (µM) |
|---|---|---|---|---|
| 1 | 24 | 0.0625 | 0.025 | 37.5 |
| 2 | 168 | 0 | 0 | 37.5 |
| 3 | 168 | 0.125 | 0 | 37.5 |
| 4 | 96 | 0.0625 | 0.05 | 37.5 |
| 5 | 96 | 0.0625 | 0.05 | 37.5 |
| 6 | 24 | 0 | 0 | 37.5 |
| 7 | 24 | 0.125 | 0 | 50 |
| 8 | 96 | 0 | 0.025 | 37.5 |
| 9 | 96 | 0.0625 | 0.025 | 50 |
| 10 | 96 | 0.125 | 0.025 | 37.5 |
| 11 | 96 | 0.0625 | 0 | 37.5 |
| 12 | 24 | 0.125 | 0 | 25 |
| 13 | 24 | 0.125 | 0.025 | 37.5 |
| 14 | 24 | 0.0625 | 0 | 37.5 |
| 15 | 168 | 0 | 0 | 50 |
| 16 | 24 | 0.0625 | 0.025 | 50 |
| 17 | 168 | 0.125 | 0.05 | 50 |
| 18 | 96 | 0 | 0.025 | 37.5 |
| 19 | 168 | 0.0625 | 0.025 | 37.5 |
| 20 | 24 | 0 | 0.05 | 25 |
| 21 | 96 | 0.0625 | 0.025 | 25 |
| 22 | 24 | 0 | 0.05 | 50 |
| 23 | 96 | 0.0625 | 0.025 | 50 |
| 24 | 168 | 0 | 0.05 | 37.5 |
| 25 | 168 | 0.0625 | 0.025 | 37.5 |
| 26 | 24 | 0.125 | 0.05 | 37.5 |
| 27 | 168 | 0 | 0 | 25 |
| 28 | 168 | 0.125 | 0.05 | 25 |
| 29 | 24 | 0.0625 | 0.05 | 25 |
| 30 | 96 | 0.0625 | 0.025 | 25 |

Enzyme-Linked Immunosorbent Assay (ELISA) of Supernatant Samples to Determine Antibody Concentration AffiniPure F(ab')2 fragment goat anti-human IgG Fc fragment specific (minimal cross-reaction to bovine, horse, mouse serum proteins) (Jackson ImmunoResearch Laboratories Inc) was diluted in coating buffer (15 mM $Na_2CO_3$ and 35 mM $NaHCO_3$, pH 9.7) to give a concentration of 2.2 m/ml. 100 µl of the stock was then used to coat each well of 96 well plate (Nunc). Plates were covered with foil and stored at 4° C. overnight. Plates were washed twice in wash buffer (0.1 M NaCl, 8.1 mM $Na_2HPO_4$, 2.4 mM $NaH_2PO_4.H_2O$, 12.7 mM EDTA, 0.02% v/v Tween-20 and 1% L-butanol, pH 7.2) before adding 200 µl block solution (0.5% w/v Casein in 15 mM $Na_2CO_3$ and 35 mM $NaHCO_3$, pH 9.7) to each well and incubating with shaking at room temperature for 1 hour. IgG standards of Human IgG reagent grade (Sigma) were prepared by serial dilution in sample buffer (0.1 M Tris-HCl, 0.1 M NaCl and 0.02% v/v Tween-20, pH 7.0) to give a range between 250 ng/ml and 3.9 ng/ml. Serial dilutions of the supernatant samples in sample buffer were also performed. Following blocking, plates were washed twice in wash buffer, before 100 µl of sample/standard were added to the relevant wells. Plates were then incubated with shaking at room temperature for a further hour. Plates were washed twice before addition of 100 µl/well of the secondary antibody solution (Anti-human kappa light chain (bound and free) HRP conjugate raised in goat (Sigma) diluted 1:10000 in wash buffer). Following addition of the secondary antibody plates were incubated with shaking at room temperature for one hour. Plates were again washed and ready-made TMB substrate (Cell signalling technology #7004) was added (100 µl/well). Once a significant blue colouration of the standards had occurred, the reaction was stopped using 50 µl/well of 2.5 M $H_2SO_4$. The optical density of each well was then measured at 450 nm. The concentration of the supernatant samples were then determined from the standard curve of the known concentrations of IgG.

Protein a High Performance Liquid Chromatography to Determine Antibody Concentration HPLC was performed with a Protein A column using Chemstation software and Agilent 1260 instrument following Lonza standard operating procedures. A Protein A HPLC standard (lot no L27336/07/02) at a concentration of 1008 mg/L was used, diluted 1 in 2 with binding buffer. A generic IAC (lot no L27336/7/1) at a concentration of 3700 mg/L was also used, diluted 1 in 10 with binding buffer, to provide a control. IAC results were found to be within the set limits required by the protocol. Supernatant samples were diluted 1 in 2 with binding buffer before running on the column.

Example 2: Determination of Appropriate Concentrations to Determine Susceptibility of Cell Lines to Different Inhibitors Initial assessment was performed across two experiments using one model recombinant CHO antibody producing cell line (CH0149) to determine the appropriate concentrations of each inhibitor to use for the assessment of the full panel (FIGS. 1A-1C and 2A-2F). A range of concentrations were analyzed based around those concentrations previously reported and used in the literature; 8 µM eeyarestatin has previously been shown in vivo to be sufficient to block ER translocation (Cross et al. 2009); 0.04-0.08 µM epoxomicin has been shown to inhibit chymotrypsin activity of the proteasome (Meng et al. 1999); 1.5 µM MG-132 has been shown to induce apoptosis (Meriin et al. 1998).

Following incubation of the CH0149 cell line with 0.5 and 1 µM MG-132, the effects observed were almost the same with a reduction in the culture viability to approximately 50% and an approximate decrease in the viable cell number by 40% 48 hours after the addition of the drug compared to the control samples (FIGS. 2A-2F). A concentration of 0.1 µM MG-132 resulted in less of an effect on culture viability and cell numbers whilst the effects produced by 5 and 10 µM concentrations were severe with both cell numbers and culture viability dramatically reduced 48 hours after addition of the drug (FIGS. 1A-1C and 2A-2F).

Concentrations of 0.5 and 1 µM epoxomicin resulted in a 90% decrease in viable cell number 48 hours after addition of the drug (FIGS. 1A-1C), whereas concentrations of 0.01, 0.005 and 0.001 µM resulted in an increase in viable cell number, with the drug not showing any detrimental effects until 72 hours after addition of the drug (FIGS. 2A-2F). A concentration of 0.05 µM epoxomicin resulted in a drop in culture viability ranging from 30-60% and a decrease in viable cell numbers of 30-50% across the two experiments by 48 hours after addition of the drug (FIGS. 1A-1C and 2A-2F).

The addition of the inhibitor eeyarestatin I resulted in varying effects across the two experiments, leading to a decrease in viable cell number ranging from 15-30% at 48 hours after addition at a concentration of 1 µM. A concentration of 10 µM consistently showed an effect on the culture viability parameters across the two experiments, though the magnitude of the effect was large. Based on the results in FIGS. 1A-1C and 2A-2F, the concentrations determined for further studies were 0.5 µM for MG-132, 0.05 µM for epoxomicin and 10 µM eeyarestatin I. At these concentrations an effect on cell concentration and culture viability was observed at a 30-60% reduction compared to the control samples.

Example 3: Assessment of ERAD and Proteasome Inhibitors Across a Panel of Production Cell Lines Using the concentrations of inhibitors as determined in Example 2, the effects of the inhibitors at the set concentrations were investigated on a panel of CHO mAb producing cell lines. All of the cell lines used were derived from a CHOK1SV host cell line and were expressing the model IgG4 molecule at different yields. The productivities of the cell lines had previously been determined and these historical titers were used to select a panel covering a range of productivities to determine susceptibility to the inhibitors. The cells were then assessed upon addition of the inhibitors in a 96 deep well plate format with daily cell counts being undertaken after addition of the inhibitors.

Culture viabilities and viable cell numbers varied between cell lines of differing productivities following 48 hours of culture. The largest magnitude of effect of the inhibitors was observed 48 hours post addition and therefore this timepoint was used to perform the correlation analysis.

The effects of the drugs on the viability of the cell lines were compared to the productivity of the cells to determine if strong correlations were present between productivity and susceptibility to the drug concentrations investigated. Historical preproduction data for product concentration and specific production rate from fed batch and bioreactor data were used to perform correlation analysis with the effects of the inhibitors in the 96 DWP format using linear regression and Pearson's correlation analysis. Statistically significant correlations ($p<0.05$) were determined between the cell line productivities and the susceptibility to the proteasome inhibitors.

After 48 hours in the presence of 0.5 µM MG-132, a positive correlation was determined between viable cell concentration and the specific production rate determined from fed-batch culture as well as between the culture viability and the specific production rate determined from fed-batch and bioreactor culture (FIGS. 3A-3D and 6A-6G; and Table 4). When the cells were cultured in the presence of 0.05 µM epoxomicin, once again there was a positive correlation between viable cell number and the specific production rate determined from fed-batch and bioreactor culture, as well as between viable cell number and the product concentration determined from fed-batch and bioreactor culture (FIGS. 4A-4D and 6A-6G; and Table 4). No statistically significant correlations were determined between culture viability and productivity data with 0.05 µM epoxomicin. There were also no significant correlations between cell culture parameters and productivity characteristics when the cells were cultured in the presence of Eeyarestatin I.

TABLE 4

Summary of correlation coefficients of inhibitor effects on the culture viability and viable cell concentrations of the model CHO antibody producing cell lines with the productivity of the cell lines. (Asterisks (*) indicate statistically significant correlations).

| Cell Culture Parameter | Fed Batch Antibody Concentration (mg/L) | | Fed Batch Specific Production Rate (pg/cell/h) | | Bioreactor Antibody Concentration (mg/L) | | Bioreactor Specific Production Rate (pg/cell/h) | | Octet Antibody Concentration in 96 DWP (mg/L) | |
|---|---|---|---|---|---|---|---|---|---|---|
| | R value | P value | R value | P value | R value | P value | R value | P value | R value | P value |
| MG-132 0.5 µM Viable Cell Concentration | 0.208 | 0.342 | 0.466* | 0.0252* | −0.00113 | 0.996 | 0.254 | 0.267 | 0.151 | 0.502 |
| MG-132 0.5 µM Viability | 0.336 | 0.117 | 0.501* | 0.0148* | 0.273 | 0.231 | 0.454* | 0.0385* | 0.361 | 0.0990 |
| Epoxomicin 0.05 µM Viable Cell Concentration | 0.463* | 0.0262* | 0.473* | 0.0228* | 0.554* | 0.00919* | 0.500* | 0.0209* | 0.358 | 0.102 |
| Epoxomicin 0.05 µM Viability | 0.106 | 0.631 | 0.245 | 0.259 | 0.378 | 0.0911 | 0.254 | 0.267 | 0.137 | 0.544 |
| Eeyarestatin I 10 µM Viable Cell Concentration | 0.0751 | 0.734 | 0.313 | 0.146 | −0.0946 | 0.683 | 0.230 | 0.317 | 0.129 | 0.566 |
| Eeyarestatin I 10 µM Viability | 0.00177 | 0.994 | 0.287 | 0.184 | −0.228 | 0.319 | 0.126 | 0.586 | 0.00743 | 0.974 |
| DMSO Viable Cell Concentration | 0.109 | 0.620 | 0.250 | 0.249 | 0.0122 | 0.958 | 0.132 | 0.569 | 0.0470 | 0.836 |
| DMSO Viability | 0.170 | 0.438 | 0.142 | 0.517 | 0.211 | 0.359 | 0.242 | 0.290 | 0.0701 | 0.757 |

Example 4: Determination of the Proteasome Activity in Production Cell Lines

As described in Example 3, the panel of cell lines investigated showed differences in their susceptibility to the proteasome inhibitors. Therefore to analyze this further, the levels of proteasome activity were determined across the cell line panel. This was performed using proteasome activity profiling probes from the van der Hoorn laboratory (Kolodziejek et al. 2011). These probes have a fluorescent tag and are designed based on inhibitor molecules, differing in their reactive group. Importantly, the probes can only bind to their target when in an active state and hence the active proteasome can be determined. The probes used in this study included MV151, which contains a vinyl sulphone reactive group and MVB003 and MVB072 that are both based on the inhibitor molecule epoxomicin and have an epoxyketone reactive group. The reactive groups of these probes bind to the N-terminal active site Thr of the catalytic subunits of the proteasome through distinct mechanisms. These probes demonstrate the activity of the three catalytic subunits of the proteasome; β1, β2 and β5 (Kolodziejek et al. 2011). In addition, probes RUB1001 that contains an epoxyketone reactive group and highlights β1 activity, and RUB1018 that has a vinyl sulphone reactive group and highlights β5 catalytic subunit activity were utilized. Analysis with the activity probes allows the proteasome activity to be determined across the panel of cell lines and investigation as to whether the activity of the various catalytic subunits of the proteasome was found to differ across these.

The activity is determined by the fluorescence intensity of the various bands observed after labelling of the samples as described in the methods chapter. Following determination of the fluorescence levels, the gels were Coomassie stained to provide a loading control. The upper band observed in FIG. 7A-7F of approximately 27 kDa represents (32 catalytic activity. The lower bands at approximately 24 kDa represent β5 and β1 catalytic activity (FIGS. 7A-7F), with RUB1018 indicating (35 activity only. The MV151 probe indicates both the β2 and β5/β1 activity. Across the cell line panel, the intensity of the lower β5/β1 band was generally of a greater intensity than the β2 band (FIGS. 7A-7F and 9A-9F), suggesting higher activity of these subunits. When using the MVB003 probe however, there appeared to be less intense β5/β1 bands and therefore activity in a number of the antibody producing cell lines compared to CHOK1SV (FIGS. 7A-7F and 9A-9F). The β2 activity of the recombinant antibody producing cell lines was generally comparable to that observed in the CHOK1SV host cell line. As might be expected, when the MVB072 probe was utilized, a similar pattern of activity was observed to that of the MVB003 probe (FIG. 7A-7F), although less variation in the β5/β1 bands were observed.

When the RUB1001 probe was used to investigate proteasome activity, which can allow the assessment of β5 and β1 activity individually, the catalytic activities of these two subunits mirrored each other across the cell line panel (FIG. 8A-8F). The levels of proteasome activity as determined using the RUB1018 probe were found to be lower in a number of the recombinant cell lines when compared to the CHOK1SV control (FIGS. 8A-8F and 9A-9F). Fluorescence analysis was also performed with the addition of no probe to the lysate samples and with epoxomicin inhibition prior to the addition of the probe to confirm the band pattern obtained was determined from binding of the probe to the catalytic subunits and not the result of non-specific binding.

This was confirmed with the absence of bands on the gels with these treated samples (FIGS. 8A-8F)

The 'total' activity determined for each probe was also investigated by combining the intensities of all the bands observed with each probe using densitometry analysis. Thus, total proteasome activity was derived from the sum of all intensities for all probes. Cell lines CHO142, CHO71, CHO77, CHO137 and CHO46 all showed elevated levels of total proteasome activity over those of the non-producing control CHOK1SV host (FIGS. 9A-9F). All cell lines were originally derived from the CHOK1SV cell line so this should provide a suitable baseline of proteasome activity without the pressures of recombinant protein production. The cell lines showing an increase in total proteasome activity were in general mid to high in productivity range of those investigated. However other cell lines, such as CHO149, CHO42 and CHO150 all showed a decrease in total proteasome activity compared to that observed in the host and have been typically categorized as high producers.

Figure 10:
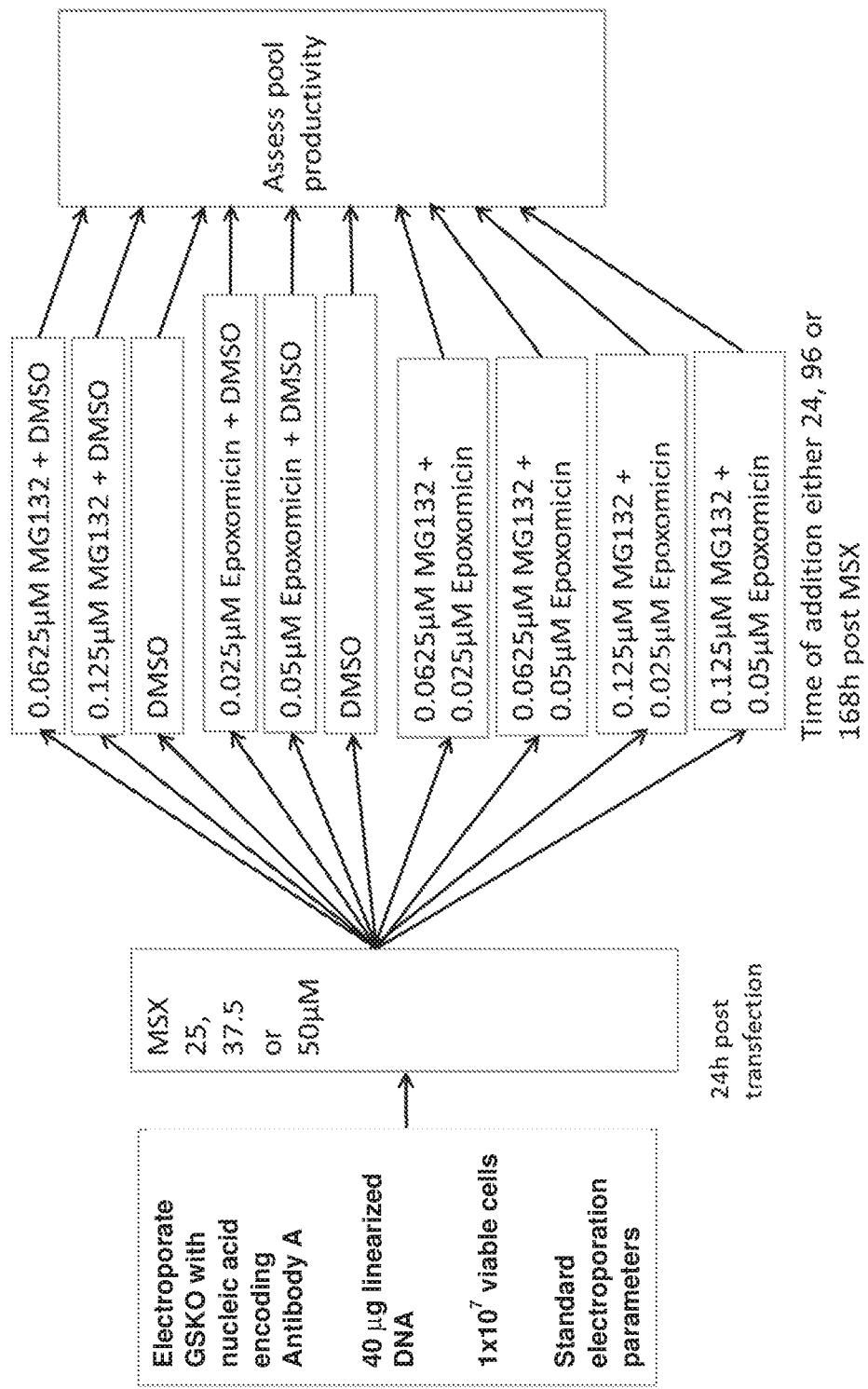
FIG. 10 is a schema depicting the protocol for cell line construction with the CHOK1 GS-KO cell line. Methionine sulfoximine (MSX) selection at a range of concentrations was performed at 24 hours after transfection of 40 µg of linearized DNA. Proteasome inhibitors were then added at either 24, 96 or 168 hours after transfection at a range of concentrations and combinations following a design of experiments plan.

Example 5: Application of Adding Proteasome Selection Pressure to the Cell Line Construction Process A correlation between cell line productivity and susceptibility of cell lines to proteasome inhibitors had been observed (see Example 3). Therefore, the hypothesis that proteasome inhibitors could be used to select for high producing recombinant cell lines during cell line construction was investigated. A cell line construction process was therefore designed to generate CHOK1 GS-KO recombinant cells lines producing the model antibody A that included the addition of the proteasome inhibitors as an additional selection pressure to methionine sulphoximine (MSX). The cell line construction process design is outlined in FIG. 10. MSX is used to select cells which successfully express the transfected plasmid through selection for glutamine synthetase (GS) expression. Although CHO cells endogenously express low amounts of GS, MSX can be used as an inhibitor to select for those cells where the GS containing construct has been incorporated stably into the genome (Fan et al. 2012). Further, the host used in this example was a CHOK1 GS-KO host cell line that lacks the expression of any endogenous GS protein. The proteasome inhibitors were added in addition to typical selection to test whether the inclusion of a selection based upon proteasome inhibition selected for cell populations which were high producers of the antibody product. The data presented in Example 3 suggested that those cells with higher productivity were less susceptible to the proteasome inhibitors and therefore should be selected for in the presence of the inhibitors. In order to test this hypothesis a range of combinations of MSX and proteasome inhibitor concentrations were used on the CHOK1 GS-KO host cell line transfected with the plasmid encoding antibody A using a design of experiments approach to determine those concentrations of inhibitors to be investigated. These are described in FIG. 10. Proteasome inhibitors were added at either 24, 96 or 168 hours post addition of MSX to allow selection based on plasmid uptake to occur prior to inhibition of the proteasome.

For the purpose of the cell line construction process, the concentrations of MG-132 used were lower than those used for the generation of the data reported in Example 2. The concentrations previously investigated in the data reported in Example 2 resulted in poor viable cell counts following the electroporation and cell line construction process. As a result the concentration was decreased for the cell line construction evaluation.

Figure 11:
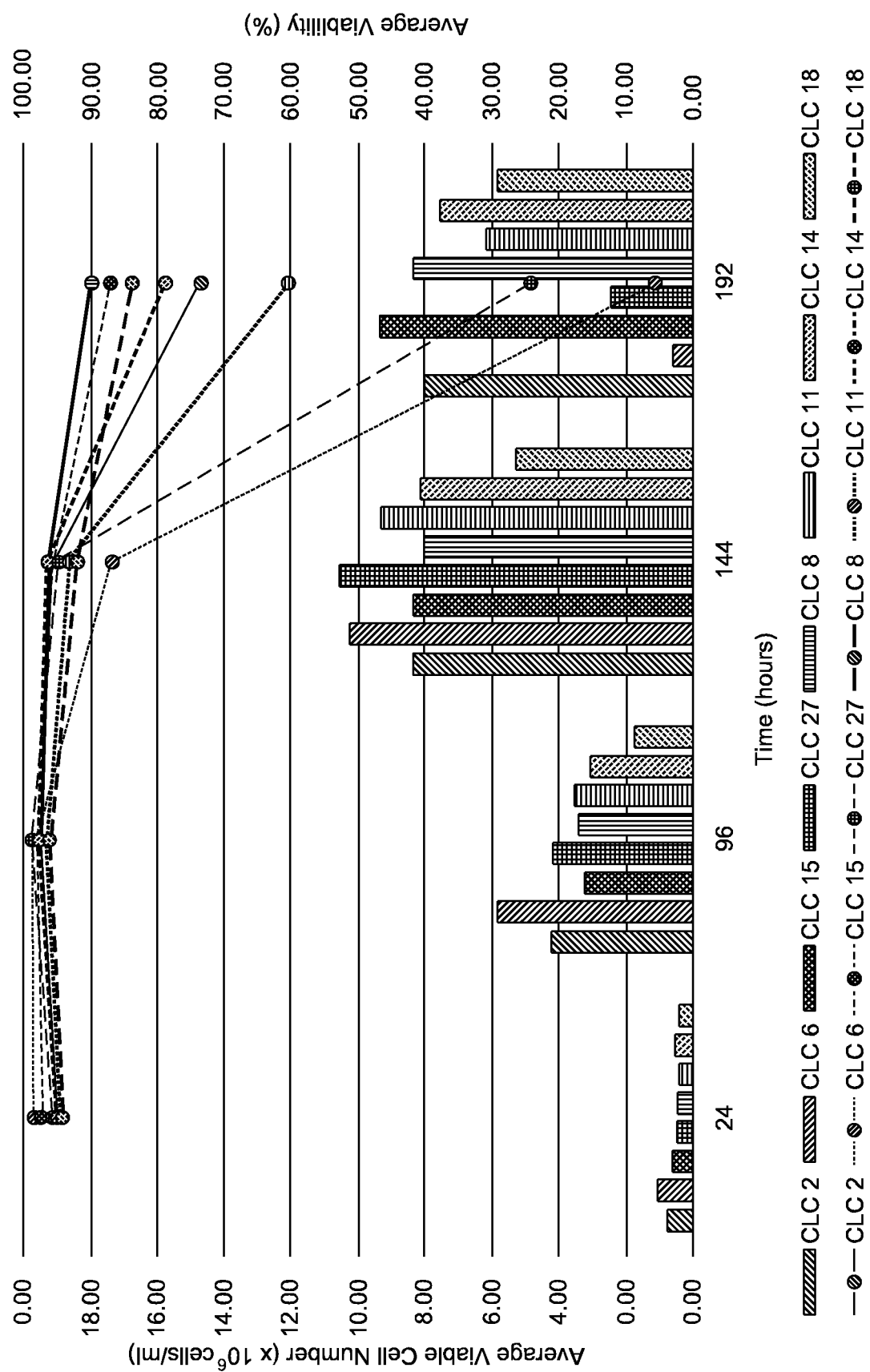
FIG. 11 is a graph showing the growth characteristics of cell populations generated using a cell line construction process with MSX and varying proteasome inhibitor selection pressures. Culture viability and viable cell concentration of the GSKO cell pools expressing the model monoclonal antibody (Antibody A) were determined every 48-72 hours following cell line construction with proteasome inhibitors in addition to MSX.

Eight out of the thirty cell line construction processes evaluated survived the cell line construction process. These were the four controls treated with different MSX concentrations alone (i.e. no proteasome inhibitor was added) and four where the process contained either MG-132 or epoxomicin alongside the inclusion of MSX. These cell populations were cultured and expanded until they were grown in a suspension batch cultures to assess the growth and antibody concentrations from these cell populations. For this purpose, cells were seeded at a concentration of $0.2 \times 10^6$ cells/ml in triplicate flasks, without the addition of the proteasome inhibitors, and incubated at 37° C. with shaking at 140 rpm in a Kuhner incubator and sampled every 48 to 72 hours for the determination of cell concentration and culture viability on a ViCell instrument. In general, the growth characteristics were similar between all the cell populations as shown in FIG. 11. CLC18, this cell line construction being undertaken in the presence of 0.025 µM epoxomicin and 37.5 µM MSX had a slower growth rate than the other cultures and did not achieve as high a viable cell number, obtaining a maximum viable cell number of $5.328 \times 10^6$ cells/ml in comparison to $8\text{-}10 \times 10^6$ cells/ml for the other cell line construction populations. CLC6 and CLC27 cell line constructions, generated in the presence of MSX alone, declined in culture viability at an earlier time point compared to the other populations, with viabilities of 5.8% and 24.2% respectively at 192 hours of culture.

Figure 12:
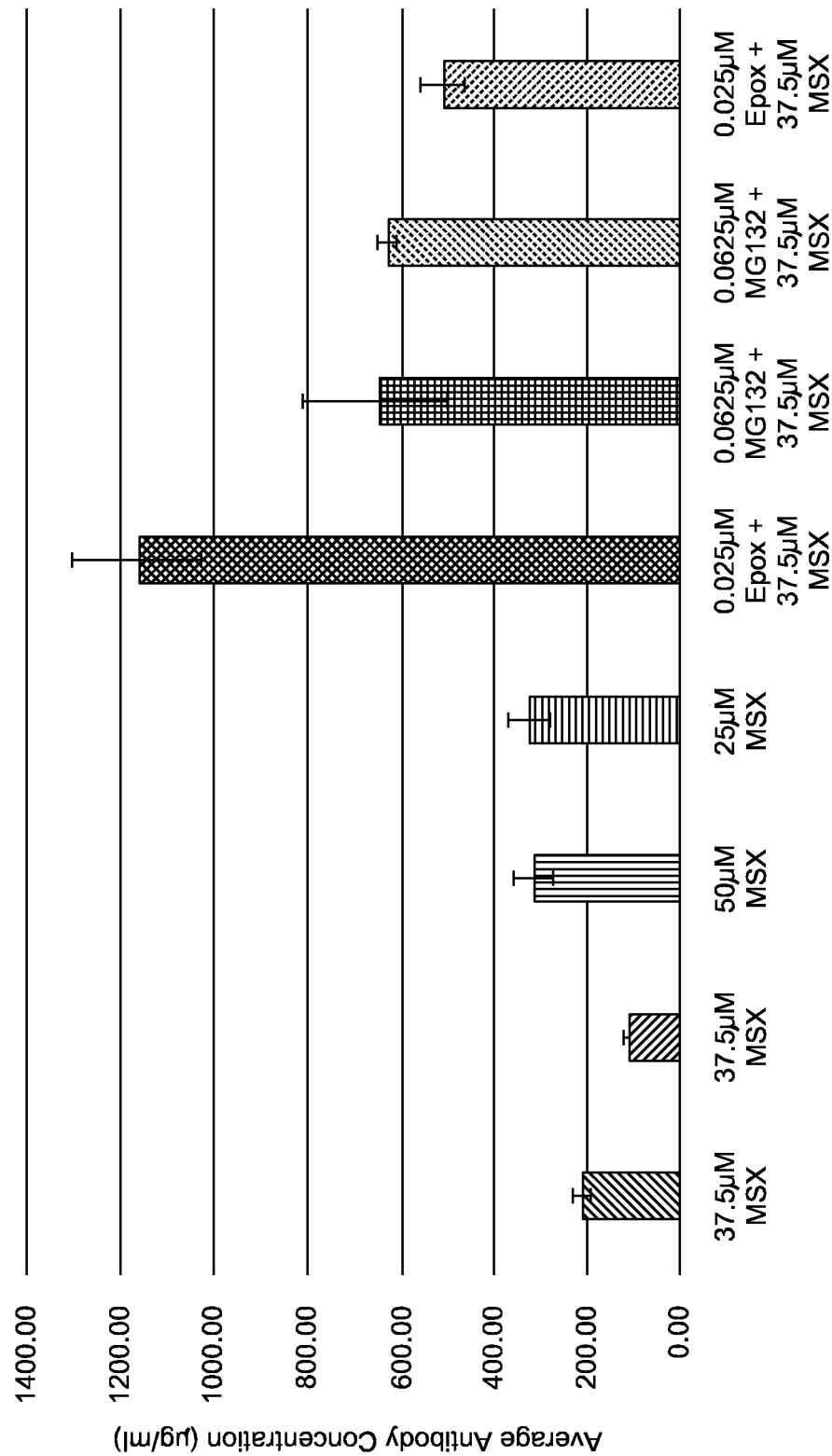
FIG. 12 is a graph showing the antibody concentrations achieved from cell populations generated using a cell line construction process with MSX and varying proteasome inhibitor selection pressures with varying selection pressures. GSKO cell lines expressing Antibody A were cultured under batch culture conditions and an ELISA assay performed with supernatant collected after 192 hours of culture following cell line construction with proteasome inhibitors in addition to MSX selection pressure.

When the antibody concentration in the supernatant of the different cell pools was analyzed there was a large difference in the concentration of product between the different cell lines when constructed using inhibitors of protein degradation or without using inhibitors of protein degradation. The antibody concentration was determined from supernatant taken at 192 hours of batch culture and determined by ELISA (FIG. 12) and Protein A HPLC. The results obtained from Protein A HPLC were similar to those observed by ELISA assay. All cultures prepared with the additional selection pressure of the proteasome inhibitors on top of the usual MSX selection showed an increase in antibody concentration over that observed from the MSX generated pools alone. Indeed, those pools generated with 0.0625 µM MG-132 and 37.5 µM MSX showed an approximate 4-fold increase in the amount of antibody present in the cell culture supernatant, whereas those generated with 0.025 µM epoxomicin and 37.5 µM MSX displayed a 3-7 fold increase in antibody concentration over the different control pools generated with MSX alone. Thus, these data indicate that the use of the proteasome inhibitors alongside MSX selection results in the generation of cell pools that produce higher yields of a model recombinant monoclonal antibody.

The susceptibility of recombinant CHO cells lines expressing a model monoclonal antibody to the proteasome inhibitors MG-132 and epoxomicin was found to differ across a panel of industrially relevant, model antibody producing GS-CHO recombinant cell lines (as described in Example 2). There was found to be a positive correlation between culture viability or viable cell number and productivity when the cells were cultured in the presence of the proteasome inhibitors at the concentrations investigated.

The data disclosed herein demonstrates that the proteasome in the high producing cell lines was less affected by the effects of inhibition suggesting that less polypeptide or protein required degradation, presumably as a result of less misfolded protein being present and hence leading to higher yields. High producing cell lines have previously been associated with elevated amounts of chaperones in recombinant protein expressing mammalian cell lines, and hence the fidelity of folding may be improved in these cells, allowing them to better facilitate high levels of recombinant protein production (Smales et al. 2004; Dinnis et al. 2006), potentially through UPR activation as a result of ER stress.

Due to the positive correlation between proteasome inhibition and antibody productivity observed in Example 3, it was hypothesized that the influence of proteasome inhibition could be used during cell line construction to select for higher recombinant protein producing populations. MSX is currently one of the major selection systems used to inhibit the endogenous glutamine synthetase (GS) of CHO cells and select for cells which are expressing exogenous GS on an introduced recombinant plasmid, resulting in a heterogeneous population of varying recombinant protein expression levels. Based on the correlation data reported in FIG. 6A-6G, whether the addition of the proteasome inhibitors as well as MSX would facilitate the emergence and selection of heterogeneous cell populations that had enhanced productivity, and potentially product quality, was investigated. Epoxomicin and MG-132 were therefore added to the cell line construction process of the GSKO cell line when transfected with the model antibody A plasmid containing the GS gene and the heavy and light chain of the model IgG4 antibody A. The majority of combinations of MSX and epoxomicin and MG-132 concentrations when applied to the selection process of transfections did not survive the selection process and subsequent culture. Cell viabilities of <6% were achieved in cultures from this experiment except the 8 cultures which progressed to the end of the experiment described herein. However, those populations that did emerge in the presence of either 0.0625 µM MG-132 or 0.025 µM epoxomicin alongside 37.5 µM MSX produced a higher amount of the cB72.3 antibody after 192 hours of batch culture when compared to those cultured with MSX alone when analyzed by either ELISA or Protein A HPLC. The additional selection pressure therefore did appear to select for the higher producing populations, in agreement with the previously reported correlation data. This data has potential benefits for use in the cell line construction process in an industrial setting to aid in the development of higher producing GS-CHO recombinant cell populations.

Example 6. Use of Proteasome and ERAD Inhibitors During Cell Line Construction

Figure 13:
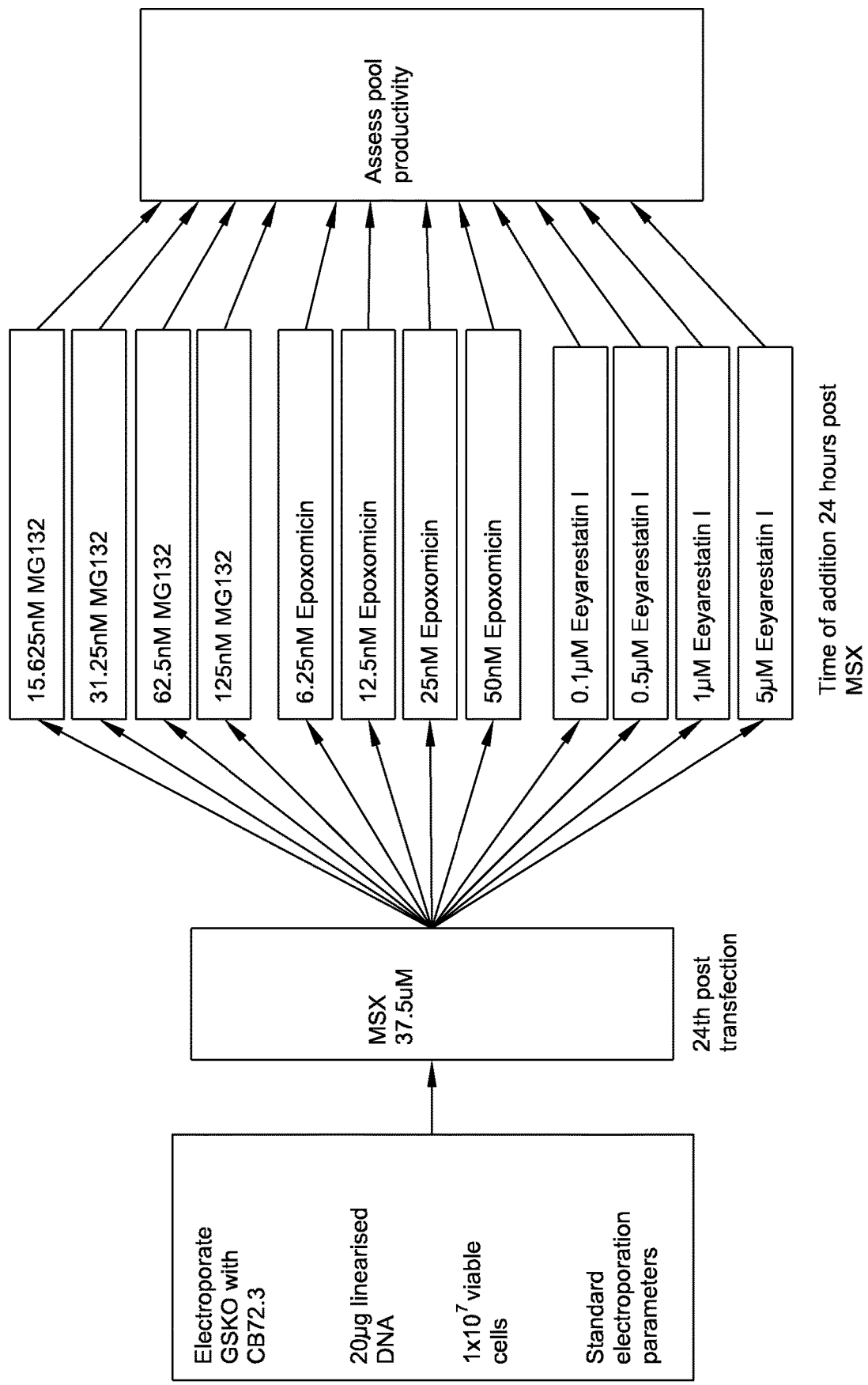
FIG. 13 depicts the experimental design to assess the use of exemplary proteasome inhibitors described herein during cell line construction.

Multiple electroporations with 20 µg of linearized GS cB72.3 monoclonal antibody containing construct with $1 \times 10^7$ viable GS KO Lonza host cells were performed and pooled. This pool was then set up into 10 ml cultures, each containing approximately $0.25 \times 10^6$ cells and 10 µg DNA, and immediately placed in a static incubator at 37° C. with 5% $CO_2$. Cell media consisted of commercially available CD-CHO media without glutamine and the addition of MSX and inhibitors as outlined below. 24 hours post transfection, MSX was added to the media to make the culture volume up to 15 ml and provide a final MSX concentration of 37.5 µM. The different inhibitors were then added to the pools a further 24 hours after the addition of MSX. A range of concentrations were added for each inhibitor to give the final concentrations in the flasks as described in FIG. 13. Only one inhibitor treatment was performed per flask (no combined treatments) and all were performed in combination with 37.5 µM MSX as outlined in FIG. 13.

The cell pools were then left in the static incubator at 37° C. and 5% CO2 until the viable cell concentration in the flask reached ~$0.2 \times 10^6$ cells/ml. When this viable cell number was achieved, cell pools were moved into 125 mL Erlenmeyer shake flasks and cultured in a 20 mL volume of CD-CHO including MSX and the appropriate concentration of inhibitor at 37° C. under a 5% CO2 in air environment with shaking at 140 rpm. 24 out of 33 transfections/pools were eventually moved across to shake flasks as they exceeded the required viable cell concentration described above. The final inhibitor concentrations, that alongside 37.5 µM MSX, resulted in the emergence of cell pools were as follows: MG-132: 15.625 and 31.25 nM; Epoxomicin: 6.25, 12.5 and 25 nM; Eeyarestatin I: 0.1, 0.5 and 1 µM concentrations.

Cell pools were then cultured in the presence of the appropriate inhibitor (and inhibitor concentration and 37.5 µM MSX) in 20 mL of CD-CHO for several passages (each being seeded at $0.2 \times 10^6$ viable cells/ml) before batch cultures were set up for each to assess the growth of the pool and to sample for product concentration over the duration of culture. For this purpose 20 ml batch cultures (seeded at $0.2 \times 10^6$ viable cells/ml) were sampled at 48, 96 and 168 hours for growth and titre information. The cell pools were also then passaged for an additional two passages in the absence of the inhibitors (but containing MSX) to determine if any changes in growth or productivity were observed, i.e. were the improved culture titres only maintained if the inhibitor was continually present. The resulting findings and data are presented in FIGS. 13-18.

Figure 14:
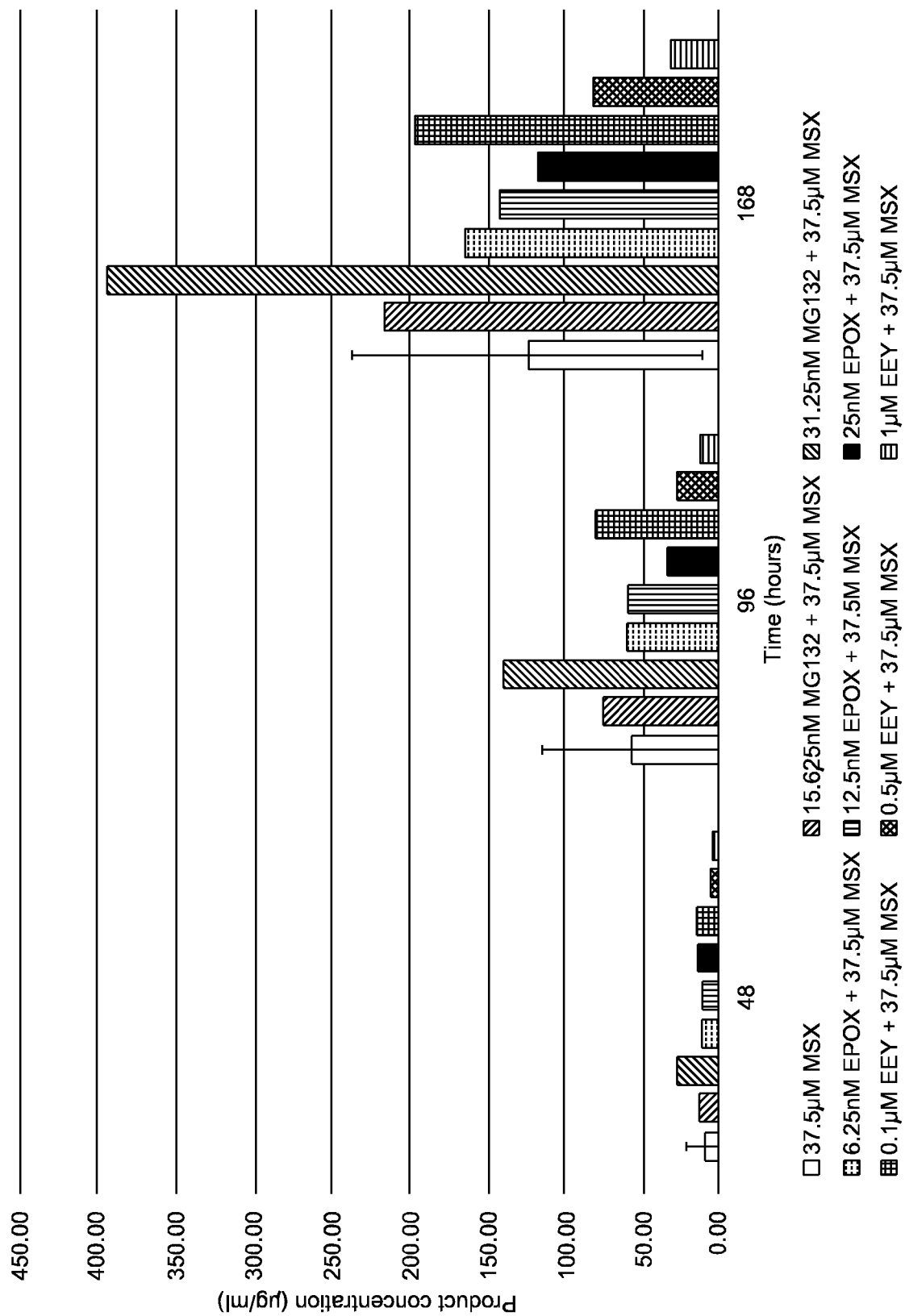
FIG. 14 is a bar graph depicting the average monoclonal antibody product concentrations achieved following the recombinant GS-CHO cell line construction process with the various inhibitors in batch cultures setup from cells continually cultured in the presence of the inhibitors. Assessment of cB72.3 monoclonal antibody concentration from supernatant samples taken at 48, 96 and 168 hours of 20 mL batch culture following seeding at $0.2 \times 10^6$ viable cells/ml of cell pools generated from cell line construction with proteasome inhibitors in addition to MSX selection pressure. Product titre was assessed using Protein A sensors on an Octet system (n=3 for 37.5 µM MSX control, n=2 for inhibitor treatments except 25 nM Epoxomicin n=1).

First, the average monoclonal antibody product concentrations achieved following the recombinant GS-CHO cell line construction process with the various inhibitors in batch cultures setup from cells continually cultured in the presence of the inhibitors was assessed (FIG. 14). The assessment of cB72.3 monoclonal antibody concentration from supernatant samples taken at 48, 96 and 168 hours of 20 ml batch culture following seeding at $0.2 \times 10^6$ viable cells/ml of cell pools generated from cell line construction with proteasome inhibitors in addition to MSX selection pressure. Product titre was assessed using Protein A sensors on an Octet system (n=3 for 37.504 MSX control, n=2 for inhibitor treatments except 25 nM Epoxomicin n=1). As shown in FIG. 14, cell pools constructed in the presence of 31.25 nM MG-132 and 37.5 µM MSX exhibited enhanced monoclonal antibody titre, being almost 4-fold higher than those observed from the control pool after 168 h of batch culture.

Figure 15:
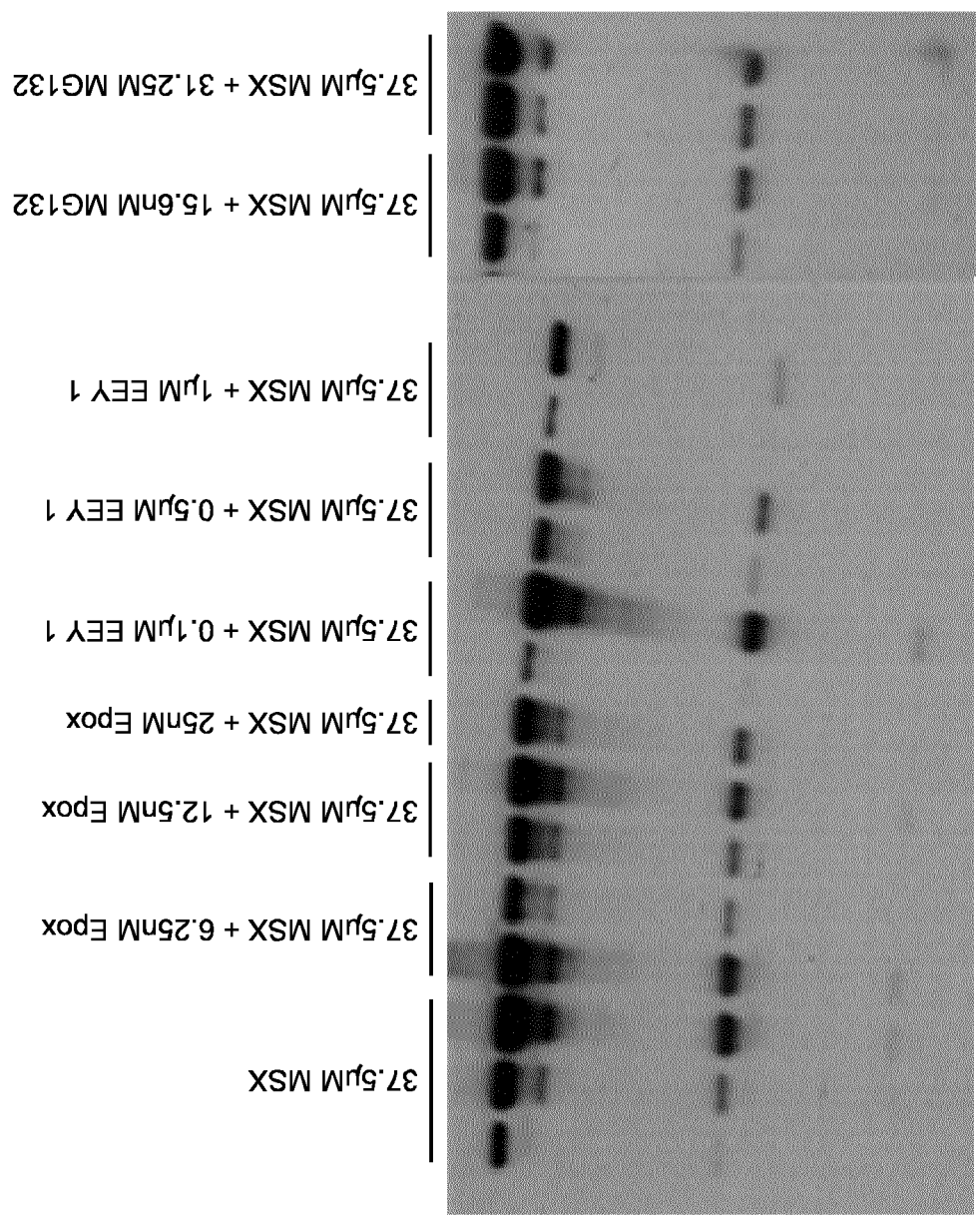
FIG. 15 depicts a western blot analysis for monoclonal antibody product achieved following the recombinant GS-CHO cell line construction process with the various inhibitors in batch cultures setup from cells continually cultured in the presence of the inhibitors. Assessment of cB72.3 concentration from supernatant samples taken at 168 hours of culture following seeding at $0.2 \times 10^6$ viable cells/ml of cell pools generated from cell line construction with proteasome inhibitors in addition to MSX selection pressure. Western blots were probed using anti-heavy chain antibody (Sigma).

Second, analysis for monoclonal antibody product achieved following the recombinant GS-CHO cell line construction process with the various inhibitors in batch cultures setup from cells continually cultured in the presence of the inhibitors was performed via western blot (FIG. 15). The cB72.3 concentration from supernatant samples taken at 168 hours of culture following seeding at $0.2 \times 10^6$ viable cells/ml of cell pools generated from cell line construction with proteasome inhibitors in addition to MSX selection pressure as determined. Western blots were probed using anti-heavy chain antibody (Sigma). As shown in FIG. 15, cell pools generated in the presence of the different inhibitors generally showed more intense antibody bands, and hence higher antibody productivity, than those from the control, MSX alone, generated cell pools.

Figure 16:
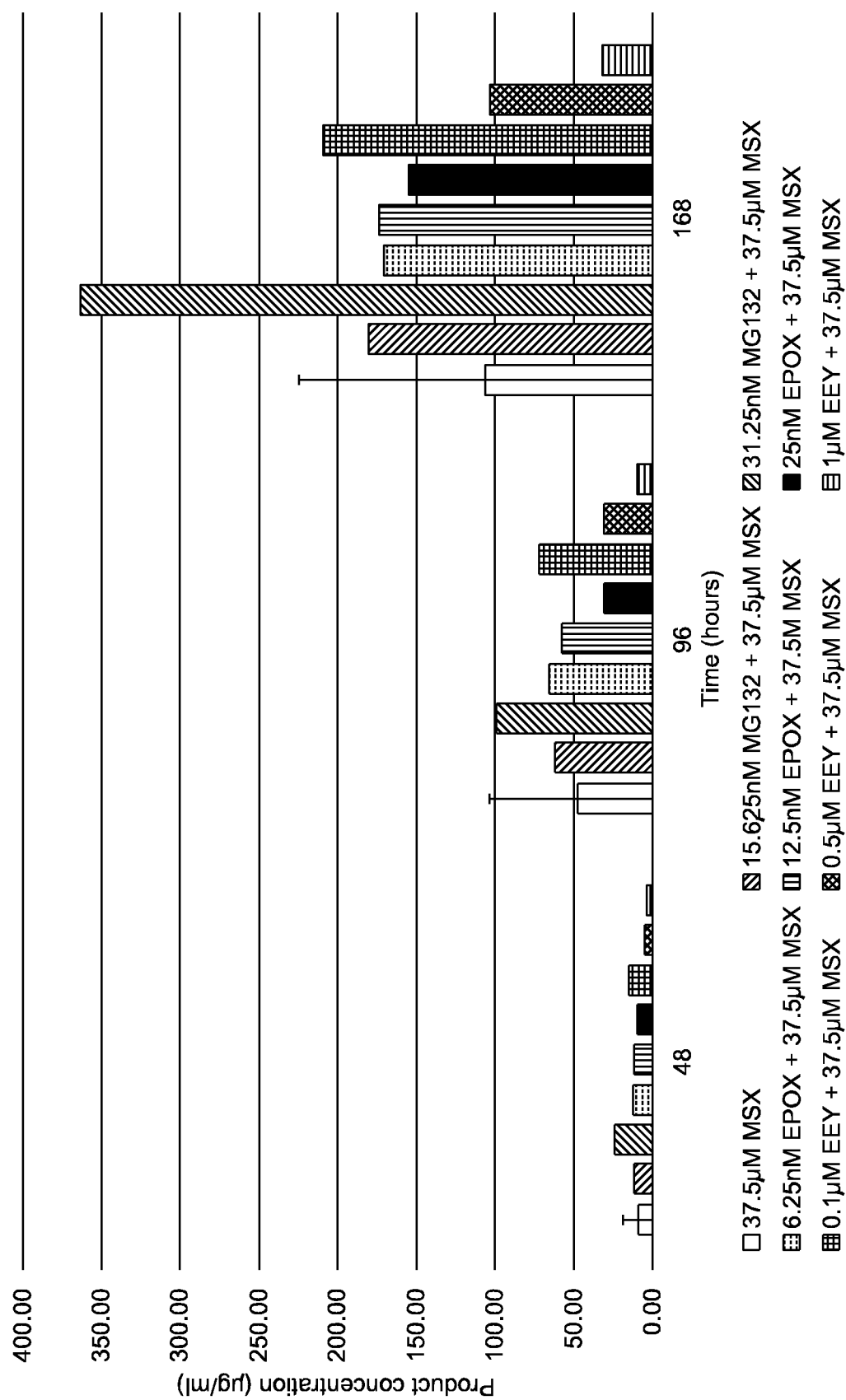
FIG. 16 is a bar graph depicting the average monoclonal antibody product concentrations achieved following the recombinant GS-CHO cell line construction process with the various inhibitors in batch cultures setup from cells cultured for two passages in the absence of the inhibitors. Assessment of cB72.3 monoclonal antibody concentration from supernatant samples taken at 48, 96 and 168 hours of 20 mL batch culture following seeding at $0.2 \times 10^6$ viable cells/ml of cell pools generated from cell line construction with proteasome inhibitors in addition to MSX selection pressure. Product titre was assessed using Protein A sensors on an Octet system (n=3 for 37.504 MSX control, n=2 for inhibitor treatments except 25 nM Epoxomicin n=1).

Third, the average monoclonal antibody product concentrations achieved following the recombinant GS-CHO cell line construction process with the various inhibitors in batch cultures setup from cells cultured for two passages in the absence of the inhibitors was assessed (FIG. 16). Assessment of cB72.3 monoclonal antibody concentration from supernatant samples taken at 48, 96 and 168 hours of 20 mL batch culture following seeding at $0.2\times10^6$ viable cells/ml of cell pools generated from cell line construction with proteasome inhibitors in addition to MSX selection pressure. Product titre was assessed using Protein A sensors on an Octet system (n=3 for 37.504 MSX control, n=2 for inhibitor treatments except 25 nM Epoxomicin n=1). As shown in FIG. 16, cell pools constructed in the presence of 31.25 nM MG-132 and 37.5 µM MSX exhibited enhanced monoclonal antibody titre, being almost 4-fold higher than those observed from the control pool after 168 h of batch culture.

Figure 17:
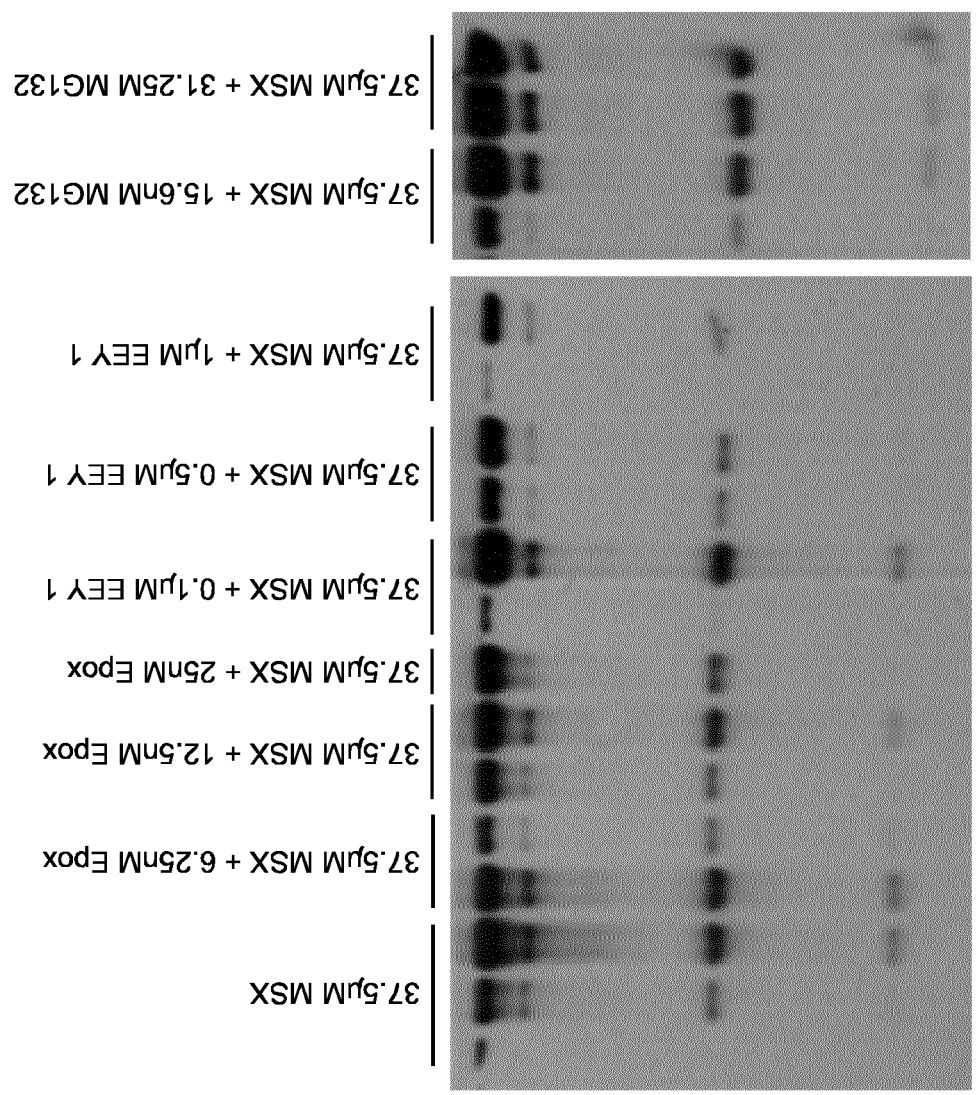
FIG. 17 depicts a western blot analysis for monoclonal antibody product following the recombinant GS-CHO cell line construction process with the various inhibitors in batch cultures setup from cells cultured for two passages in the absence of the inhibitors. Assessment of cB72.3 concentration from supernatant samples taken at 168 hours of culture following seeding at $0.2 \times 10^6$ viable cells/ml of cell pools generated from cell line construction with proteasome inhibitors in addition to MSX selection pressure. Cell pools were passaged twice in the absence of the inhibitors before the sampling batch cultures were run. Western blots were probed using anti-heavy chain antibody (Sigma).

Fourth, analysis for monoclonal antibody product following the recombinant GS-CHO cell line construction process with the various inhibitors in batch cultures setup from cells cultured for two passages in the absence of the inhibitors was determined via western blot (FIG. 17). Assessment of cB72.3 concentration from supernatant samples taken at 168 hours of culture following seeding at $0.2\times10^6$ viable cells/ml of cell pools generated from cell line construction with proteasome inhibitors in addition to MSX selection pressure. Cell pools were passaged twice in the absence of the inhibitors before the sampling batch cultures were run. Western blots were probed using anti-heavy chain antibody (Sigma). As shown in FIG. 17, cell pools generated in the presence of the different inhibitors generally showed more intense antibody bands, and hence higher antibody productivity, than those from the control, MSX alone, generated cell pools.

Figure 18:
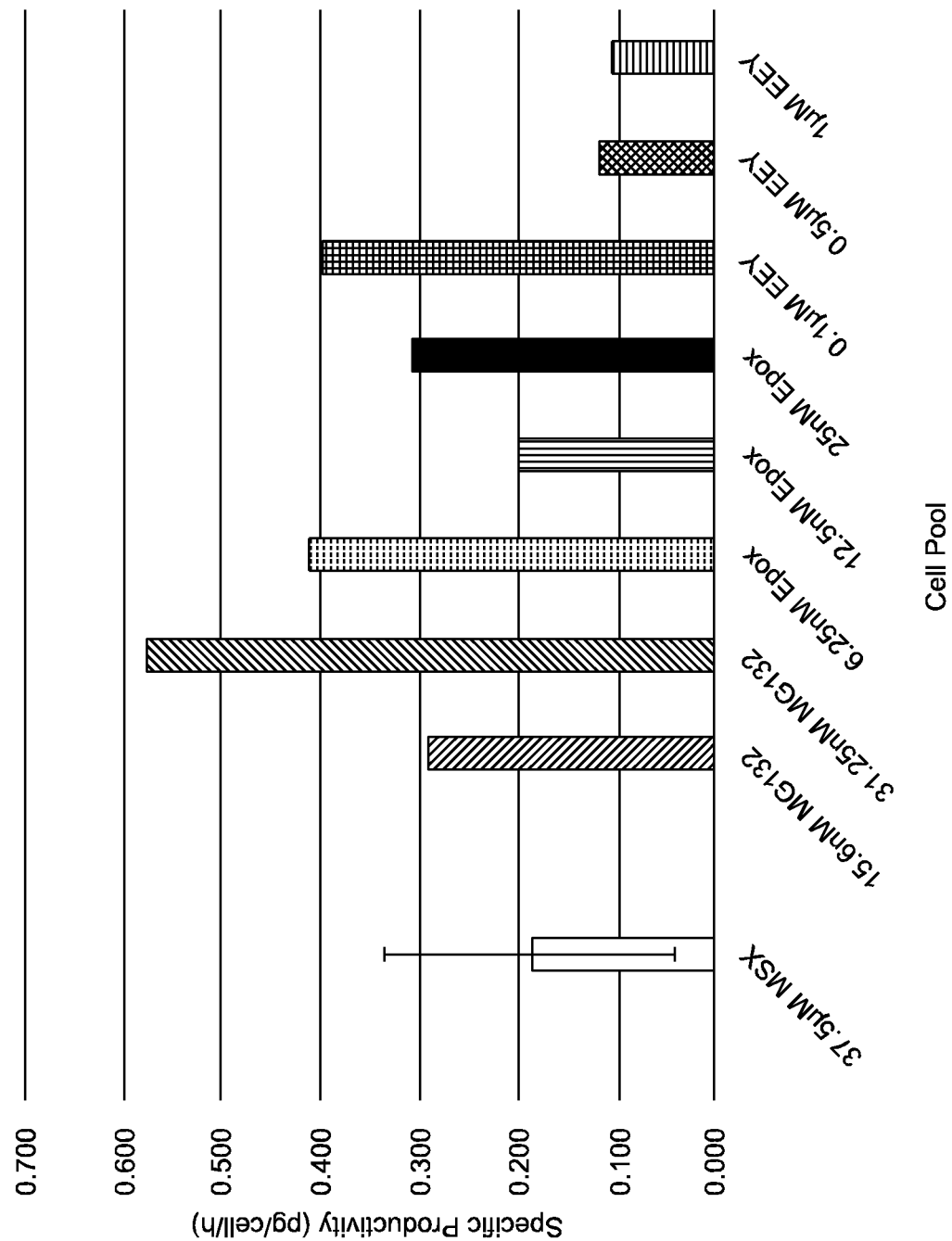
FIG. 18 is a bar graph depicting the average specific productivities calculated following the cell line construction process immediately after treatment with inhibitors. Specific productivities were calculated from data collected on viable cell number (determined on the Vicell) and product concentration (derived using Protein A probes on the octet system) from supernatant samples taken at 48, 96 and 168 hours of culture following seeding at $0.2 \times 10^6$ cells/ml of cell pools generated from cell line construction with proteasome inhibitors in addition to MSX selection pressure. Individual specific activities were calculated for each cell pool and then the average for each treatment determined (n=3 for 37.5 µM MSX control, n=2 for inhibitor treatments except 25 nM Epoxomicin n=1).

Fifth, the average specific productivities calculated following the cell line construction process immediately after treatment with inhibitors was assessed (FIG. 18). Specific productivities were calculated from data collected on viable cell number (determined on the Vicell) and product concentration (derived using Protein A probes on the octet system) from supernatant samples taken at 48, 96 and 168 hours of culture following seeding at $0.2\times10^6$ cells/ml of cell pools generated from cell line construction with proteasome inhibitors in addition to MSX selection pressure. Individual specific activities were calculated for each cell pool and then the average for each treatment determined (n=3 for 37.5 µM MSX control, n=2 for inhibitor treatments except 25 nM Epoxomicin n=1). As shown in FIG. 18, cell specific productivities were enhanced compared to MSX control pools when cell pools were generated in presence of MG-132, particularly 31.25 nM concentrations, and at various concentrations of epoxomicin and eeyarestatin.

Figure 19:
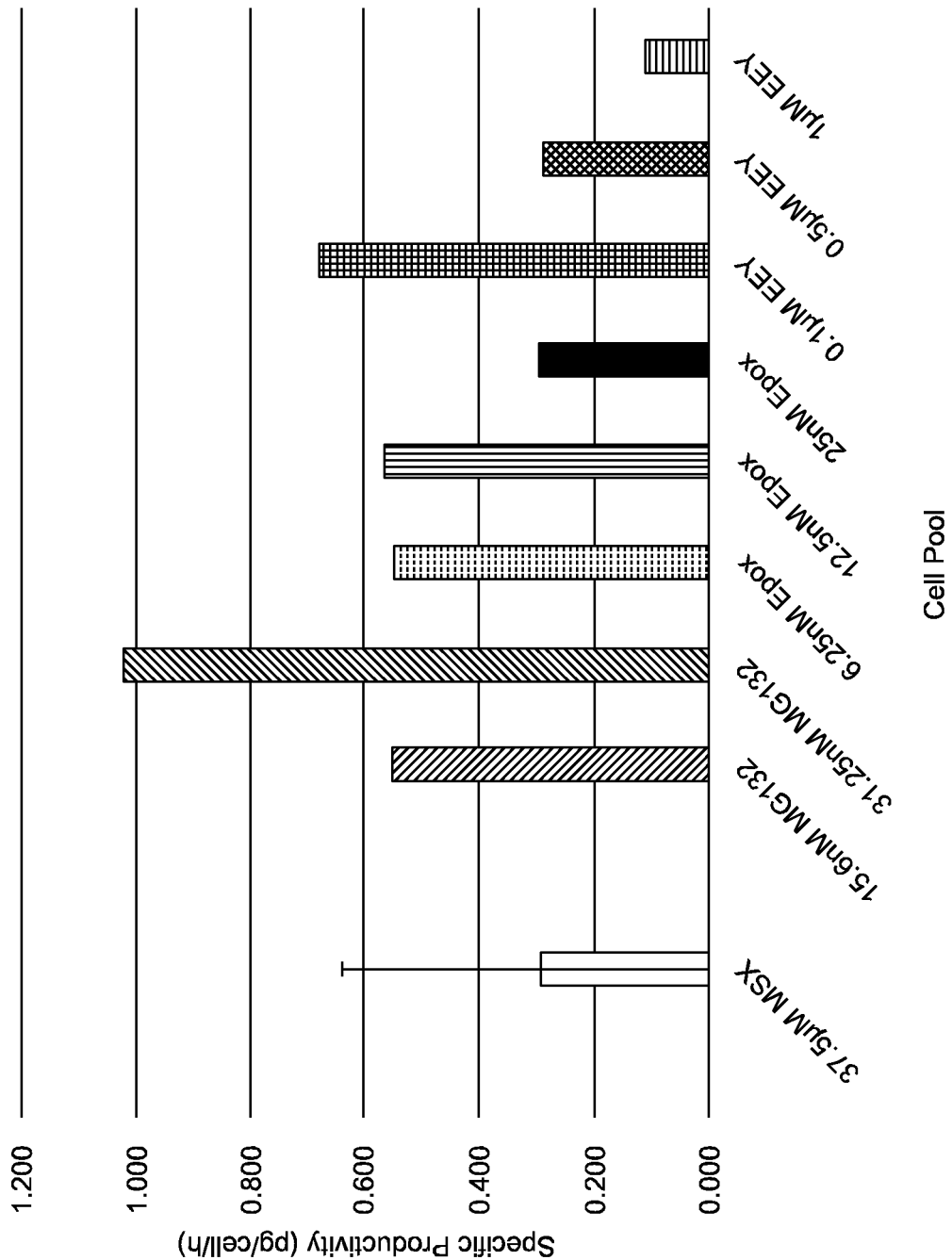
FIG. 19 is a bar graph depicting the average cell specific monoclonal antibody productivities calculated achieved following the recombinant GS-CHO cell line construction process with the various inhibitors in batch cultures setup from cells cultured in the absence of the inhibitors for two passages. Specific productivities were calculated from the determined cell numbers (determined on a Vicell instrument) and product concentration (derived using Protein A probes on the octet system) from supernatant samples taken at 48, 96 and 168 hours of batch culture following seeding at $0.2 \times 10^6$ cells/ml of cell pools generated from cell line construction with proteasome inhibitors in addition to MSX selection pressure. Individual specific activities were calculated for each cell pool and then the average for each treatment determined (n=3 for 37.5 µM MSX control, n=2 for inhibitor treatments except 25 nM Epoxomicin n=1).

Sixth, the average cell specific monoclonal antibody productivities calculated achieved following the recombinant GS-CHO cell line construction process with the various inhibitors in batch cultures setup from cells cultured in the absence of the inhibitors for two passages was assessed (FIG. 19). Specific productivities were calculated from the determined cell numbers (determined on a Vicell instrument) and product concentration (derived using Protein A probes on the octet system) from supernatant samples taken at 48, 96 and 168 hours of batch culture following seeding at $0.2\times10^6$ cells/ml of cell pools generated from cell line construction with proteasome inhibitors in addition to MSX selection pressure. Individual specific activities were calculated for each cell pool and then the average for each treatment determined (n=3 for 37.5 µM MSX control, n=2 for inhibitor treatments except 25 nM Epoxomicin n=1). As shown in FIG. 19, cell specific productivities were enhanced compared to MSX control pools when cell pools were generated in presence of MG-132, particularly 31.25 nM concentrations, and at various concentrations of epoxomicin and eeyarestatin.

Conclusions

Overall, the data described in FIGS. 14-19 demonstrate that cell pools with the added selection pressure of proteasome and ERAD inhibitors can generate cell pools with enhanced productivity over the equivalent control with MSX selection alone. This provides further evidence that addition of the proteasome or ERAD inhibitors to the cell line construction process provides an additional selection pressure, resulting in the emergence of culture populations with improved specific productivities and over recombinant product titre.

Figure 23:
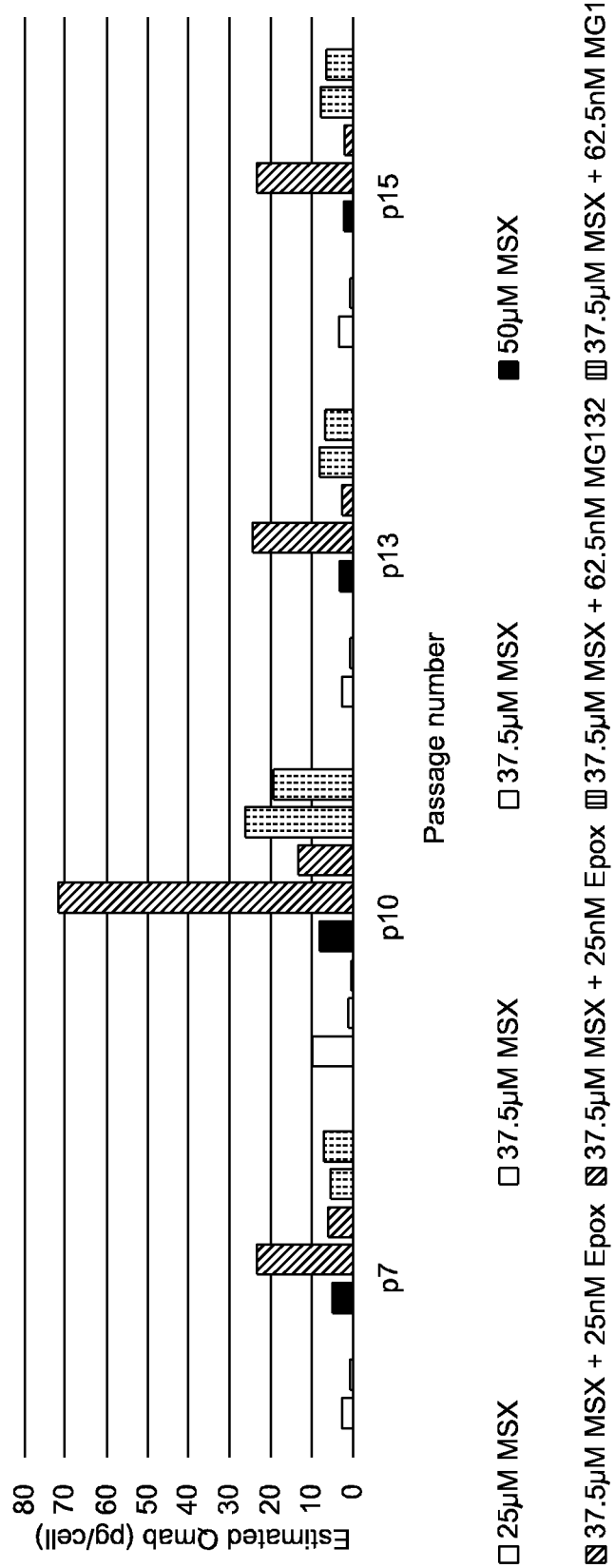
FIG. 23 is a bar graph depicting the estimated cell specific productivities determined from supernatant samples taken during routine culture of recombinant cell pools generated using the protein degradation inhibitors at different passage numbers. Assessment of cB72.3 concentration from supernatant samples taken during routine subculture every 3-4 days following revival of successful pools from the cell line construction process with the addition of proteasome inhibitors. Product titre was assessed using Protein A sensors on the Octet system and then the level of product per cell was determined using cell counts determined on the ViCell.

Example 7. Stability of Recombinant CHO Cell Pools Generated with Inhibitors Used During the Cell Line Construction Process Cell pools from a previous cell line construction generated in the presence of proteasome inhibitors as an additional selection pressure and MSX using the GS selection system were revived following cryopreservation. These pools were then passaged 15 times every 3-4 days to determine if the beneficial effect of the additional selection pressure was maintained over time. Routine subculture was performed every 3-4 days and samples were taken from later passages to determine if the effects on product yield were maintained over time. In each passage a batch culture of the recombinant cell pools expressing a model monoclonal antibody were setup (using $0.2\times10^6$ viable cells per mL) in 20 ml CD-CHO and MSX as outlined below in 125 ml Erlenmeyer shake flasks at 37° C. under a 5% $CO_2$ in air environment with shaking at 140 rpm. As shown in FIG. 23, the relative cell specific productivities between the different cell pools were retained over the different passage numbers.

Example 8. Selection/Adaptation of the GS-KO CHO Cell Host by Culturing in the Presence of Proteasome or ERAD Inhibitors to Generate New Hosts with Enhanced Productivity Characteristics In order to ascertain if adapted/selected host cells with the ability to produce enhanced recombinant protein yields and quality could be generated by culturing the Lonza GS-KO CHO host cell line in the presence of the protein degradation inhibitors, the GS-KO host cell line was cultured in the presence of various protein degradation inhibitors for a series of passages. The host cell line was therefore cultured in 20 ml CD-CHO+6 mM glutamine+the appropriate inhibitors as outlined below in 125 ml Erlenmeyer shake flasks at 37° C. under a 5% $CO_2$ in air environment with shaking at 140 rpm. At each passage the new culture was seeded at $0.2\times10^6$ viable cells/ml. Cells were passaged when the cell number exceeded $1\times10^6$ viable cells per mL.

The following concentrations and passages were undertaken: host cells with DMSO, or with MG132 at a final concentration of 15.6 nM, Eeyarestatin I at a final concentration of 1 and 0.1 µM, and Epoxomicin at a final concentration of 6.25 nM, and were subjected to 9 passages following addition of the drug to the host. Host cells in a final MG132 concentration of 62.5 nM were subjected to 5 passages following addition of the drug and those in Epoxomicin at a final concentration of 25 nM were subjected to 8 passages following addition of the drug. All of the above then had a further 2 passages in the absence of the drug for the transient expression experiment whereby selection/adaptation pressure had been removed. In the case of host cells cultured in the presence of MG132 at a final concentration of 125 nM, there were not sufficient cells for the first experiment whereby transfection of the vector containing the model monoclonal antibody was undertaken immediately after culturing in the presence of the drug. However, cells in the presence of this concentration of MG132 were subjected to 4 passages at this concentration and then a further 2 in the absence of the drug. At this time there was sufficient cells for the transfection following passage of the cells without the drug (2nd experiment of the two) to be undertaken.

Transient transfection of the emerging cell host pools described above was then performed via electroporation with 20 μg of the model cB72.3 plasmid and $1 \times 10^7$ viable cells and the cells placed in 20 ml of fresh CD-CHO media plus 6 mM glutamine in 125 ml Erlenmeyer shake flasks and cultured at 37° C. under a 5% $CO_2$ in air environment with shaking at 140 rpm. This was undertaken for the host cell pools that had been in the presence of the inhibitors continually and those that had been passaged for an additional two passages in the absence of the inhibitors. Samples were taken from these batch cultures to monitor growth and antibody titre at 48, 96 and 168 hours post-transfection. The resulting findings and data are presented in FIGS. 20-23.

Figure 20:
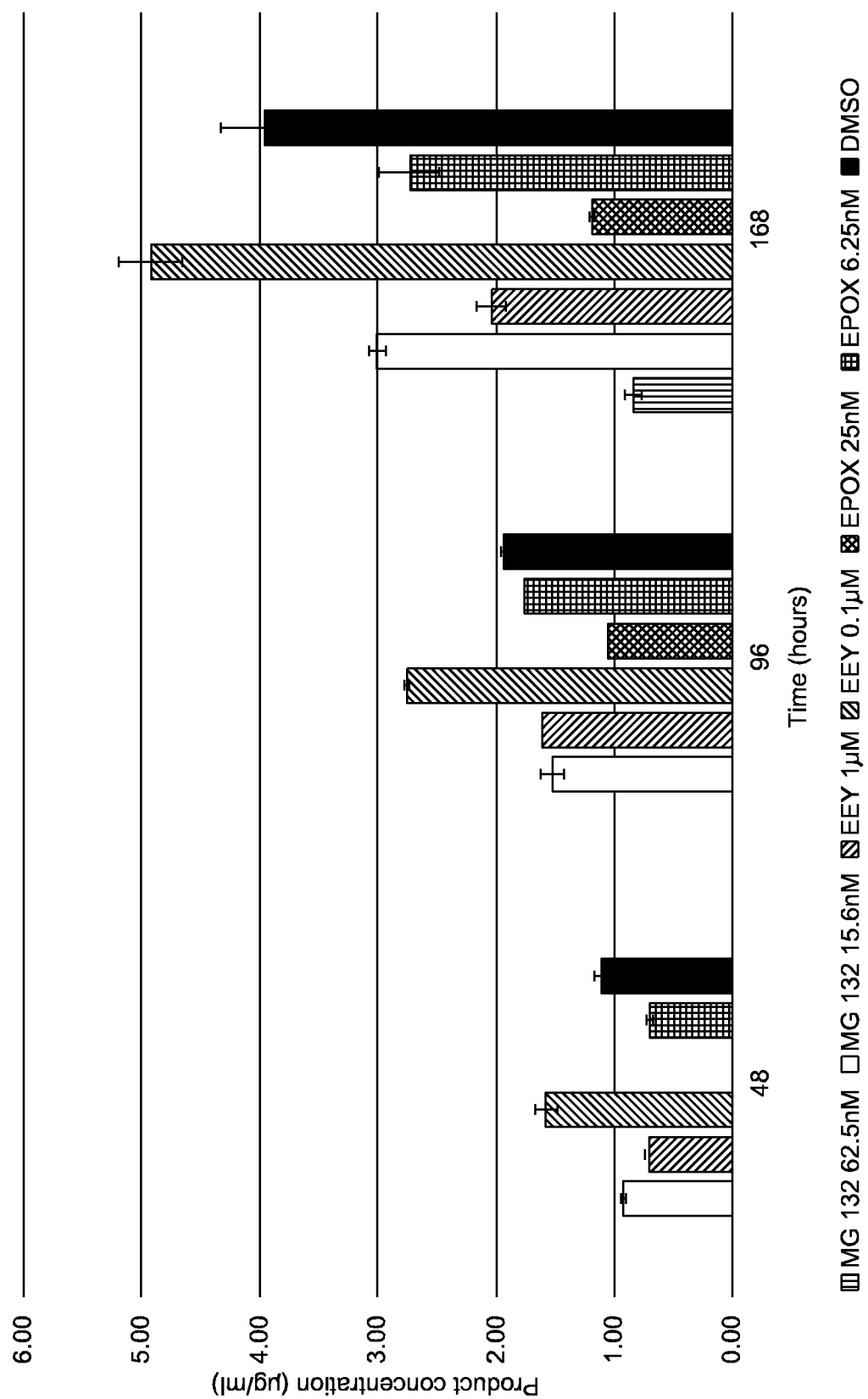
FIG. 20 is a bar graph depicting the antibody product concentrations achieved post transient transfection in batch culture of the host cell pools following culture in the presence of either proteasome or ERAD inhibitors. Assessment of cB72.3 concentration from supernatant samples taken at 48, 96 and 168 hours post transfection following electroporation of $1 \times 10^7$ cells with 20 µg of DNA and resuspension into 20 ml cultures. Prior to electroporation, the host cell line was cultured in the presence of the indicated proteasome and ERAD inhibitors at the concentrations indicated. Product titre was assessed using Protein A sensors on the Octet system.

First, the antibody product concentrations achieved post transient transfection in batch culture of the host cell pools following culture in the presence of either proteasome or ERAD inhibitors was assessed (FIG. 20). Assessment of cB72.3 concentration from supernatant samples taken at 48, 96 and 168 hours post transfection following electroporation of $1 \times 10^7$ viable cells with 20 μg of DNA and resuspension into 20 ml cultures. Prior to electroporation, the host cell line was cultured in the presence of the indicated proteasome and ERAD inhibitors at the concentrations indicated. Product titre was assessed using Protein A sensors on the Octet system. As shown in FIG. 20, cells cultured in the presence of Eeyarestatin I at a final concentration of 0.1 μM gave higher transient titres than the DMSO control cells, providing evidence that the culturing of the host cell in the presence of proteasome inhibitors can be used to adapt/select for cells with the capability of higher recombinant protein production.

Figure 21:
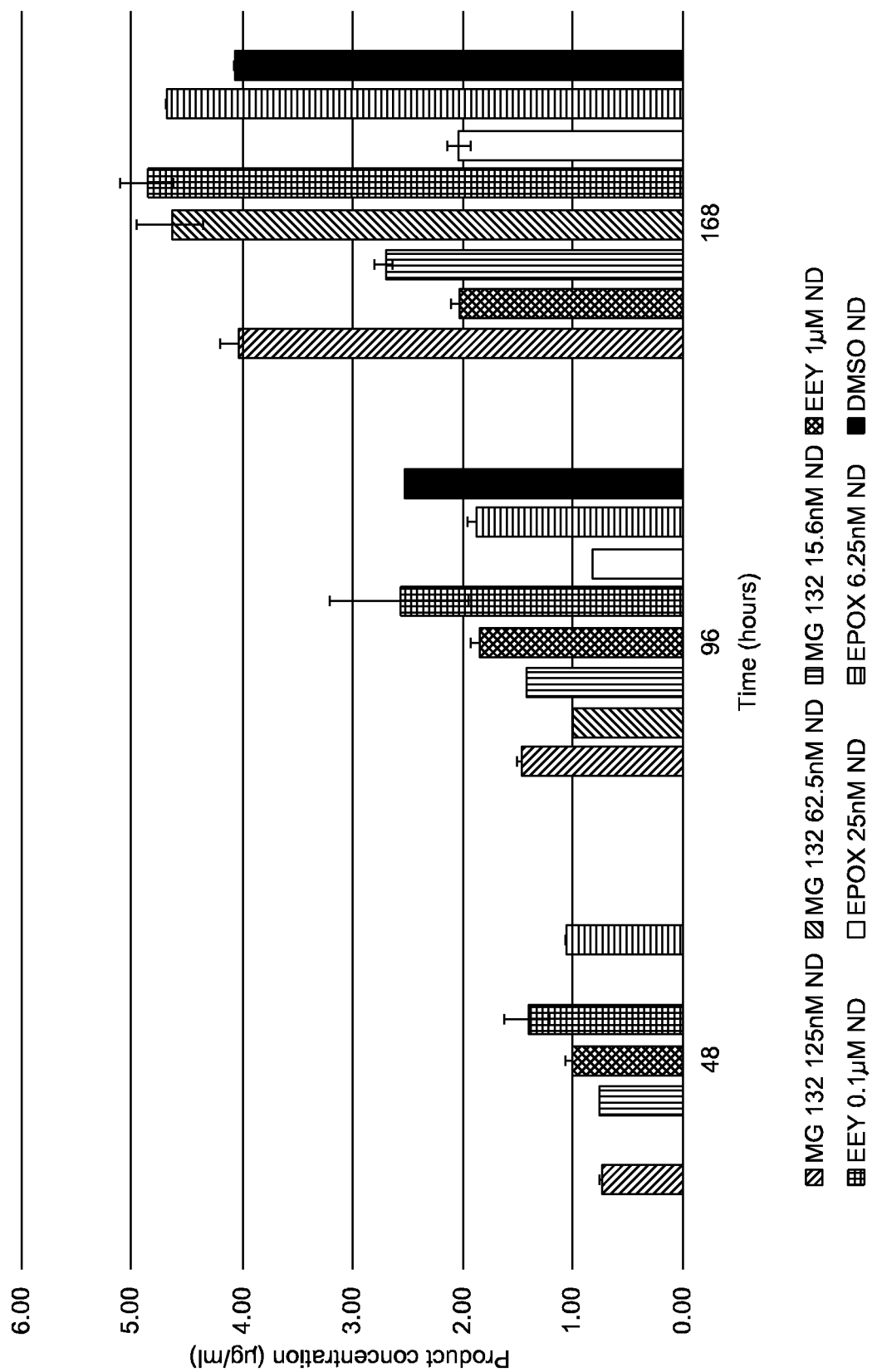
FIG. 21 is a bar graph depicting the antibody product concentrations achieved post transient transfection of CHO host cell pool following initial culture in the presence of either proteasome or ERAD inhibitors and then subsequent subculture for 2 passages in the absence of the inhibitors before the transient batch culture. Assessment of cB72.3 concentration from supernatant samples taken at 48, 96 and 168 hours post transfection following electroporation of $1 \times 10^7$ cells with 20 µg DNA and resuspension into 20 ml batch cultures. Prior to electroporation the host cell line was initially cultured in the presence of proteasome and ERAD inhibitors, and then passaged twice without the presence of inhibitors. Product titre was assessed using Protein A sensors on the Octet system.

Second the antibody product concentrations achieved post transient transfection of CHO host cell pool following initial culture in the presence of either proteasome or ERAD inhibitors and then subsequent subculture for 2 passages in the absence of the inhibitors before the transient batch culture was assessed (FIG. 21). Assessment of cB72.3 concentration from supernatant samples taken at 48, 96 and 168 hours post transfection following electroporation of $1 \times 10^7$ viable cells with 20 μg DNA and resuspension into 20 ml batch cultures. Prior to electroporation the host cell line was initially cultured in the presence of proteasome and ERAD inhibitors, then passaged twice without the presence of inhibitors. Product titre was assessed using Protein A sensors on the Octet system. As shown in FIG. 21, cells initially cultured in the presence of Eeyarestatin I or 6.25 nM Epoxomicin gave higher transient titres than the DMSO control cells, providing evidence that the culturing of the host cell in the presence of proteasome inhibitors can be used to adapt/select for cells with the capability of higher recombinant protein production.

Figure 22:
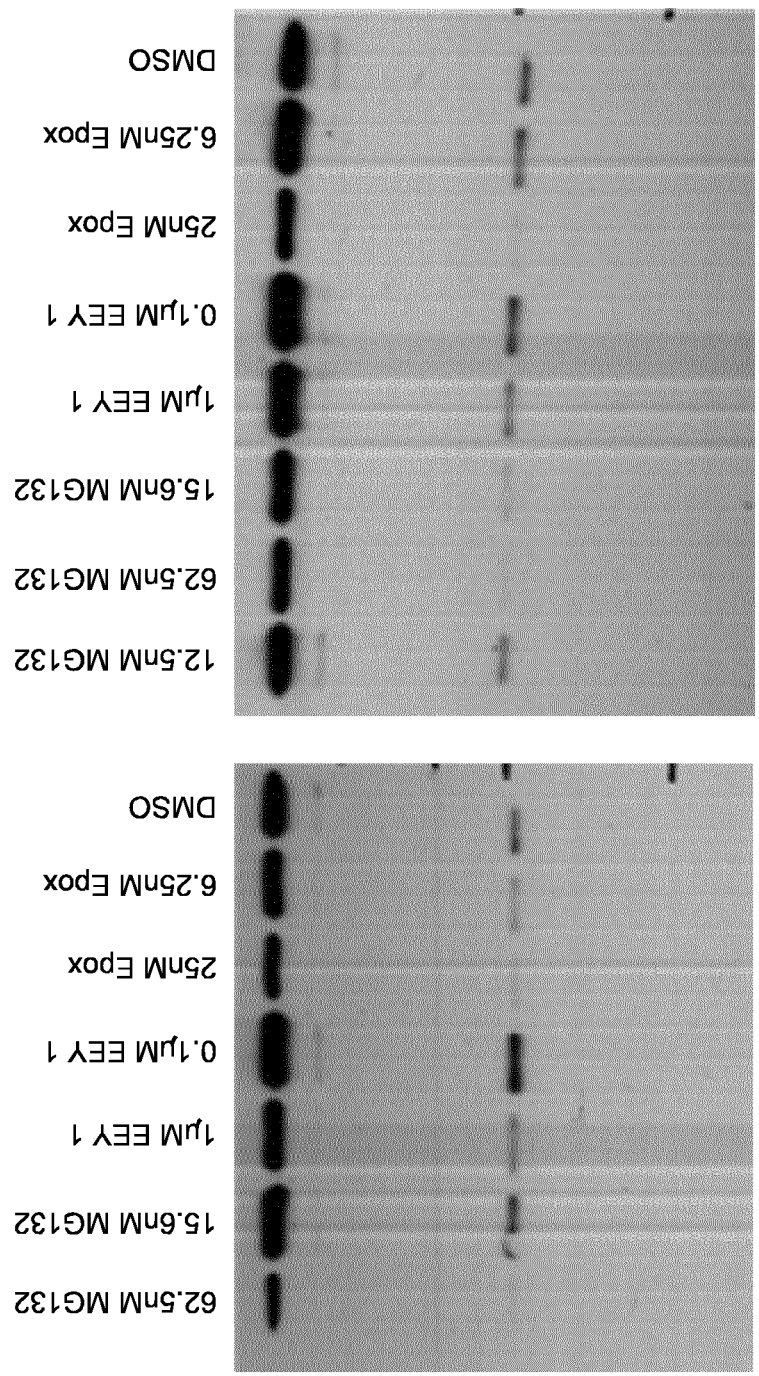
FIG. 22 depicts a western blot analysis for antibody in the supernatant of batch cultures post transient transfection of the host cell pools both immediately after culture in the presence of either proteasome or ERAD inhibitors (left gel) or following subculture for two passages in the absence of the inhibitors (right gel). Assessment of cB72.3 concentration from supernatant samples taken at 168 hours post transfection following electroporation of $1 \times 10^7$ cells with 20 µg DNA and resuspension into 20 ml batch cultures. Prior to electroporation the host cell line was initially cultured in the presence of proteasome and ERAD inhibitors, then passaged twice in the absence of the inhibitors. Western blots were probed using anti-heavy chain antibody (Sigma).

Third, the antibody in the supernatant of batch cultures post transient transfection of the host cell pools both immediately after culture in the presence of either proteasome or ERAD inhibitors or following subculture for two passages in the absence of the inhibitors was assessed via western blot (FIG. 22). Assessment of cB72.3 concentration from supernatant samples taken at 168 hours post transfection following electroporation of $1 \times 10^7$ viable cells with 20 μg DNA and resuspension into 20 ml batch cultures. Prior to electroporation the host cell line was initially cultured in the presence of proteasome and ERAD inhibitors, then passaged twice in the absence of the inhibitors. Western blots were probed using anti-heavy chain antibody (Sigma). As shown in FIG. 22, various combinations of the protein degradation inhibitors gave more intense antibody bands than the DMSO control cells, providing evidence that the culturing of the host cell in the presence of proteasome inhibitors can be used to adapt/select for cells with the capability of higher recombinant protein production.

CONCLUSIONS

The effects of proteasome or ERAD inhibitor presence during culture of the host cell population prior to transfection show, inter alia, an increase in cell specific productivity and titre when low concentrations of Eeyarestatin I (0.1 μM) are added to the culture media for the selection/adaptation of the cells. This suggests that selection/adaptation of a CHO host cell line in the presence of the protein degradation inhibitors can be used to generate a host population with enhanced ability to produce recombinant protein. However, in order for the proteasome or ERAD inhibitor selection to be most effective the demand of the production of a recombinant product is required. In order for populations to emerge with stable phenotypes (e.g., enhanced product titre and quality) the host may be cultured for longer periods and higher generation numbers.

What is claimed is:

1. A method of making a producer cell line that is capable of producing a recombinant polypeptide product (i) in increased quantity or (ii) having improved quality, the method comprising:
   a) contacting a population of cells with a first inhibitor of a protein degradation pathway;
   b) evaluating the effect of the first inhibitor on the quantity or the quality of an endogenously or exogenously expressed polypeptide produced by a first cell present in the population of cells by comparison with a reference value;
   c) selecting and isolating the first cell or progeny of the first cell wherein the first cell or progeny of the first cell produces the endogenously or exogenously expressed polypeptide (i) in increased quantity or (ii) having improved quality compared to the reference value; and
   d) establishing a producer cell line from the first cell or progeny of the first cell; thereby making the producer cell line that is capable of producing the recombinant polypeptide product (i) in increased quantity or (ii) having improved quality.

2. The method of claim 1, wherein the first inhibitor is a proteasome inhibitor, a ubiquitin pathway inhibitor, or an ERAD inhibitor.

3. The method of claim 1, wherein the polypeptide produced by the first cell is a recombinant protein encoded by a first exogenous nucleic acid.

4. The method of claim 1, wherein
the quality of the polypeptide produced by the first cell is improved, and the quality is selected from the proportion of the group consisting of:
the polypeptide with respect to unwanted isoforms, product fragments, or truncated forms;
properly folded product;
functional or enzymatically active product;
aggregated product; and
fragmented or unwanted isoforms.

5. The method of claim 1, wherein:
(a) the first inhibitor is a proteasome inhibitor, wherein the proteasome inhibitor inhibits or reduces the activity of one or more of the 20S core subunit, the 19S regulatory subunit, the 11S regulatory particle, or a chaperone protein that assists in proteasome assembly;
(b) the first inhibitor is an ERAD inhibitor, wherein the ERAD inhibitor inhibits or reduces the activity of one or more of calnexin/calreticulin, UDP-glucose-glycoprotein glucosyltransferase, ER degradation enhancing α-mannosidase-like protein (EDEM), ER mannosidase I, Sec61, CDC148p (VCP/p97),
Hrd1, Doa10, Ubc6, Ubc1, Cue1, or Ubc7; or
(c) the first inhibitor is a ubiquitin pathway inhibitor, wherein the ubiquitin pathway inhibitor inhibits or reduces the activity of one or more of: E1 ubiquitin activating enzyme, E2 ubiquitin conjugating enzyme, or E3 ubiquitin ligase.

6. The method of claim 5, wherein the first inhibitor is a proteasome inhibitor selected from: MG132, epoxomicin, bortezomib, ixazomib, carfilzomib, disulfiram, CEP-18770, ONX 0912, salinosporamide, LLnV, CEP1612, lactacystin, PS-341, and eponomicin, or wherein the ERAD inhibitor is eeyarestatin I.

7. The method of claim 1, wherein the population of cells is contacted with a concentration of the first inhibitor that is sufficient to reduce culture viability, by about 20%, 25%, 30%, 35%, 40%, 45%, 50%, 55%, 60%, 65%, 70%, or 75%, as compared to the culture viability before the culture is contacted with the first inhibitor or as compared to a culture that is not contacted with the first inhibitor.

8. The method of claim 1, wherein:
the first inhibitor is MG-132 and the concentration of MG-132 is less than 0.5 µM; or
the first inhibitor is epoxomicin and the concentration of epoxomicin is less than 0.05 µM epoxomicin.

9. The method of claim 1, wherein the population of cells is contacted by or cultured in the presence of the first inhibitor for 24, 48, 72, 96, or more hours.

10. The method of claim 1, wherein the population of cells is contacted by the first inhibitor 24, 48, 72, 96, or 168 hours prior to or after a MSX selection step, or simultaneously with a MSX selection step.

11. The method of claim 1, wherein the first cell is selected from the group consisting of Hela, HEK293, H9, HepG2, MCF75 Jurkat, NIH3T3, PC12, PER.C6, BHK, VERO, SP2/0, NSO, YB2/0, EB66, C127, L cell, COS, QC1-3, and a CHO cell.

12. The method of claim 1, wherein the polypeptide produced by the first cell is evaluated for a parameter related to a physical or functional property selected from the group consisting of primary sequence, glycosylation, primary, secondary, tertiary, or quaternary structure, activity, degree of glycosylation, degree of aggregation, proportion of the recombinant polypeptide having a preselected monomeric, dimeric, or trimeric structure, and the proportion of the recombinant polypeptide having a preselected non-denatured or non-aggregated structure.

13. The method of claim 1, further comprising introducing a first exogenous nucleic acid that encodes the recombinant polypeptide product into the population of cells, prior to step a).

14. The method of claim 13, further comprising introducing a second exogenous nucleic acid encoding a selection marker into the population of cells, wherein the second exogenous nucleic acid is introduced prior to step a), and wherein the second exogenous nucleic acid is introduced simultaneously with the introduction of the first exogenous nucleic acid.

15. The method of claim 14, wherein the second exogenous nucleic acid encodes glutamine synthetase.

16. The method of claim 1, further comprising determining if the first cell comprises one or more exogenous nucleic acids integrated into a nucleic acid of the first cell, wherein determining if the first cell comprises one or more exogenous nucleic acids integrated into a nucleic acid of the first cell consists of a selection step selected from the group consisting of MSX selection, MTX selection, antibiotic selection, yeast growth selection, and selection based on color change or surface expression of a marker.

17. The method of claim 16, further comprising an additional selection step, wherein the selection step is selected from the group consisting of FACS, magnetic separation, colony picking, microfluidic cell sorting, and microfluidic cell destruction.

18. The method of claim 16, wherein the selection step is antibiotic selection and the antibiotic selection comprises selection for resistance to an antibiotic selected from the group consisting of hygromycin, neomycin (G418), zeocin, puromycin, and blasticidin.

19. The method of claim 1, further comprising introducing to the population of cells an agent that assists in protein folding comprising a nucleic acid encoding a chaperone protein or component of the protein folding pathway.

20. The method of claim 1, further comprising after a) and before b): culturing the first cell, or progeny of the first cell, in the absence of the first inhibitor for at least 1, 2, 3, 4, 5, 6, 7, 8, 9, 10, or more passages or for at least 12, 24, 48, or 72 hours.

21. The method of claim 1, further comprising contacting the population of cells with a second inhibitor of a protein degradation pathway.

22. The method of claim 21, wherein the population of cells is contacted with the first and second inhibitors of protein degradation concurrently or sequentially.

23. The method of claim 21, wherein the first inhibitor is selected from the group consisting of:
(i) MG132, epoxomicin, and eeyarestatin and second inhibitor of protein degradation is selected from MG132, epoxomicin, and eeyarestatin I;
(ii) a proteasome inhibitor and the second inhibitor is a proteasome inhibitor;
(iii) a proteasome inhibitor and the second inhibitor is an ERAD inhibitor or an ubiquitin pathway inhibitor;
(iv) an ERAD inhibitor and the second inhibitor is an ERAD inhibitor;
(v) are ERAD inhibitor and the second inhibitor is an ubiquitin pathway inhibitor or a proteasome inhibitor;
(vi) the first inhibitor is an ubiquitin pathway inhibitor and the second inhibitor is an ubiquitin pathway inhibitor; and (vii) the first inhibitor is an ubiquitin pathway inhibitor and the second inhibitor is an ERAD inhibitor or a proteasome inhibitor.

24. The method of claim 1, wherein the population of cells is a eukaryotic cell.

25. The method of claim 1, wherein the population of cells is selected from the group consisting of mouse, rat, Chinese hamster, Syrian hamster, monkey, ape, human, dog, camel, horse, ferret, cat, an insect, a plant, duck, parrot, fish, and yeast.

26. The method of claim 1, wherein the quantity or the quality of the endogenously or exogenously expressed polypeptide produced in step (b) is evaluated by comparison with the quantity or quality of the polypeptide produced by a cell that has not been contacted by the inhibitor of protein degradation.

27. The method of claim 1, wherein the first cell is isolated after step (a) and before step (b).

28. The method of claim 1, wherein the producer cell line secretes the recombinant polypeptide product.

29. The method of claim 1, wherein the producer cell line produces the recombinant polypeptide product in the absence of the first inhibitor of a protein degradation pathway.

30. The method of claim 1, further comprising introducing an exogenous nucleic add that expresses the recombinant polypeptide product into the producer cell line.

31. The method of claim 1, wherein the first cell is a eukaryotic cell.

32. The method of claim 1, wherein the first cell is a mammalian cell.

33. The method of claim 1, wherein the first cell is a CHO-derived cell.

34. The method of claim 33, wherein the CHO-derived cell is selected from the group consisting of a CHOK1, CHOK1SV, Potelligent CHOK1SV, CHO GS knockout, CHOK1SV GS-KO, CHOS, CHO DG44, CHO DXB11, and a CHOZN cell.

35. A method of making a producer cell line that produces a recombinant polypeptide (i) in an increased quantity or (ii) having improved quality, the method comprising:
  a) contacting a population of cells which comprise an exogenous nucleic acid encoding the recombinant polypeptide and which express the recombinant polypeptide with a first inhibitor of a protein degradation pathway;
  b) evaluating the effect of the first inhibitor on the quantity or the quality of the recombinant polypeptide produced by a first cell present in the population of cells by comparison with a reference value;
  c) selecting and isolating the first cell or progeny of the first cell wherein the first cell or progeny of the first cell produces the recombinant polypeptide (i) in increased quantity or (ii) having improved quality compared to the reference value, and
  d) establishing a producer cell line from the first cell or progeny of the first cell; thereby making the producer cell line that produces the recombinant polypeptide (i) in increased quantity or (ii) having improved quality.

36. The method of claim 35, wherein the quantity or the quality of the polypeptide produced in step (b) is evaluated by comparison with the quantity or quality of the polypeptide produced by a cell that has not been contacted by the inhibitor of protein degradation.

* * * * *